United States Patent
Haynes et al.

(10) Patent No.: US 6,649,647 B1
(45) Date of Patent: Nov. 18, 2003

(54) TRIOXANE DERIVATIVES

(76) Inventors: Richard Haynes, The Hong Kong University of Science & Technology, House 2, 1 University Road, Clear Water Bay, Kowloon, Hong Kong (CN); Ho-Wai Chan, Flat 15, 2/F, Kam Young House, Kam Fung Court, Ma On Shan, Shatin, New Territories, Hong Kong (CN); Wai-Lun Lam, 6/F 100 Shantung Street, Mongkok, Kowloon, Hong Kong (CN); Hing-Wo Tsang, 20A To Shek Village, Sha Tin, New Territories, Hong Kong (CN); Wen-Luan Hsiao, The Hong Kong Univ. of Science & Technology, Clear Water Bay, Tower 7-5 A, Kowloon, Hong Kong (CN); Hans-Georg Lerchen, Süderstrasse 3, B-51375 Leverkusen (DE); Jörg Baumgarten, Henselweg 13, D-42115 Wuppertal (DE)

( * ) Notice: Subject to any disclaimer, the term of this patent is extended or adjusted under 35 U.S.C. 154(b) by 0 days.

(21) Appl. No.: 09/743,860
(22) PCT Filed: Jul. 14, 1999
(86) PCT No.: PCT/GB99/02276
§ 371 (c)(1), (2), (4) Date: Apr. 15, 2002
(87) PCT Pub. No.: WO00/04026
PCT Pub. Date: Jan. 27, 2000

(30) Foreign Application Priority Data

Jul. 14, 1998 (EP) ............................................. 98305593
Oct. 12, 1998 (EP) ............................................. 98308283

(51) Int. Cl.[7] ..................... A61K 31/357; C07D 493/12
(52) U.S. Cl. ..................... 514/450; 549/348; 514/451; 514/452; 424/9.2
(58) Field of Search ..................... 574/450; 549/348; 424/9.2; 514/450, 451, 452

(56) References Cited

U.S. PATENT DOCUMENTS

| | | | |
|---|---|---|---|
| 5,225,562 A | | 7/1993 | McChesney et al. ........ 546/270 |
| 5,578,637 A | * | 11/1996 | Lai et al. .................... 514/450 |

FOREIGN PATENT DOCUMENTS

| | | | | |
|---|---|---|---|---|
| CN | | 490829 | 5/1997 | |
| WO | WO 91/14689 | | 10/1991 | ................... 493/10 |
| WO | WO 94/08195 | | 4/1994 | ................... 493/20 |
| WO | WO 99/33461 | | 7/1999 | ................... 31/335 |

OTHER PUBLICATIONS

Paitayatat et al. "Correlation of Antimalarial Activity of Artemisinin Derivatives with Binding Affinity with . . . " *J. Med. Chem.* 40, 633–638 (1997).
Vroman et al. "Conjugate Addition of Trimethylsilylmethyl Cuprates to Artemisinic Acid: Homologation and Subsequent . . . " *Letters*, 1438–1440 (1997).
Avery et al. Structure–Activity Relationships of the Antimalarial Agent Artemisin. 5. Analogs of 10–Deoxartemisnin . . . *J. Med. Chem.* 39, 4149–4155 (1996).
Avery et al. "Structure—Activity Relationships of the Antimalarial Agent Artemisinin. 1. Synthesis and Comparative Molecular . . . " *J. Med. Chem.* 36, 4264–4275 (1993).
Vroman et al. "Copper(I) Catalyzed Conjugate Addition of Grignard Reagents to Acrylic Acids: Homologation of Artemisinic Acid and . . . " *Tetrahedron Letters* 38, 6173–6176 (1997).
Mekonnen et al. "A New Route to N–Substituted 11–Azaartemisinins" *Tetrahedron Letters* 38, 731–734 (1997).
Haynes et al. "Efficient Preparation of Novel Qinghaosu (Artemisinin) Derivatives: Conversion of Qinghao (Artemisinic) Acid into . . . " *Letters*, 481–483 (1992).
Torok et al. "Synthesis and Reactions of 11–Azaartemisinin and Derivatives" *Tetrahedron Letters* 36, 829–832 (1995).
Woo et al. "Direct Conversion of Pyranose Anomeric OH—F—R in the Artemisinin Family of Antimalarial Trioxanes" *Tetrahedron Letters* 39, 1533–1536 (1998).
Torok et al. "Synthesis and Antimalarial Activities of N–Substituted 11–Azaartemisinins" *J. Med. Chem.* 38, 5045–5050 (1995).

* cited by examiner

*Primary Examiner*—Charanjit S. Aulakh
(74) *Attorney, Agent, or Firm*—Heslin Rothenberg Farley & Mesiti P.C.; Mary Louise Gioeni, Esq.

(57) ABSTRACT

This invention relates to compounds containing a trioxane moiety, especially certain artemisinin derivatives, which have cytotoxic and antitumour activity and their use in the treatment of cancer. Some of these compounds comprise a ligand which is capable of binding to a nucleic acid and a group containing a trioxane moiety which is capable of acting as source of free radicals which are capable of chemically interacting with a nucleic acid. Processes for the preparation of such compounds and pharmaceutical compositions containing such compounds are also provided.

7 Claims, No Drawings

TRIOXANE DERIVATIVES

CROSS REFERENCE TO RELATED APPLICATIONS

This application is a US national phase entry under 35 USC 371 of PCT application PCT/GB99/02276, filed Jul. 14, 1999, and published in English as WO 00/04026 on Jan. 27, 2000. PCT/GB99/02276 claimed the priority of European applications EP/98305593.0 and EP/98308283.5, filed Jul. 14, 1998, and OCT. 12, 1998, respectively. The entire disclosures of all are incorporated herein by reference.

This invention relates to certain compounds containing a trioxane moiety which have cytotoxic and antitumour activity and their use in the treatment of cancer, processes for preparing such compounds and pharmaceutical compositions containing such compounds.

The compound artemisinin, also known as ginghaosu (1), is a tetracyclic 1,2,4-trioxane occurring in *Artemisia annua*. Artemisinin and its derivatives dihydroartemisinin (2), artemether (3) and sodium artesunate (4) are routinely used for the treatment of malaria and are particularly effective against cerebral malaria.

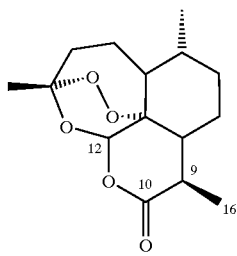

Artemisinin 1

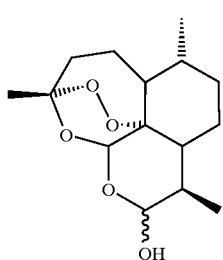

Dihydroartemisinin 2

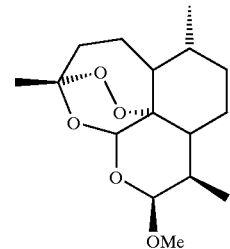

Artemether 3

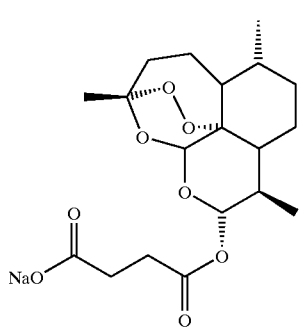

Sodium Artesunate 4

Different modes of action have been proposed by various groups to account for the action of artemisinin and its derivatives in treating malaria (Posner et al., *J.Am.Chem.Soc.*1996,118,3537; Posner at al., *J.Am.Chem.Soc.*1995,117,5885; Posner at al., *J. Med.Chem.*1995,38,2273). Whilst the mode of action of artemisinin as an antimalarial has not been unequivocally established, it has been demonstrated that the peroxide linkage is essential for expression of activity. One proposal embodies cleavage of the endoperoxide bridge by intraparasitic heme iron (II) to generate unstable free radical intermediates which alkylate malaria proteins (see Scheme 1 below).

Scheme 1

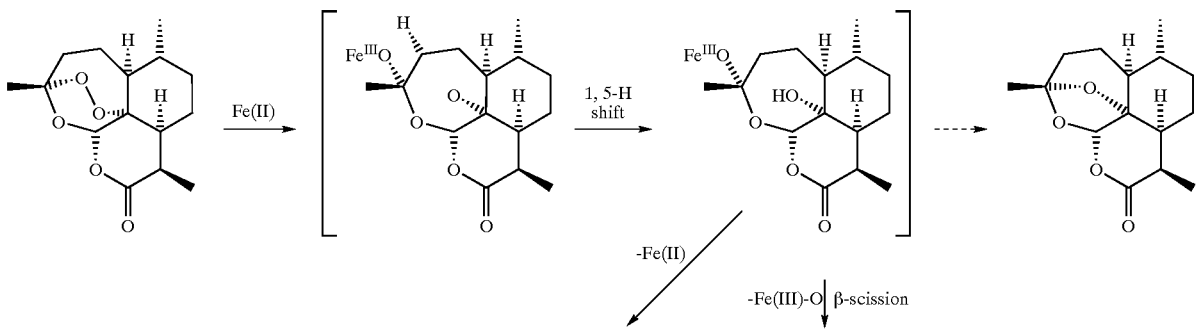

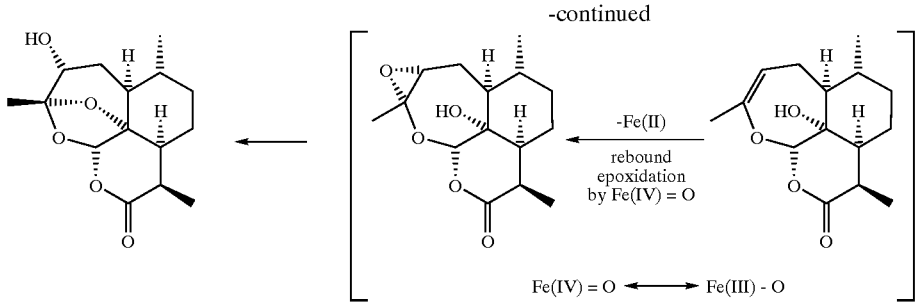

Recently, the isolation of a covalent adduct formed between artemisinin and a heme model Mn[II]TPP tends to support this proposal (Robert et al, *J.Am.Chem.Soc.* 1997,119,5968). Formation of artemisinin-heme and artemisinin-protein adducts have also been reported when *P. falciparum* infected erythrocytes have been incubated in vitro with radiolabelled artemisinin (Hong et. al., *Mol.Biochem.Parasitol.*,1994,63, 121; Asawamahasakda et al., *Antimicrob.Agents Chemother.*, 1994,38,1854). However, attention has also focused on perferryl iron as the active species as this has been unambiguously detected when artemisinin analogues have been incubated with iron(II). Its postulated mode of formation is rather curious in that it is presumed to arise via a reductive scission of the peroxide bond by iron(II) (see Scheme I).

Based on a careful analysis of products obtained from artemisinin on treatment both with iron (II) and iron (III), it has been shown that the trioxane unit acts as a source of free hydroperoxide or equivalent, which is then capable of generating hydroxyl or alkoxy radicals, or of perferryl iron by direct coordination to the iron(II) site in ferroheme according to well-established models (Haynes et al., *Today's Life Science*,1993,14; *Tetrahedron Lett.*1996,37,253;1996,37, 257). These are set out in Scheme 2 below.

Peroxides in general are biologically active. Tert-butylhydroperoxide is used as a potent inhibitor of bacterial growth on fish, although it is quite toxic towards many living organisms. The root growth inhibitor of Formula A below also has a peroxide bridge in the ring and the inhibitory action on the plant root is correlated with the peroxide bridge. Recently, the simple cyclic peroxide of Formula B below has been studied as a candidate for radical releasing drugs, because these compounds are known to generate hydroxyl radicals by heat stimuli.

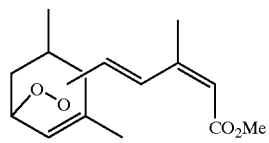

(A)

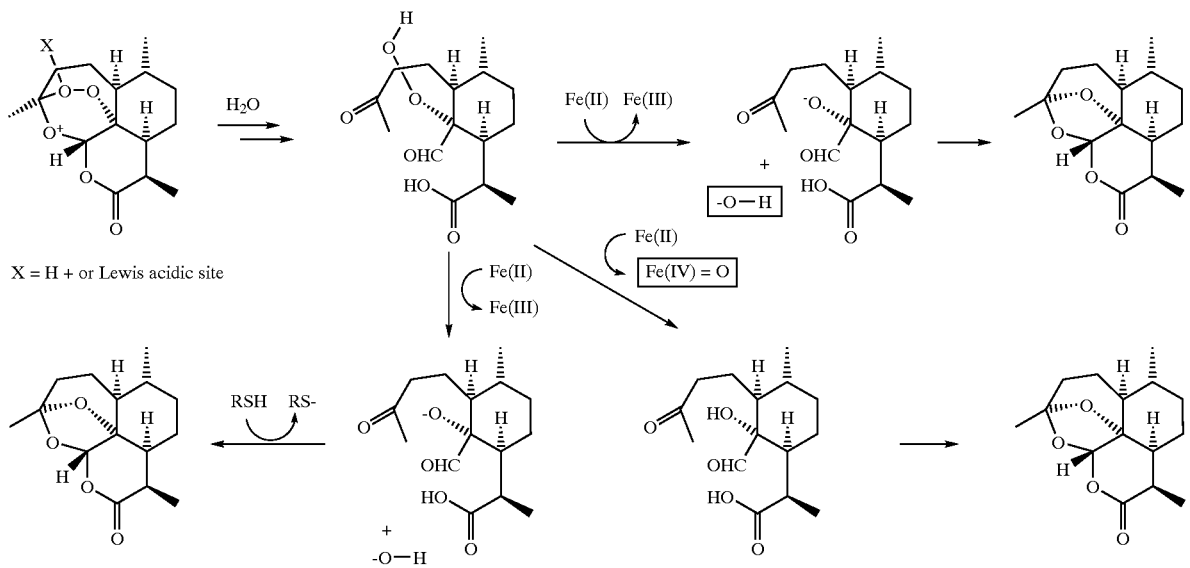

-continued

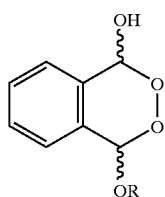
(B)

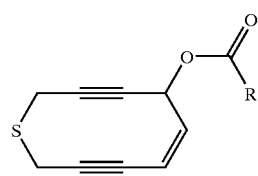
(C)

Certain artemisinin derivatives which contain a peroxide moiety have also been tested for biological activity other than antimalarial activity. For instance, the cytotoxicity of artemisinin, dehydroartemisinin, artemisitene, arteether, ethylperoxyartemisitene and an ether dimer of artemisinin to Ehrlich ascites tumor cells has been reported (Beekman et al., Phytother.Res.,1996,10,140; Woerdenberg et al., J.Nat.Prod.,1993,56,849). Selective cancer cell cytotoxicity from exposure to dehydroartemisinin and holotransferrin, a non-heme iron-transport protein saturated with iron, has also been disclosed (Lai et al.,Cancer Lett.,1995,91,41 and U.S. Pat. No. 5,578,637) with the drug combination being approximately 100 times more effective on molt-4 cells than lymphocytes.

It is known that some biologically active molecules contain chemical groups which enable the molecule to bind to DNA. The method by which DNA-binding occurs will depend upon the overall structure of the molecule and the nature of the chemical groups contained within the molecule.

For instance, the major and minor grooves of double helical DNA are occupied by water under physiological conditions. However, certain oligopeptidic compounds, such as netropsin and distamycin can displace water molecules and form strong hydrogen bonds with hydrophilic groups along the DNA strands. The crescent-shaped structures of netropsin and distamycin can make them fit tightly into the helical structure of DNA.

Alternatively, some compounds contain groups which are capable of intercalating with DNA. Intercalators are flat aromatic compounds which insert between the bases of DNA, the ensemble being held together by hydrophilic and π—π interactions. Well characterised examples of intercalators are provided by anthracyclines, such as adriamycin and daunomycin, which are used for treatment of cancer, and acridines, such as amascrine, which is used for treating acute leukaemia and malignant lymphomas, the antitumour activity is associated with the intercalating property of these compounds.

The technique of incorporating minor groove binding agents related to netropsin or distamycin, or intercalating agents to free-radical generators or electrophilic alkylating agents as a means of inducing DNA strand cleavage is well known. For instance, Toshima and co-workers (J.Am.Chem.Soc., 1995,117,4822; J.Chem.Soc., Chem.Commun.,1993,1525; J.Chem.Soc., Chem.Commun., 1992,1306; Heterocycles, 1997,45,851) have synthesised DNA-cleaving hybrid molecules of Formula C below containing enediyne and DNA intercalators.

R = 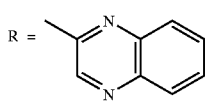

R = 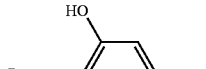

R = 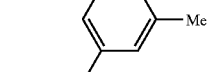

R = 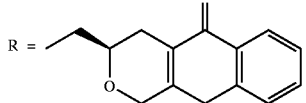

R = 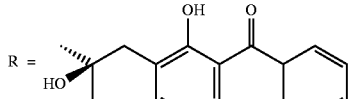

R = 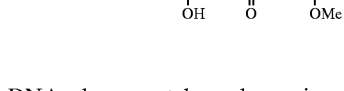

DNA cleavage takes place via collapse of the enediyne moiety to a highly reactive diradical which abstracts hydrogen atoms from C4' of the deoxyribose in the DNA.

The best known anti-cancer agent, which acts by cleaving DNA through generation of active oxygen species, is bleomycin (BLM). It is a glycopeptide which binds to DNA via intercalation of the bis-thiazole group. The compound sequesters iron to form a planar BLM-iron(II) complex and activation by oxygen then provides perferryl capable of abstracting hydrogen atoms from C4' of deoxyribose. DNA cleavage takes place mainly at the C or T position in GC or GT array.

Examples of hydroxyl radical participation in DNA cleavage are also observed in many other anticancer drugs.

It has how been discovered that artemisinin and synthetic trioxane derivatives can be chemically modified by the attachment of a DNA-binding group to form analogues of artemisinin and synthetic trioxane derivatives which are capable of targeting DNA in pathogenic organisms. Moreover, in the course of synthesising such compounds, other artemisinin and synthetic trioxane derivatives were prepared which do not contain a DNA-binding group but which were found to exhibit cytotoxic and antitumour activity. According to a first aspect of the present invention there is therefore provided a compound of the general formula I

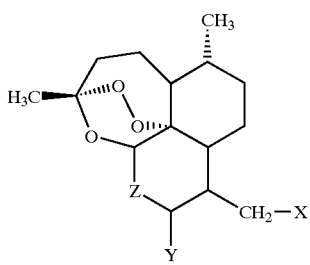
(I)

or a salt thereof,
in which
X represents a hydrogen atom or a group —NR$^1$R$^2$, —CHR$^8$R$^9$ or Ar;
Y represents a hydrogen or halogen atom, an or hydroxyl oxo group, an optionally substituted cycloalkyl, aryl, C-linked heteroaryl or heterocyclylalkyl group or a group —NR$^3$R$^4$, —O—CO—R$^5$ or —OR$^6$; and
Z represents an oxygen atom or a group =NR$^7$; where
R$^1$ and R$^2$ independently represent an optionally substituted alkyl, cycloalkyl, aryl or aralkyl group;
or R$^1$ and R$^2$ together with the interjacent nitrogen atom represent an optionally substituted heterocyclic group or an amino group derived from an optionally substituted amino acid ester;
R$^3$ represents a hydrogen atom or an optionally substituted alkyl, alkenyl or alkynyl group;
R$^4$ represents an optionally substituted alkyl, alkenyl, alkynyl, cycloalkyl, aryl or aralkyl group;
or R$^3$ and R$^4$ together with the interjacent nitrogen atom represent an optionally substituted heterocyclic group or an amino group derived from an optionally substituted amino acid ester;
R$^5$ represents an optionally substituted alkyl, alkenyl, alkynyl, cycloalkyl, aryl, aralkyl, heterocyclic or polycyclic group;
R$^6$ represents an optionally substituted alkyl, alkenyl, alkynyl, cycloalkyl, aryl, aralkyl, heterocyclic or polycyclic group;
R$^7$ represents a hydrogen atom or an optionally substituted alkyl, alkenyl, alkynyl, aralkyl or heterocyclylalkyl group;
R$^8$ represents a hydrogen atom or an optionally substituted alkyl, alkenyl, alkynyl, aryl or alkoxycarbonyl group;
R$^9$ represents a nitro group of an optionally substituted alkyl, alkenyl, alkynyl, aryl, alkanoyl, aroyl, alkoxycarbonyl or aryloxycarbonyl group; or
R$^8$ and R$^9$ together with the interjacent carbon atom represent an optionally substituted cycloalkyl or polycyclic group; and Ar represents an optionally substituted aryl or heteroaryl group;
with the provisos that
(i) when X is a group —NR$^1$R$^2$, then Y is an oxo group and Z is an oxygen atom;
(ii) when Z is a group =NR$^7$, then X is a hydrogen atom and Y is an oxo group;
(iii) when X is a hydrogen atom and Z is an oxygen atom, then Y is not an oxo, methoxy, ethoxy or 3-carboxypropanoyloxy group;
(iv) when Y is a hydrogen atom or a hydroxyl group, then X is a group —CHR$^8$R$^9$;
for use as a cytotoxic agent.

Suitable salts include acid addition salts and these may be formed by reaction of a suitable compound of formula I with a suitable acid, such as an organic acid or a mineral acid. Acid addition salts formed by reaction with a mineral acid are particularly preferred, especially salts formed by reaction with hydrochloric or hydrobromic acid. Compounds of formula I in which X represents a group —NR$^1$R$^2$ or Y represents a group —NR$^3$R$^4$ where R$^1$, R$^2$, R$^3$ and R$^4$ are as defined above are particularly suitable for the formation of such acid addition salts. Suitable salts also include metal salts of compounds in which the substituent R$^5$ or R$^6$ bears a terminal carboxyl group. Such metal salts are preferably formed with an alkali metal atom, such as a lithium, sodium or potassium atom, or with a group —LHal, where L is an alkaline earth metal atom, such as magnesium, and Hal is a halogen atom, preferably a chlorine, bromine or iodine atom. Sodium salts are particularly preferred.

Any alkyl, alkenyl or alkynyl group, unless otherwise specified, may be linear or branched and may contain up to 12, preferably up to 6, and especially up to 4 carbon atoms. Preferred alkyl groups are methyl, ethyl, propyl and butyl. It is preferred that any alkenyl or alkynyl group is not an alk-1-enyl or alk-1-ynyl group. In other words, there should preferably be at least one methylene group —CH$_2$— or similar sp$^3$-hybridised centre between a carbon atom forming part of the double or triple C—C bond and the atom to which the group is attached. Preferred alkenyl and alkynyl groups include propenyl, butenyl, propynyl and butynyl groups. When an alkyl moiety forms part of another group, for example the alkyl moiety of an aralkyl group, it is preferred that it contains up to 6, especially up to 4, carbon atoms. Preferred alkyl moieties are methyl and ethyl.

An aryl group may be any monocyclic or polycyclic aromatic hydrocarbon group and may contain from 6 to 24, preferably 6 to 18, more preferably 6 to 16, and especially 6 to 14, carbon atoms. Preferred aryl groups include phenyl, naphthyl, anthryl, phenanthryl and pyryl groups, especially a phenyl or naphthyl, and particularly a phenyl, group. When an aryl moiety forms part of another group, for example the aryl moiety of an aralkyl group, it is preferred that it is a phenyl, naphthyl, anthryl, phenanthryl or pyryl, especially phenyl or naphthyl, and particularly a phenyl, moiety.

An aralkyl group may be an alkyl group substituted by an aryl group. A preferred aralkyl group contains from 7 to 30, particularly 7 to 24 and especially 7 to 18, carbon atoms, particularly preferred aralkyl groups being benzyl, naphthylmethyl, anthrylmethyl, phenanthrylmethyl and pyrylmethyl groups. A particularly preferred aralkyl group is a benzyl group.

A cycloalkyl group may be any saturated cyclic hydrocarbon group and may contain from 3 to 12, preferably 3 to 8, and especially 3 to 6, carbon atoms. Preferred cycloalkyl groups are cyclopropyl, cyclopentyl and cyclohexyl groups.

A polycyclic group may be any saturated or partially unsaturated hydrocarbon group which contains more than one ring system. Such ring systems may be "fused", that is, adjacent rings have two adjacent carbon atoms in common, "bridged", that is, the rings are defined by at least two common carbon atoms (bridgeheads) and at least three acyclic chains (bridges) connecting the common carbon atoms, or "spiro" compounds, that is, adjacent rings are linked by a single common carbon atom. It is also envisaged that a polycyclic group may contain more than one of these types of ring system. Polycyclic groups preferably contain from 4 to 30, particularly 4 to 26, and especially 6 to 18, carbon atoms. Bicyclic, tricyclic and tetracyclic groups are particularly preferred. Preferred tricyclic groups contain from 4 to 14, especially 6 to 10, carbon atoms with bornyl and particularly, isobornyl groups being especially preferred. Preferred tricyclic groups contain from 5 to 20, especially 6 to 14, carbon atoms with adamantyl groups being especially preferred. Preferred tetracyclic groups contain from 6 to 26, especially 6 to 18, carbon atoms. Cholestanyl and cholestenyl groups are further preferred polycyclic groups.

A heteroaryl group may be any aromatic monocyclic or polycyclic ring system which contains at least one heteroatom. Preferably a 5- to 14-membered, and especially a 5- to 10-membered, aromatic ring system containing at least one heteroatom selected from oxygen, sulphur and nitrogen atoms. Preferred heteroaryl groups include pyridyl, pyrylium, thiopyrylium, pyrrolyl, furyl, thienyl, indolinyl, isoindolinyl, indolizinyl, imidazolyl, pyridonyl, pyronyl, pyrimidinyl, pyrazinyl, oxazolyl, thiazolyl, purinyl, quinolinyl, isoquinolinyl, quinoxalinyl, pyridazinyl, benzofuranyl, benzoxazolyl and acridinyl groups. A C-linked heteroaryl group is therefore a heteroaryl group as defined above which is linked to the tetracyclic 1,2,4-trioxane moiety of a compound of general formula I via a carbon atom in the heteroaromatic ring system.

A heterocyclic group may be any monocyclic or polycyclic ring system which contains at least one heteroatom and may be unsaturated or partially or fully saturated. The term "heterocyclic" thus includes heteroaryl groups as defined above as well as non-aromatic heterocyclic groups. Preferably, a heterocyclic group is a 3- to 18- membered, particularly a 3- to 14-membered, especially a 5- to 10-membered, ring system containing at least one heteroatom selected from oxygen, sulphur and nitrogen atoms. Preferred heterocyclic groups include the specific heteroaryl groups named above as well as pyranyl, piperidinyl, pyrrolidinyl, dioxanyl, piperazinyl, morpholinyl, thiomorpholinyl, morpholinosulphonyl, tetrahydroisoquinolinyl and tetrahydrofuranyl groups.

A heterocyclylalkyl group may be an alkyl group substituted by a heterocyclic group. Preferably, the heterocyclic moiety is a 3- to 18- membered, particularly a 3- to 14-membered, and especially a 5- to 10-membered, heterocyclic group as defined above and the alkyl moiety is a $C_{1-6}$ alkyl, preferably $C_{1-4}$ alkyl, and especially methyl, group.

An amino acid may be any α-amino acid, such as glycine, alanine, valine, leucine, isoleucine, serine, threonine, cysteine, cystine, methionine, aspartic acid, glutamic acid, aspargine, glutamine, lysine, hydroxylysine, arginine, histidine, phenylalanine, tyrosine, tryptophan, proline, hydroxyproline or phenylglycine, and includes both D- and L-configurations. An amino acid ester may be any ester of such an amino acid, alkyl esters, particularly $C_{1-4}$ alkyl esters, being especially preferred.

When any of the foregoing substituents are designated as being optionally substituted, the substituent groups which are optionally present may be any one or more of those customarily employed in the development of pharmaceutical compounds and/or the modification of such compounds to influence their structure/activity, stability, bioavailability or other property. Specific examples of such substituents include, for example, halogen atoms, nitro, cyano, hydroxyl, cycloalkyl, alkyl, alkenyl, haloalkyl, cycloalkyloxy, alkoxy, haloalkoxy, amino, alkylamino, dialkylamino, formyl, alkoxycarbonyl, carboxyl, alkanoyl, alkylthio, alkylsulphinyl, alkylsulphonyl, alkylsulphonato, arylsulphinyl, arylsulphonyl, arylsulphonato, carbamoyl, alkylamido, aryl, aralkyl, optionally substituted aryl, heterocyclic and alkyl- or aryl-substituted heterocyclic groups. When any of the foregoing substituents represents or contains an alkyl or alkenyl substituent group, this may be linear or branched and may contain up to 12, preferably up to 6, and especially up to 4, carbon atoms. A cycloalkyl group may contain from 3 to 8, preferably from 3 to 6, carbon atoms. An aryl group or moiety may contain from 6 to 10 carbon atoms, phenyl groups being especially preferred. A heterocyclic group or moiety may be a 5- to 10-membered ring system as defined above. A halogen atom may be a fluorine, chlorine, bromine or iodine atom and any group which contains a halo moiety, such as a haloalkyl group, may thus contain any one or more of these halogen atoms.

It is particularly preferred that X represents a hydrogen atom or a group —$NR^1R^2$ or $CHR^8R^9$, where $R^1$, $R^2$, $R^8$ and $R^9$ are as defined above.

Preferably, X represents a hydrogen atom. It is also preferred that Z represents an oxygen atom.

In one aspect, it is preferred that Y represents a halogen atom, particularly a fluorine or bromine, and especially a fluorine, atom.

In another preferred aspect Y may represent a $C_{3-8}$ cycloalkyl group, a $C_{6-18}$ aryl group, a 5- to 10-membered C-linked heteroaryl group or a 5- to 10-membered heterocyclyl-$C_{1-6}$ alkyl group, each group being optionally substituted by one or more substituents selected from the group consisting of halogen atoms, hydroxyl, $C_{1-4}$ alkyl, $C_{2-4}$ alkenyl, $C_{1-4}$ haloalkyl, $C_{1-4}$ alkoxy, amino, $C_{1-4}$ alkylamino, di($C_{1-4}$ alkyl)amino, carboxyl, $C_{6-10}$ aryl, 5 to 10--membered heterocyclic and $C_{1-4}$ alkyl- or phenyl-substituted 5- to 10-membered heterocyclic groups. Preferably Y represents a $C_{6-18}$ aryl group optionally substituted by one or more substituents selected from the group consisting of halogen atoms, hydroxyl, $C_{1-4}$ alkyl, $C_{2-4}$ alkenyl, $C_{1-4}$ haloalkyl, $C_{1-4}$ alkoxy, $C_{1-4}$ haloalkoxy, amino, $C_{1-4}$ alkylamino, di ($C_{1-4}$ alkyl)amino and carboxyl groups. In particular, Y may represent a phenyl, naphthyl, anthryl or phenanthryl group, each group being optionally substituted by one or more substituents selected from the group consisting of halogen atoms and hydroxyl, methyl, vinyl, $C_{1-4}$ alkoxy and carboxyl groups.

In a particularly preferred sub-group of compounds, Y represents a phenyl, fluorophenyl, chlorophenyl, bromophenyl, trimethylphenyl, vinylphenyl, methoxyphenyl, dimethoxyphenyl, trimethoxyphenyl, carboxylphenyl, naphthyl, hydroxynaphthyl, methoxynaphthyl, anthryl or phenanthryl group. Compounds in which Y represents a dimethoxyphenyl or trimethoxyphenyl group are especially preferred.

In a further preferred aspect, Y may represent a group —$NR^3R^4$ where $R^3$ represents a hydrogen atom or a $C_{1-6}$ alkyl group and $R^4$ represents a $C_{1-6}$ alkyl, $C_{3-8}$ cycloalkyl, $C_{6-10}$ aryl or $C_{7-16}$ aralkyl group, or $R^3$ and $R^4$ together with the interjacent nitrogen atom represent a 5- to 10-membered heterocyclic group or an amino group derived from a $C_{1-6}$ alkyl ester of an amino acid, each group being optionally substituted by one or more substituents selected from the group consisting of halogen atoms, $C_{1-4}$ alkyl, $C_{1-4}$ haloalkyl, $C_{1-6}$ alkoxycarbonyl, phenyl, halophenyl, $C_{1-4}$ alkylphenyl, $C_{1-4}$ haloalkylphenyl, $C_{1-4}$ alkoxyphenyl, benzyl, pyridyl and pyrimidinyl groups. In particular, Y may represent a group —$NR^3R^4$ where $R^3$ represents a hydrogen atom or a $C_{1-4}$ alkyl group and $R^4$ represents a $C_{1-4}$ alkyl, $C_{3-6}$ cycloalkyl, phenyl or benzyl group, or $R^3$ and $R^4$ together with the interjacent nitrogen atom represent a 6- to 10-membered heterocyclic group or an amino group derived from a $C_{1-4}$ alkyl ester of an amino acid, each group being optionally substituted by one or more substituents selected from the group consisting of halogen atoms, $C_{1-4}$ haloalkyl, $C_{1-4}$ alkoxycarbonyl, phenyl, halophenyl, $C_{1-4}$ alkylphenyl, $C_{1-4}$ haloalkylphenyl, $C_{1-4}$ alkoxyphenyl, benzyl, pyridyl and pyrimidinyl groups.

In a particularly preferred sub-group of these compounds, Y represents a propylamino, cyclopentylamino, cyclohexylamino, phenylamino, fluorophenylamino, chlorophenylamino, bromophenylamino, iodophenylamino, methoxycarbonylphenylamino, biphenylamino, benzylamino, fluorobenzylamino, bis(trifluoromethyl)-benzylamino, phenylethylamino, phenylmethoxycarbonyl-methylamino, diethylamino, morpholinyl, thiomorpholinyl, S,S-dioxothiomorpholinyl (morpholinosulphonyl), indolinyl, tetrahydroisoquinolinyl, phenylpiperazinyl, fluorophenylpiperazinyl, chlorophenylpiperazinyl, methylphenylpiperazinyl, trifluoromethylphenylpiperazinyl, methoxyphenylpiperazinyl, benzylpiperazinyl, pyridylpiperazinyl and pyrimidinylpiperazinyl group. Compounds in which Y represents a phenylamino or fluorophenylamino group are especially preferred.

In another preferred aspect, Y may represent a group —O—CO—$R^5$ where $R^5$ represents an optionally substituted alkyl, aryl, aralkyl, heterocyclic or polycyclic group. Preferably, $R^5$ represents a $C_{1-6}$ alkyl, $C_{6-18}$ aryl, 5- to 18-membered heterocyclic or $C_{4-26}$ polycyclic group, each group being optionally substituted by one or more substituents selected form the group consisting of halogen atoms, hydroxyl, $C_{1-4}$ alkyl, $C_{1-4}$ haloalkyl, $C_{1-4}$ alkoxy, $C_{1-4}$ haloalkoxy, oxo, carboxyl and carboxylato groups. More preferably, $R^5$ represents a $C_{1-4}$ alkyl, $C_{6-14}$ aryl, 5- to 14-membered heterocyclic or $C_{6-14}$ polycyclic group, each group being optionally substituted by one or more substituents selected from the group consisting of halogen atoms, hydroxyl, $C_{1-4}$ alkyl, $C_{1-4}$ haloalkyl and oxo groups.

In a particularly preferred sub-group of these compounds, $R^5$ represents a methyl, phenyl, hydroxynaphthyl, anthryl, anthraquinonyl, quinolinyl, isoquinolinyl, quinoxalinyl or acridinyl group.

In a further preferred aspect, Y may represent a group —$OR^6$ where $R^6$ represents an optionally substituted alkyl, aryl, aralkyl, heterocyclic or polycyclic group. Preferably, $R^6$ represents a $C_{1-6}$ alkyl, $C_{6-24}$ aryl, $C_{7-30}$ aralkyl, 5- to 18- membered heterocyclic or $C_{4-26}$ polycyclic group, each group being optionally substituted by one or more substituents selected form the group consisting of halogen atoms, hydroxyl, $C_{1-8}$ alkyl, $C_{1-4}$ haloalkyl, $C_{1-4}$ alkoxy, $C_{1-4}$ haloalkoxy, carboxyl and $C_{1-4}$ alkoxycarbonyl groups. More preferably, $R^6$ represents a $C_{1-4}$ alkyl, $C_{6-14}$ aryl, $C_{7-18}$ aralkyl, 5- to 14-membered heterocyclic or $C_{6-18}$ polycyclic group, each group being optionally substituted by one or more substituents selected from the group consisting of halogen atoms, $C_{1-4}$ alkyl, $C_{1-4}$ haloalkyl, $C_{1-4}$ alkoxy and $C_{1-4}$ haloalkoxy groups.

In a particularly preferred sub-group of these compounds, $R^6$ represents a trifluoroethyl, methoxyphenyl, naphthyl, benzyl, fluorobenzyl, naphthylmethyl, anthrylmethyl, phenanthrylmethyl, pyrylmethyl, quinolinyl, trifluoromethylquinolinyl or cholestenyl group. Compounds in which $R^6$ represents a naphthylmethyl group are particularly preferred.

In another aspect, it is preferred that Z represents a group =$NR^7$. Preferably, $R^7$ represents a hydrogen atom or a $C_{1-6}$ alkyl, $C_{2-6}$ alkenyl, $C_{2-6}$ alkynyl, $C_{7-16}$ aralkyl or 5- to 10-membered-heterocyclic-$C_{1-6}$ alkyl group, each group being optionally substituted by one or more substituents selected from the group consisting of halogen atoms, cyano, nitro, $C_{1-4}$ haloalkyl, formyl, $C_{1-6}$ alkoxycarbonyl, $C_{1-6}$ alkanoyl, phenylsulphinyl, phenylsulphonyl and phenylsulphonato groups.

It is also preferred that $R^7$ represents a hydrogen atom or a $C_{1-4}$ alkyl, $C_{2-4}$ alkenyl, $C_{7-11}$ aralkyl or 5- to 10-membered-heterocyclic-$C_{1-4}$ alkyl group, each group being optionally substituted by one or more substituents selected from the group consisting of halogen atoms, hydroxyl and formyl groups.

Preferably, $R^7$ represents a hydrogen atom or a $C_{1-4}$ alkyl or benzyl group, each group being optionally substituted by one or more halogen atoms or hydroxyl groups.

More preferably, $R^7$ represents a hydrogen atom or a methyl, butyl, formylmethyl, hydroxyethyl, propenyl, benzyl, halobenzyl, especially fluorobenzyl, pyridylmethyl, thienylmethyl or furylmethyl group.

In a particularly preferred sub-group of these compounds, $R^7$ represents a hydrogen atom or a benzyl or fluorobenzyl group.

In another preferred aspect, X may represent a group —$CHR^8R^9$ where $R^8$ represents a hydrogen atom or a $C_{1-6}$ alkyl or $C_{1-6}$ alkoxycarbonyl group and $R^9$ represents a nitro, $C_{1-6}$ alkyl, $C_{1-6}$ alkanoyl, $C_{7-11}$ aroyl, $C_{1-6}$ alkoxycarbonyl or $C_{6-10}$ aryloxycarbonyl group, or $R^8$ and $R^9$ together with the interjacent carbon atom represent a $C_{3-8}$ cycloalkyl or $C_{4-26}$ polycyclic group, each group being optionally substituted by one or more substituents selected from the group consisting of halogen atoms, hydroxyl, $C_{1-4}$ alkyl, $C_{1-4}$ haloalkyl, $C_{1-4}$ alkoxy and $C_{1-4}$ haloalkoxy groups. Preferably, X represents a group —$CHRR^9$ where $R^8$ represents a hydrogen atom or a $C_{1-4}$ alkyl or $C_{1-4}$ alkoxycarbonyl group and $R^9$ represents a nitro, $C_{1-4}$ alkyl, $C_{1-4}$ alkanoyl, benzoyl, $C_{1-4}$ alkoxycarbonyl or benzoxycarbonyl group, or $R^3$ and $R^4$ together with the interjacent carbon atom represent a $C_{3-6}$ cycloalkyl, $C_{6-10}$ bicyclic or $C_{6-14}$ tricyclic group, each group being optionally substituted by one or more substituents selected from the group consisting of halogen atoms, hydroxyl, $C_{1-4}$ alkyl and $C_{1-4}$ haloalkyl groups.

In a particularly preferred sub-group of these compounds, X represents a nitromethyl, isopropyl, methoxycarbonylethyl, ethoxycarbonylmethyl, di(ethoxycarbonyl)methyl, benzoylmethyl, cyclohexyl or adamantyl group. Compounds in which X represents a nitromethyl, isopropyl, methoxycarbonylethyl, ethoxycarbonylmethyl, di(ethoxycarbonyl)methyl or benzoylmethyl group are especially preferred.

In another preferred aspect, X represents a $C_{6-18}$ aryl or 5- to 18- membered heteroaryl group, each group being optionally substituted by one or more substituents selected from the group consisting of halogen atoms, $C_{1-4}$ alkyl, $C_{-4}$ haloalky, $C_{1-4}$ alkoxy, di($C_{1-4}$alkyl)amino, $C_{7-10}$ aralkyl and heterocyclic groups. Preferably, X represents a $C_{6-10}$ aryl group optionally substituted by one or more substituents selected from the group consisting of halogen atoms, $C_{1-4}$ alkyl, $C_{1-4}$ alkoxy, di($C_{1-4}$ alkyl)amino and heterocyclic groups.

In a particularly preferred sub-group of compounds, X represents a phenyl, chlorophenyl or bromophenyl group.

IN a further preferred aspect, X may represent a group —$NR^1R^2$ where $R^1$ and $R^2$ independently represent a $C_{1-6}$ alkyl, $C_{6-10}$ aryl or $C_{7-16}$ aralkyl group, or $R^1$ and $R^2$ together with the interjacent nitrogen atom represent a 3- to 14-membered heterocyclic group, each group being optionally substituted by one or more substituents selected from the group consisting of halogen atoms, $C_{1-4}$ alkyl, $C_{1-4}$ haloalkyl and $C_{1-6}$ alkoxycarbonyl groups. Preferably, X represents a group —NR$^1$R$^2$ where R$^1$ and R$^2$ independently represent a C$_{1-4}$ alkyl or C$_{7-10}$ aralkyl group, or R$^1$ and R$^2$ together with the interjacent nitrogen atom represent a 5- to 10- membered heterocyclic group, each group being optionally substituted by one or more substituents selected from the group consisting of halogen atoms, C$_{1-4}$ alkyl, C$_{1-4}$ haloalkyl and C$_{1-4}$ alkoxycarbonyl groups.

In a particularly preferred sub-group of compounds, X represents a dibenzylamino or indolinyl group.

The present invention also provides the use of a compound of the general formula I as defined above for the manufacture of a medicament for use as a cytotoxic agent.

A compound of the general formula I as defined above for use as an antitumour agent or for use in the treatment of cancer is also provided. In addition, the present invention provides the use of a compound of the general formula I as defined above for the manufacture of a medicament for use as an antitumour agent or for use in the treatment of cancer.

Some of the compounds of formula I are already known. specifically, artemisinin derivatives are known in which the oxygen atom at the 11-position has been replaced by a nitrogen atom to produce 11-azaartemisinin and N-substituted derivatives thereof. For instance, Torok and Ziffer (J.Med.Chem.,1995,38, 5045–5050) synthesised 11-azaartemisinin and derivatives thereof in which the 11-nitrogen atom is substituted by a methyl, isobutyl, allyl, formylmethyl, benzyl, pyrid-2-ylmethyl, 2-thiophenemethyl or furfuryl group. These compounds were tested for in vitro activity against a chloroquine-resistant strain of Plasmodium falciparum and all compounds except the N-benzyl derivatives exhibited some activity. Mekonnen and Ziffer (Tetrahedron Letters,1997,38(5), 731–734) also synthesized 11-azaartemisinin and its N-allyl and N-formylmethyl derivatives and described the conversion of 11-azaartemisinin by a Michael addition reaction to derivatives in which the 11-nitrogen atom is substituted by a cyanoethyl, ethoxycarbonylethyl, methylcarbonylethyl, phenylsulphinylethyl, phenylsulphonylethyl or phenylsulphonatoethyl group. However, these derivatives were not tested for biological activity.

Artemisinin derivatives are also known in which the oxygen atom at C-10 has been replaced by an amine group. For instance, Yang et al (Biorg. Med. Chem. Lett., 1995, 5, 1791–1794) synthesised ten new artemisinin derivatives in which the oxygen atom at C-10 was replaced by a group —NHAr where Ar represents a phenyl, 3-chlorophenyl, 4-chlorophenyl, 3-bromophenyl, 4-bromophenyl, 4-iodophenyl, 4-methylphenyl, 4-methoxyphenyl, 3-carboxylphenyl or 4-carboxylphenyl group. These compounds were tested for in vivo activity against the K173 strain of Plasmodium berghei and found to be active.

Further artemisinin derivatives are also known in which one of the hydrogen atoms in the methyl group attached to the C-9 carbon atom in artemisinin, that is, one of the hydrogen atoms attached to the C-16 carbon atom, has been replaced by a sulphur-, nitrogen- or carbon-linked group. For instance, Paitayatat et al (J.Med.Chem.,1997,40, 633–638) synthesised, inter alia, two new artemisinin derivatives in which the C-16 carbon atom is substituted by a phenylthio or an imidazol-1-yl group and demonstrated that these compounds are active against Plasmodium falciparum. Avery et al (J.Med.Chem.,1996,39,4149–4155) synthesised artemisinin derivatives in which the C-16 carbon atom is substituted by a methyl, ethyl, n-propyl, benzyl or 4-chlorobenzyl group and the five corresponding 10-deoxo derivatives. Moreover, the activity of the five 10-deoxo derivatives against Plasmodium falciparum was also demonstrated. U.S. Pat. No. 5,216,175 also specifically discloses artemisinin derivatives in which the C-16 carbon atom of artemisinin is substituted by a methyl, isopropyl, n-butyl, n-dodecyl or benzyl group and demonstrates activity for these compounds against Plasmodium falciparum.

Artemisinin derivatives are also known in which the oxygen atom at C-10 forms part of a variety of ester groups. For instance, Li et al (Acta Pharmaceutical Sinica,1981,16, 429) synthesised, inter alia, ester derivatives of artemisinin in which the C-10 carbon atoms is substituted by a group of formula —O—CO—R$^A$ where R$^A$ represents a methyl, ethyl, n-propyl, isopropyl, n-butyl, isobutyl, phenyl 4-methylphenyl, 4-methoxyphenyl, 3,4,5-trimethoxyphenyl, benzyl or styryl group and evaluated these compounds for activity against a chloroquine-resistant strain of Plasmodium berghei. Cao et al (Nanjing Yaoxueyun Xuebao, 1982,1,53) also synthesised ester derivatives of artemisinin in which the C-10 carbon atom is substituted by a group of formula —O—CO—R$^B$ where R$^B$ represents an n-pentyl, n-hexyl, n-heptyl, n-octyl, n-nonyl, n-undecyl, 1-(propyl)butyl, 1-chloroethyl or t-butyl group and tested these compounds for suppressive antimalarial activity against Plasmodium berghei in mice.

Further artemisinin derivatives are known in which the oxygen atom at C-10 forms part of a variety of ether groups. For instance, Li et al (Acta Pharmaceutical Sinica,1981,16, 429) synthesised, inter alia, ether derivatives of artemisinin in which the C-10 carbon atoms is substituted by a group of formula —O—R$^B$ where R$^B$ represents a methyl, ethyl, n-propyl, isopropyl, n-butyl, isopentyl, tert-pentyl, n-octyl, 2-hydroxyethyl, 2-methoxyethyl, prop-2-enyl, 3-phenylprop-2-enyl, cyclopentyl, cyclohexyl, benzyl or 4-methoxybenzyl group and evaluated these compounds for activity against a chloroquine-resistant strain of Plasmodium berghei. Ramu and Baker (J.Med.Chem.1995, 38,1911–1921) synthesised glucuronide tri-ethanoyloxy ester derivatives of dihydroartemisinin and hydrolysed such derivatives to form the α- and β-dihydroartemisininglucuronides. The latter compounds exhibited in vitro activity against Plasmodium falciparum. Vishwakarma et al (J.Nat.Prod.,1992, 55(8),1142–1144) described a stereoselective synthesis of α-artelinic acid and its methyl ester and sodium salt and tested the acid for antimalarial activity against Plasmodium knowlesi in vivo. This article also refers to β-artelinic acid and its potassium salt. Lin et al (J.Med.Chem.,1990,33,2610–2614) referred to their earlier synthesis of β-artelinic acid and its sodium salt and the antimalarial activity of these compounds in mice infected with Plasmodium berghei.

U.S. Pat. No. 5,486,535 describes the activity of dehydroartemisinin and ether derivatives of artemisinin in which the C-10 carbon atom is substituted by a group of formula —O—R$^C$ where R$^C$ represents a methyl, ethyl, iso-propyl, iso-butyl or see-butyl group against Toxoplasma gondii.

U.S. Pat. No. 5,225,427 discloses certain 10-substituted ether derivatives of artemisinin in which the C-10 carbon atoms is substituted by a group of formula —O—R$^D$ where R$^D$ represents a 1-ethanoylethyl, 1,3-bis(isopropoxy)prop-2-yl, but-3-yn-2-yl, 2-methylbut-3-yn-2yl, 2-ethylbut-3-yn-2-yl, 2-(4-chlorophthalimido)ethyl, 3-(4-carboxylphenyl)-isoxazol-5-ylmethyl, 3-chloroisoxazol-5-ylmethyl or 3-bromoisoxazol-5-yl methyl group. The activity of all these compounds against Plasmodium berghei was demonstrated in vivo and the 2-ethylbut-3-yn-2-yl and 3-(4-carboxylphenyl)isoxazol-5-ylmethyl derivatives were also shown to possess antiamoebic activity against Entamoeba histolytica in vitro.

Certain compounds of the general formula I are novel and the invention therefore further provides a compound of the general formula I as defined above with the further provisos that (i) when X represents a group —NR$^1$R$^2$, then R$^1$ and R$^2$ together with the interjacent nitrogen atom do not represent an imidazol-1-yl group;

(ii) when Y represents a group —NR$^3$R$^4$ and R$^4$ represents a phenyl, 3-chlorophenyl, 4-chlorophenyl, 3-bromophenyl, 4-bromophenyl, 4-iodophenyl, 4-methylphenyl, 4-methoxyphenyl, 3-carboxylphenyl or 4-carboxylphenyl group, then R$^3$ is an optionally substituted alkyl group;

(iii) when Y represents a group —O—CO—R$^5$, R$^5$ does not represent a methyl, ethyl, propyl, butyl, n-pentyl, n-hexyl, n-heptyl, n-octyl, n-nonyl, n-undecyl, 1-(propyl)butyl, 1-chloroethyl, phenyl, 4-methylphenyl, 4-methoxyphenyl, 3,4,5-trimethoxyphenyl, benzyl or styryl group;

(iv) when Y represents a group —OR', R$^6$ does not represent an n-propyl, isopropyl, n-butyl, isobutyl, sec-butyl, iso-pentyl, tert-pentyl, n-octyl, 2-hydroxyethyl, 2-methoxyethyl, 1-ethanoylethyl, 1,3-bis(isopropoxy)prop-2-yl, prop-2-enyl, 3-phenylprop-2-enyl, but-3-yn-2-yl, 2-methylbut-3-yn-2-yl, 2-ethylbut-3-yn-2-yl, cyclopentyl, cyclohexyl, benzyl, 4-methoxybenzyl, 4-(methoxycarbonyl)benzyl, 4-carboxylphenyl, 4-(sodium carboxylato)benzyl, 4-(potassium carboxylato)benzyl, 3-chloroisoxazol-5-ylmethyl, 3-bromoisoxazol-5-ylmethyl, 3-(4-carboxylphenyl)isoxazol-5-ylmethyl, 2-(4-chlorophthalimide)ethyl, glucuronide or triethanoyloxyglucuronide group, (v) when Z is a group +50 NEC, R$^7$ does not represent a hydrogen atom or a methyl, isobutyl, allyl, formylmethyl, pyrid-2-ylmethyl, thenyl, furfuryl, benzyl, cyanoethyl, ethoxycarbonylethyl, ethanoylethyl, phenylsulphinylethyl, phenylsulphonylethyl or phenylsulphonatoethyl group;

(vi) when X represents an n-pentyl, n-tridecyl or 2-methylpropyl group, then Y represents a hydrogen or hydroxyl group; and (vii) when X represents a group —CHR$^8$R$^9$ where R$^8$ represents a hydrogen atom, then R$^9$ does not represent a methyl, ethyl, n-propyl, benzyl or 4-chlorobenzyl group.

It should also be appreciated that the compounds of general formula I are capable of existing as different geometric and optical isomers. The present invention thus includes both the individual isomers and mixtures of such isomers.

The present invention also provides processes for the preparation of novel compounds of the general formula I as defined in the ante-preceding paragraph. For instance, compounds of general formula I in which X represents a hydrogen atom, Y represents a halogen atom, an optionally substituted cycloalkyl, aryl, C-linked heteroaryl or heterocyclylalkyl group or a group —NR$^3$R$^4$, where R$^3$ and R$^4$ are as defined above, and Z represents an oxygen atom may be prepared by reacting a compound of the general formula II

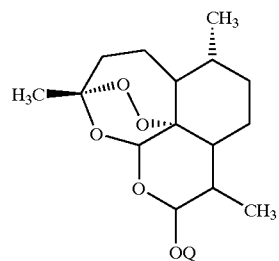

(II)

in which Q represents a hydrogen atom or trimethylsilyl group, with a suitable halogenating agent to form a compound of the general formula I in which Y represents a halogen atom; and, if desired, reacting the compound of general formula I thus formed either with a Grignard reagent of the general formula YMgHal where Y is an optionally substituted cycloalkyl, aryl, C-linked heteroaryl or heterocyclylalkyl group and Hal is a halogen atom to form a compound of general formula I in which Y represents an optionally substituted cycloalkyl, aryl, C-linked heteroaryl or heterocyclylalkyl group or with an amine of the general formula HNR$^3$R$^4$ where R$^3$ and R$^4$ are as defined above to form a compound of general formula I in which Y represents a group —NR$^3$R$^4$ where R$^3$ and R$^4$ are as defined above.

Suitable halogenating agents for forming compounds of the general formula I in which Y represents a halogen atom include diethylaminosulphur trifluoride, chlorotrimethylsilane, bromotrimethylsilane and iodotrimethylsilane. In particular, compounds of the general formula I in which Y represents a chlorine, bromine or iodine atom may be prepared by reacting a compound of the general formula II in which Q represents a trimethylsilyl group with a suitable chlorinating, brominating or iodinating agent respectively, such as chlorotrimethlysilane, bromotrimethylsilane or iodotrimethylsilane respectively. This reaction may be conveniently carried out in the presence of a solvent. Suitable solvents include halogenated hydrocarbons, especially chlorinated hydrocarbons, such as dichloromethane. Preferably, the reaction is carried out at a temperature of −30° C. to +10°, particularly −5° C. to +5° C., about 0° C. being especially preferred.

Compounds of the general formula I in which Y represents a fluorine atom may be conveniently prepared by reacting a compound of the general formula II in which Q represents a hydrogen atom with a suitable fluorinating agent, such as diethylaminosulphur trifluoride. This reaction may be conveniently carried out in the presence of a solvent, suitable solvents including halogenated hydrocarbons, especially chlorinated hydrocarbons, such as dichloromethane. Preferably, the reaction is carried out at −5° C. to room temperature, that is, −5 to +35° C., preferably 0 to 30° C. The reaction may also be carried out under an inert atmosphere, such as nitrogen.

Suitable Grignard reagents for forming compounds of the general formula I in which Y is an optionally substituted cycloalkyl, aryl, C-linked heteroaryl or heterocyclylalkyl group include compounds of the general formula YMgHal where Hal represents a chlorine, bromine or iodine atom. However, it is particularly preferred that Hal represents a bromine atom. The reaction of a compound of the general formula I in which Y represents a halogen, preferably a bromine, atom with a Grignard reagent may be conveniently carried out in the presence of a solvent. Suitable solvents include ethers, such as diethyl ether. Preferably, the reaction is carried out under an inert atmosphere, such as nitrogen, at a temperature of −5° C. to +5° C., 0° C. being especially preferred. This method produces a single pure isomer of the final product.

The reaction of an amine with a compound of the general formula I in which Y represents a halogen, preferably a bromine, atom to form a compound of the general formula I in which Y represents a group —NR³R⁴ where R³ and R⁴ are as defined above may be conveniently carried out in the presence of a solvent. Suitable solvents include halogenated hydrocarbons, especially chlorinated hydrocarbons, such as dichloromethane, and ethers, such as tetrahydrofuran. Preferably, the reaction is carried out at a temperature of −5° C. to +5° C., 0° C. being especially preferred.

When a compound of the general formula I in which Y represents a bromine atom is to be further reacted with a Grignard reagent or an amine to form a compound of the general formula I in which Y represents an optionally substituted cycloalkyl, aryl, C-linked heteroaryl or heterocyclylalkyl group or a group —NR³R⁴ where R³ and R⁴ are as defined above, it is preferred that the compound of the general formula I in which Y represents a bromine atom is generated in situ by reacting a compound of the general formula II in which Q represents a trimethylsilyl group with bromotrimethylsilane.

A compound of the general formula II in which Q represents a trimethylsilyl group may be prepared by reacting dihydroartemisinin, that is, the compound of general formula II in which Q represents a hydrogen atom, with chlorotrimethylsilane in the presence of a base, such as pyridine or triethylamine. Preferably, the reaction is carried out at room temperature, that is, 15 to 35° C., preferably 20 to 30° C.

Dihydroartemisinin, that is, the compound of general formula II in which Q represents a hydrogen atom, is a known compound and can be prepared by known processes.

Compounds of the general formula I in which Y represents an optionally substituted cycloalkyl, aryl, C-linked heteroaryl or heterocyclylalkyl group can also be prepared by reacting 9,10-anhydroartemisinin with a compound of the general formula Y—H, where Y is as defined above, in the presence of a suitable Lewis acid. This method produces a mixture of isomers in the final product.

Suitable Lewis acids include boron trifluoride diethyl etherate and trifluoromethanesulphonic acid. The reaction may be conveniently carried out in the presence of a solvent. Suitable solvents include halogenated hydrocarbons, especially chlorinated hydrocarbons, such as dichloromethane. Preferably, the reaction is carried out under an inert atmosphere, such as nitrogen, at room temperature, that is, 15 to 35° C., preferably 20 to 30° C.

9,10-Anhydroartemisinin may be conveniently prepared by reacting dihydroartemisinin with trifluoroacetic anhydride. The reaction may be conveniently carried out in the presence of a solvent, preferably a halogenated hydrocarbon, and especially a chlorinated hydrocarbon, such as dichloromethane. It is also preferred that the reaction is carried out in the presence of a base, such as pyridine or a derivative thereof, for example, dimethylaminopyridine. Preferably, the reaction is carried out under an inert atmosphere, such as nitrogen, at a temperature of −5° C. to +5° C., preferably 0° C., with the reaction mixture being subsequently allowed to warm to room temperature, that is, 15 to 35° C., preferably 20 to 30° C.

Compounds of the general formula I in which Y represents an optionally substituted aryl or C-linked heteroaryl group can also be prepared by reacting 10-trichloroacetimidoyl-10-deoxoartemisinin with a compound of the general formula Y—H, where Y is as defined above, in the presence of a suitable Lewis acid, such as boron trifluoride diethyl etherate. It is preferred that the 10-trichloroacetimidoyl-10-deoxoartemisinin is generated in situ by reacting a compound of the general formula II in which Q represents a hydrogen atom with trichloroacetonitrile in the presence of a suitable base, such as 1,8-diazabicyclo[5.4.0] undecane. Preferably, the reaction to form 10-trichloroacetimidoyl-10-deoxoartemisinin is carried out at room temperature, that is, 15 to 35° C., preferably 20 to 30° C. The reaction may be conveniently carried out in the presence of a solvent Suitable solvents include halogenated hydrocarbons; especially chlorinated hydrocarbons, such as dichloromethane. Preferably, the remainder of the reaction is carried out under an inert atmosphere, such as nitrogen. Preferably, the remainder of the reaction is carried out at a temperature of −60 to −20° C., particularly −55 to −30° C., and especially −40 to −50° C.

Compounds of the general formula I in which Y represents an optionally substituted aryl or C-linked heteroaryl group can also be prepared by reacting a 10-acyloxyartemisinin compound in which the acyloxy group is of formula A(C=O)—O—, where A represents an optionally substituted alkyl, cycloalkyl, aryl, aralkyl, heterocyclic or polycyclic group, with a compound of the general formula Y—H, where Y is as defined above, in the presence of a suitable Lewis acid. Suitable Lewis acids include boron trifluoride diethyl etherate, tin(IV) chloride, copper(II)-trifluoromethanesulfonate and trifluoromethanesulphonic acid. It is preferred that the Lewis acid is boron trifluoride diethyl etherate.

When A represents an optionally substituted alkyl group, unless otherwise specified, this may be linear or branched and may contain up to 12, preferably up to 6, and especially up to 4 carbon atoms. Preferred alkyl groups are methyl, ethyl, propyl and butyl.

When A represents an optionally substituted aryl group, this may be any aromatic hydrocarbon group and may contain from 6 to 24, preferably 6 to 18, more preferably 6 to 16, and especially 6 to 14, carbon atoms. Preferred aryl groups include phenyl, naphthyl, anthryl, phenanthryl and pyryl groups, especially phenyl, naphthyl and anthryl groups. When an aryl moiety forms part of another group, for example the aryl moiety of an aralkyl group, it is preferred that it is a phenyl, naphthyl, anthryl, phenanthryl or pyryl, especially a phenyl or naphthyl, and particularly a phenyl, moiety.

When A represents an optionally substituted aralkyl group, this may be any alkyl group substituted by an aryl group. A preferred aralkyl group contains from 7 to 30, particularly 7 to 24, more particularly 7 to 18, and especially 7 to 10, carbon atoms, particularly preferred aralkyl groups being benzyl, naphthylmethyl, anthrylmethyl, phenanthrylmethyl and pyrylmethyl groups, a benzyl group being especially preferred.

When A represents an optionally substituted cycloalkyl group, this may be any saturated or partially unsaturated cyclic hydrocarbon group and may contain from 3 to 12, preferably 3 to 8, and especially 3 to 6, carbon atoms. Preferred cycloalkyl groups are cyclopropyl, cyclopentyl and cyclohexyl groups.

When A represents an optionally substituted polycyclic group, this may be any saturated or partially unsaturated hydrocarbon group which contains more than one ring system. Such ring systems may be "fused", that is, adjacent rings have two adjacent carbon atoms in common, "bridged", that is, the rings are defined by at least two common carbon atoms (bridgeheads) and at least three acyclic chains (bridges) connecting the common carbon atoms, or "spiro" compounds, that is, adjacent rings are linked by a single common carbon atom. It is also envisaged that a polycyclic group may contain more than one of these types of ring system. Polycyclic groups preferably contain from 4 to 30, particularly 4 to 26, and especially 6 to 18, carbon atoms. Bicyclic, tricyclic and tetracyclic groups are particularly preferred. Preferred bicyclic groups contain from 4 to 14, especially 6 to 10, carbon atoms. Preferred tricyclic groups contain from 5 to 20, especially 6 to 14, carbon atoms with anthraquinone groups being especially preferred. Preferred tetracyclic groups contain from 6 to 26, especially 6 to 18, carbon atoms.

Optional substituents for the substituent A may be any of those previously identified as suitable in this respect.

The reaction may be conveniently carried out in the presence of a solvent. Suitable solvents include halogenated hydrocarbons, especially chlorinated hydrocarbons, such as dichloromethane. Preferably, the reaction is carried out under an inert atmosphere, such as nitrogen. Preferably, the reaction is carried out at a temperature of −60 to −20° C., particulariy −55 to −30° C., and especially −40 to −50° C.

Compounds of formula I in which Y represents a substituted aryl group where at least one of the substituents is a hydroxyl group can also be prepared by rearrangement of the corresponding C-10 ether linked artemisinin derivative so that the oxygen atom of the ether link becomes the oxygen atom of the hydroxyl group in the substituted aryl group of the desired product. Such a rearrangement can be effected by reacting the corresponding C-10 ether linked artemisinin derivative with a Lewis acid, such as a boron trifluoride diethyl etherate. The reaction is conveniently carried out in the presence of a solvent such as dichloromethane at a temperature of −5° C. to 5° C., preferably 0° C.

Certain compounds of the general formula I may also be prepared by conversion of another compound of general formula I. For instance, 10-(4-vinylphenyl) dihydroartemisinin may be converted to 10-(4-carboxylphenyl) dihydroartemisinin by reaction with an oxidising agent, such as potassium permanganate. Also, compounds of general formula I which contain a heterocyclic moiety having at least one sulphur atom in the ring system may be oxidised to form compounds of general formula I in which the or each sulphur atom has been converted to a sulphinyl or sulphonyl group by reaction with a suitable oxidising agent. Suitable oxidising agents include 4-methylmorpholine N-oxide (NMO), tetrapropylammonium perruthenate (TPAP) and mixtures thereof. The reaction may be conveniently carried out in the presence of a solvent, suitable solvents including halogenated hydrocarbons, especially chlorinated hydrocarbons, such as dichloromethane. Preferably, the reaction is carried out at room temperature, that is, 15 to 35° C., preferably 20 to 30° C. The reaction may also be carried out under an inert atmosphere, such as nitrogen.

Compounds of general formula I in which x represents a hydrogen atom, Y represents a group —O—CO—$R^5$, where $R^5$ is as defined above, and Z represents an oxygen atom may be prepared by reacting dihydroartemisinin with a compound of the general formula $R^5$—CO—W where W is a halogen atom or hydroxyl group or a group —O—CO—$R^5$ where $R^5$ is as defined above. When W is a halogen atom, it is preferred that the halogen atom is a chlorine atom.

The reaction of dihydroartemisinin with an acid chloride or acid anhydride, that is, compounds of formula $R^5$—CO—W in which W represents a chlorine atom or a group —O—CO—$R^5$ respectively, may be conveniently carried out in the presence of a solvent. Suitable solvents include halogenated hydrocarbons, particularly chlorinated hydrocarbons, such as dichloromethane. The reactions may also be carried out in the presence of a base, such as 4-(N,N-dimethylamino)pyridine, under an inert atmosphere, for instance, under nitrogen. Preferably, the reaction is carried out at a temperature of −5° C. to room temperature. Ideally, the reagents are initially mixed together at 0° C. and the reaction mixture is then allowed to warm to room temperature, that is, 15 to 35° C., preferably 20 to 30° C.

The reaction of dihydroartemisinin with a carboxylic acid, that is a compound of formula $R^5$—CO—W in which W represents a hydroxyl group, may be conveniently carried out in the presence of a suitable solvent. Suitable solvents include ethers, particularly cyclic ethers, such as tetrahydrofuran. The reaction may also be carried out in the presence of a suitable condensing agent which acts to activate the hydroxyl group of the carboxylic acid for displacement by the hydroxyl group of dihydroartemisinin. A suitable condensing agent is a combination of triphenylphosphine and diethyl azodicarboxylate. The reaction may be carried out under an inert atmosphere, for instance, under nitrogen. Preferably, the reaction is carried out at a temperature of −5° C. to room temperature, preferably 0° C. to room temperature. Ideally, the reagents are initially mixed together at 0° C. and the reaction mixture is then allowed to warm to room temperature, that is, 15 to 35° C., preferably 20 to 35° C.

Alternatively, the reaction of dihydroartemisinin with a carboxylic acid as defined above may be conveniently carried out in the presence of a halogenated hydrocarbon solvent, particularly a chlorinated hydrocarbon, such as dichloromethane. The reaction may also be carried out in the presence of dicyclohexylcarbodiimide under an inert atmosphere such as a nitrogen atmosphere. Preferably, the reaction is carried out at a temperature of −5 to +5° C., particularly about 0° C.

The acid chlorides, carboxylic acids and acid anhydrides of formula $R^5$—CO—W, where $R^5$ and W are as defined above, are all known compounds or can be prepared by processes analogous to known processes.

Compounds of general formula I in which X represents a hydrogen atom, Y represents a group —$OR^6$, where $R^6$ is as defined above, and Z represents an oxygen atom may be prepared by reacting dihydroartemisinin with a compound of the general formula $R^4$—OH where $R^6$ is as defined above.

The reaction of dihyaroartemisinin with an alcohol of formula $R^6$—OH as defined above may be conveniently carried out in the presence of a solvent. Suitable solvents include ethers, especially aliphatic ethers, such as diethyl ether. The reaction may also be carried out in the presence of a Lewis acid, such as boron trifluoride diethyl etherate, under an inert atmosphere, for instance, under nitrogen. Preferably, the reaction is carried out at room temperature, that is, 15 to 35° C., preferably 20 to 30° C.

The reaction of dihydroartemisinin with an alcohol of formula R-OH as defined above may also be conveniently carried out in the presence of a cyclic ether solvent such as tetranydroturan. In this case, the reaction may also be carried out in the presence of triphenylphosphine and diethyl azodicarboxylate under an inert atmosphere, for instance, under nitrogen. Preferably, the reaction is carried out at a temperature of −5° C. to room temperature, preferably 0° C. to room temperature. Ideally, the reagents are initially mixed together at 0° C. and the reaction mixture is then allowed to warm to room temperature, that is, 15 to 35° C., preferably 20 to 35° C.

In some circumstances, it may be necessary to protect certain groups of the dihydroartemisinin and/or alcohol starting materials with a protecting group to reduce the likelihood of undesirable side reactions. Suitable protecting groups include trimethylsilyl groups. In such cases, the reaction is preferably carried out in a halogenated hydrocarbon solvent, particularly a chlorinated hydrocarbon, such as dichloromethane. Preferably, the reaction is carried out in the presence of a catalytic amount of trimethylsilyl trifluoromethanesulphonate (TMSOTf) solution under an inert atmosphere, such as a nitrogen atmosphere. Preferably, the reaction is carried out at a temperature of −70 to 80° C., especially about −78° C. Alternatively, this reaction may be carried out at a temperature of −5 to +5° C, especially about 0° C., if it is desired to increase the quantity of one of the isomers, usually the β-anomer, and to reduce the quantity of the side products obtained. The trimethylsilyl protected starting materials may be prepared by reacting the dihydroartemisinin and/or alcohol with a halotrimethylsilane, such as chlorotrimethylsilane, in the presence of a base, such as pyridine or triethylamine. Preferably, the reaction is carried out at room temperature, that is, 15 to 35° C., preferably 20 to 30° C.

Alternatively, if it is desired to increase the quantity of the other isomer, usually the α-anomer, the reaction of dihydroartemisinin with an alcohol of formula $R^6$—OH as defined above may be conveniently carried out in the presence of a halogenated hydrocarbon solvent, particularly a chlorinated hydrocarbon, such as dichloromethane, in the absence of any protecting groups. The reaction is preferably carried out under an inert atmosphere, such as a nitrogen atmosphere. Preferably, the reaction is carried out at a temperature of −30 to −10° C., particularly −25 to −15° C.

The alcohols of formula $R^6$—OH, where $R^6$ is as defined above, are all known compounds or can be prepared by processes analogous to known processes.

Compounds of general formula I in which X represents a hydrogen atom, Y represents an oxo group and Z represents a group +50 NR', where $R^7$ is as defined above, may be prepared by reacting artemisinin with a compound of the general formula $R^7NH_2$ where $R^7$ is as defined above.

The reaction may be conveniently carried out in the presence of a solvent. Suitable solvents include lower alcohols, especially a $C_1$–$C_6$, alcohol, such as methanol, and halogenated hydrocarbons, especially a chlorinated hydrocarbon such as dichloromethane. The reaction is preferably carried out under an inert atmosphere, such as a nitrogen atmosphere. Preferably, the reaction is carried out at a temperature of −5 to +5° C., especially about 0° C. It may also be advantageous to add p-toluene sulphonic acid during the course of the reaction to ensure that any intermediate products are converted into the final cyclised lactam of formula I. Also, in some cases, it may be necessary to utilise an amine of formula $R^7NH_2$ which has been freshly distilled before the reaction in order to ensure that reaction occurs.

Alternatively, certain compounds of general formula I in which $R^7$ represents, a group —$CH_2H_2R^{10}$, where $R^{10}$ represents an electron-withdrawing group, may be prepared in a Michael addition reaction by reacting 11-azaartemisinin with a compound of the general formula $CH_2+50$ CH—$R^{10}$, where $R^{10}$ is as defined above. Preferably, the electron-withdrawing group is a nitro, cyano, formyl, alkanoyl, alkoxycarbonyl, alkylsulphinyl, alkylsulphinyl, alkylsulphonato, arylsulphinyl, arylsulphonyl or arylsulphonato group. It is also preferred that the reaction is carried out in the presence of a base, such as sodium hydroxide, and in the presence of a solvent, such as tetrahydrofuran.

The 11-azaartemisinin starting material may be prepared by reacting artemisinin with ammonia using the first process of the invention described above.

Compounds of general formula I in which X represents a group —$NR^1R^2$, —$CHR^8R^9$ or Ar, where $R^1$, $R^3$ $R^8$, $R^9$ and Ar are as defined above, Y represents an oxo group and Z represents an oxygen atom may be prepared by reacting artemisitene of the formula III

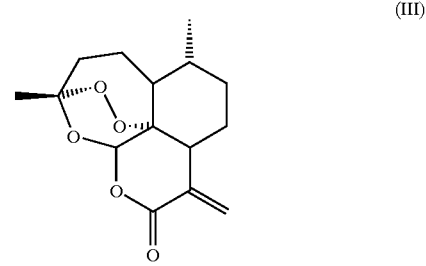

(III)

with a compound of the general formula MNu where M is a hydrogen or an alkali metal atom or a group —LHal, where L is an alkaline earth metal atom and Hal is a halogen atom, and Nu is a nucleophilic group of formula —$NR^1R^2$, —$CHR^{8'}R^{9'}$ or Ar where $R^1$, $R^2$ and Ar are as defined above, $R^{8'}$ represents a hydrogen atom or an optionally substituted alkoxycarbonyl group and $R^{9'}$ represents a nitro group or an optionally substituted alkanoyl, aroyl, alkoxycarbonyl or aryloxycarbonyl group. The alkali metal atom may be a lithium, sodium or potassium atom. However, it is particularly preferred that the alkali metal atom is a sodium or lithium, especially a lithium, atom. The alkaline earth metal atom L is preferably magnesium and the halogen atom Hal is preferably a chlorine, bromine or iodine atom.

It is especially preferred that compounds in which X represents a group —$NR^1R^2$ are prepared by reacting artemisitene with a metallated secondary amine of formula MNu where M is a lithium atom or a group —MgHal where Hal is as defined above and Nu is a nucleophilic group of formula —$NR^1R^2$ as defined above This reaction may be conveniently carried out in the presence of a suitable solvent. Suitable solvents include ethers, especially cyclic ethers, such a tetrahydrofuran. Preferably, the reaction is carried out at a temperature of −80 to −60° C., particularly −80 to −70° C., and especially −78° C.

The metallated secondary amine may be conveniently prepared by reacting a secondary amine of formula $HNR^1R^2$, where $R^1$ and $R^2$ are as first defined above, with a suitable lithiating agent or Grignard reagent. Suitable lithiating agents include n-, sec- or tert-butyllithium or a similar alkyllithium reagent. Suitable Grignard reagents include methyl or ethyl magnesium bromide or iodide. Preferably, the reaction is carried out in the presence of a suitable solvent, particularly an ether solvent such as tetrahydrofuran or diethyl ether, at a temperature of 0° C. or below, usually about −78° C.

Compounds of the general formula I in which Z represents an oxygen atom, Y represents an oxo group and X represents a group —$CHR^8R^{9'}$ where $R^{8'}$ and $R^{9'}$ are as defined above, may be conveniently prepared by reacting artemisitene with a lithiated acetyl reagent of formula MNu where M is a lithium atom and Nu is a nucleophilic group of formula —$CHR^8R^{9'}$ as defined above. This reaction may be conveniently carried out in the presence of a suitable solvent. Suitable solvents include ethers, especially cyclic ethers, such as tetrahydrofuran. Preferably, the reaction is carried out at a temperature of −80 to −60° C., particularly −80 to −70° C., and especially −78° C.

The lithiated acetyl reagent may be conveniently prepared by reacting an acetyl compound of formula $CH_2R^{8'R9'}$, where $R^{8'}$ and $R^{9'}$ are as defined above, with a suitable lithiating agent. Suitable lithiating agents for this reaction include lithium diisopropylamide or a similar lithium dialkylamide base or lithium hexamethyldisilazide. Preferably, the reaction is carried out in the presence of a suitable solvent, particularly an ether solvent such as tetrahydrofuran or diethyl ether, at a temperature of 0° C. or below, usually about −78° C.

Alternatively, compounds of the general formula I in which Y represents an oxo group and X represents a group —$CHR^{8'}R^{9'}$ where $R^{9'}$ and $R^{9'}$ are as defined above, may be conveniently prepared by reacting artemisitene with a reagent of formula MNu where M is a sodium atom and Nu is a nucleophilic group of formula —$CHR^{8'}R^{9'}$ as defined above. This reaction may be conveniently carried out under an inert atmosphere, such as nitrogen, in the presence of a suitable solvent. Suitable solvents include ethers, especially cyclic ethers, such as tetrahydrofuran. Preferably, the reaction is carried out at a temperature of −5 to +5° C., especially about 0° C.

The reagent of formula MNu where M is a sodium atom and Nu is a nucleophilic group of formula —$CHR^{8'}R^{9'}$ as defined above may be conveniently prepared by reacting, for instance, sodium hydride with a compound of formula $CH_2R^{8'}R^{9'}$, where $R^{8'}$ and $R^{9'}$ are as defined above.

Compounds of the general formula I in which Z represents an oxygen atom, Y represents an oxo group and X represents a group —$CHR^{8'}R^{9'}$ where $R^{8'}$ and $R^{9'}$ are as defined above, may also be conveniently prepared by reacting artemisitene with a reagent of formula MNu where M is a hydrogen atom and Nu is a nucleophilic group of formula —$CHR^{8'}R^{9'}$ as defined above. This reaction may be conveniently carried out in the presence of a suitable solvent. Suitable solvents include ethers, especially cyclic ethers, such as tetrahydrofuran. Preferably, the reaction is carried out in the presence of tris(dimethylamino)sulphur (trimethylsilyl)difluoride (TASF) and it is preferred that this stage of the reaction is carried out at a temperature of 0° C. or below, usually about −78° C. It may also be advantageous, or in some cases necessary, subsequently to add glacial acetic acid to the reaction mixture. This stage of the reaction, if included, may be carried out at room temperature, that is, 15 to 35° C., preferably 20 to 30° C.

In some cases, it may be advantageous or necessary to use a silylated form of the reagent of formula MNu as defined above either to protect a functional group of the reagent during reaction or to stabilise the intermediate carbanion formed during the reaction. Suitable silylated forms of the reagent of formula MNu where M is as defined-above and Nu is a nucleophilic group of formula —$CHR^{8'}R^{9'}$ as defined above include compounds in which $R'$ and $R^{9'}$ or a portion thereof has been replaced by a trimethylsilyl group. Such compounds can be prepared by reacting a suitable compound of formula MNu as defined above with a halotrimethylsilane, such as chlorotrimethylsilane or bromotrimethylsilane.

Compounds of the general formula I in which W represents an oxo group and X represents a group Ar, where Ar is as defined above, maybe conveniently prepared by reacting artemisitene with a reagent of formula QNu where Q is an alkali metal atom, preferably lithium, or a group —MHal where M is an alkaline earth metal atom, preferably magnesium, and Hal is a halogen atom. This reaction may be conveniently carried out in the presence of a catalytic amount of a copper (I) salt, such as copper (I) iodide, in a suitable solvent. Suitable solvents include ethers, such as diethyl ether and, especially, cyclic ethers, such as tetrahydrofuran. Preferably, the reaction is carried out at a temperature at or below 0° C., preferably about −10° C. In this reaction, the metallated Ar group adds to the exocyclic double bond of artemisitene to form an enolate, which is converted into the desired product of formula I when the reaction mixture is treated with a proton source, such as aqueous ammonium chloride.

The aryl Grignard or aryllithium reagent of formula QNu as defined above may be conveniently prepared by treating a compound of general formula ArHal, where Ar and Hal are as defined above, with either magnesium or lithium metal. Preferably, the reaction is carried out in the presence of a suitable solvent, preferably an ether solvent, such as diethyl ether, tetrahydrofuran or dimethoxyethane.

Suitable reducing agents for forming compounds of the general formula I in which $Z'$ represents an oxygen atom, Y represents a hydrogen atom and X represents a group where $R^{8'}$ and $R^{9'}$ are as defined above, include sodium borchydride in the presence of boron trifluoride diethyl etherate, diisobutylaluminium hydride, similar Lewis acidic metal hydrides and triethylsilane. The reduction reaction may be conveniently carried out in the presence of a suitable solvent. Suitable solvents include ethers, especially cyclic ethers, such as tetrahydrofuran. Preferably, the reaction is carried out at a temperature of −5° C. to the reflux temperature of the reaction mixture, especially 0° C. to reflux temperature. Ideally, the reagents are initially mixed together at 0° C. and the reaction mixture is then subsequently heated at reflux temperature.

Depending on the reducing agent and reaction conditions selected, the carbonyl group in the $R^{9'}$ moiety of compounds of the general formula I in which Z represents an oxygen atom, Y represents an oxo group and X represents a group —$CHR^{8'}R^{9'}$, where $R^{8'}$ and $R^{9'}$ are as defined above, may also be reduced to give compounds of the general formula I in which Z represents an oxygen atom, Y represents a hydrogen atom and X represents a group —$CHR^{8'}R^{9'}$ where $R^{8'}$ is as defined above and $R^{9'}$ is a group —$CH_2R^E$ where $R^E$ is an alkyl, aryl, alkoxy or aryloxy group.

Artemisitene may be prepared by reacting 10-hydroperoxy-10-dihydroartemisitene (9-hydroperoxyartemisitene) of formula

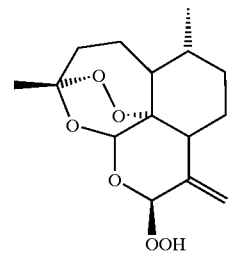

with acetic anhydride in the presence of a base, preferably pyridine. Preferably, the reaction is carried out at room temperature, that is, 15 to 35° C., preferably 20 to 30° C.

10-Hydroperoxy-10-dihydroartemisitene (9-hydroperoxyartemisitene) may be prepared by reacting 9,10-arhydro-10-deoxoartemisinin (9,10-anhydrodehydroartemisinin) of formula

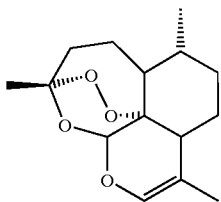

with oxygen in the presence of a solvent, preferably a halogenated hydrocarbon, such as dichloromethane: A photosensitiser, such as methylene blue, is preferably included in the reaction mixture to convert groud state (triplet) oxygen into excited state (singlet) oxygen under irradiation from a light source. The active agent which converts the 9,10-anhydro-10-deoxoartemisinin (9,10-anhydrodehydroartemieninin) into 10-hydroperoxy-10-dihydroartemisitene (9-hydroperoxyartemisitene) is therefore singlet oxygen.

9,10-Anhydro-10-deoxoartemisinin(9,10-anhy (irodehydroartemisinin) may be prepared by reacting dihydroartemisinin with a dehydrating agent, such as boron trifluoride diethyl etherate, preferably in the presence of a solvent, especially an ether solvent, such as diethyl ether. Ideally, the reaction is, carried out at room temperature, that is, 15 to 35° C., preferably 20 to 30° C.

9,10-Anhydro-10-deoxoartemisinin (9,10-anhydroartemisinin) may also be conveniently prepared by reacting dihydroartemisinin with trifluoroacetic anhydride. The reaction may be conveniently carried out in the presence of a solvent, preferably a halogenated hydrocarbon, and especially a chlorinated hydrocarbon, such as dichloromethane. It is also preferred that the reaction is carried out in the presence of a base, such as pyridine or a derivative thereof, for example, dimethylamino-pyridine. Preferably, the reaction is carried out under an inert atmosphere, such as nitrogen, at a temperature of −5° C. to +5° C., preferably 0° C., with the reaction mixture being subsequently allowed to warm to room temperature, that is, 15 to 35° C., preferably 20 to 30° C.

The amines of formula $HNR^1R^2$, acetyl compounds of formula $CH_2R^{8'}R^{9'}$ and aryl halide compounds of formula ArHal, where $R^1$, $R^2$, $R^{8'}$, $R^{9'}$ and Ar are as defined above, are all known compounds or can be prepared by processes analogous to known processes.

Compounds of the general formula I in which X represents a group —$CHR^8R^9$, where $R^8$ and $R^9$ are as first defined above, can also be prepared by reacting artemisitene with a compound of the general formula $TCHR^8R^9$, where T represents a halogen atom and $R^8$ and $R^9$ are as defined above, to form a compound of formula I in which Y represents an oxo group and X is as defined above; and, if desired, reacting the compound of formula I thus formed with a suitable reducing agent to form a compound of formula I in which Y represents a hydrogen atom and X is as defined above.

Preferred compounds of formula $TCHR^8R^9$ are those in which T represents a chlorine or bromine, especially a bromine, atom. It is also preferred that this reaction is carried out in the presence of a suitable solvent. Suitable solvents include ethers, such as 1,2-dimethoxyethane. Preferably, the reaction is carried out in the presence of catalytic amounts of an initiator, such as 2,2'-azobisisobutyronitrile (AIBN, also known as 2,2'-azobis[2-methylpropane-nitrile]), in the presence of tri-n-butyltin hydride. In this context, AIBN converts tri-n-butyltin hydride into the tributyltin radical which abstracts halogen from the compound of formula $TCHR^8R^9$ to provide a carbon radical which adds to the exocyclic double bond of artemisitene. After addition, the resulting artemisinin radical is reduced by hydrogen atom transfer from the tri-n-butyltin hydride and the chain process is maintained by the tributyltin radical. It is also preferred that the reaction is carried out at a temperature of 60 to 100° C., particularly 70 to 90° C., and preferably 75 to 85° C.

Suitable reducing agents for forming compounds of the general formula I in which Y represents a hydrogen atom and X represents a group —$CHR^8R^9$, where $R^8$ and $R^9$ are as defined above, include sodium borohydride in the presence of boron trifluoride diethyl etherate, diisobutylaluminium hydride, similar Lewis acidic metal hydrides and triethylsilane. The reduction reaction may be conveniently carried out in the presence of a suitable solvent, suitable solvents including ethers, such as tetrahydroturan. Preferably, the reaction is carried out at a temperature of −5° C. to the reflux temperature of the reaction mixture, especially 0° C. to reflux temperature. Ideally, the reagents are initially mixed together at 0° C. and the reaction mixture is then subsequently heated at reflux temperature.

Artemisitene can be prepared as described above and compounds of formula $TCHR^8R^9$ are known compounds or can be prepared by processes analogous to known processes.

The invention also provides a pharmaceutical composition which comprises a carrier and, as active ingredient, a novel compound of the general formula I as defined above.

A pharmaceutically acceptable carrier may be any material with which the active ingredient is formulated to facilitate administration. A carrier may be a solid or a liquid, including a material which is normally gaseous but which has been compressed to form a liquid, and any of the carriers-normally used in formulating pharmaceutical compositions may be used. Preferably, compositions according to the invention contain 0.5 to 95% by weight of active ingredient.

The compounds of general formula I can be formulated as, for example, tablets, capsules, suppositories or solutions. These formulations can be produced by known methods using conventional solid carriers such as, for example, lactose, starch or talcum or liquid carriers such as, for example, water, fatty oils or liquid paraffins. Other carriers which may be used include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrins; pectins; synthetic polymers such as polyvinylpyrrolidone; polypeptide/protein or polysaccharide complexes such as gelatin-acacia complexes; sugars such as mannitol, dextrose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-Aspartic acid, L-glutamic acid, L-hydroxyproline, L-isoleucine, L-leucine and L-phenylalanine.

Auxiliary components such as tablet disintegrants, solubilisers, preservatives, antioxidants, surfactants, viscosity enhancers, colouring agents, flavouring agents, pH modifiers, sweeteners or taste-masking agents may also be incorporated into the composition. Suitable colouring agents include red, black and yellow iron oxides and FD & C dyes such as FD & C blue No. 2 and FD & C red No. 40 available from Ellis & Everard. Suitable flavouring agents include mint, rasberry, liquorice, orange, lemon, grapefruit, caramel, vanilla, cherry and grape flavours and combinations of these.

Suitable pH modifiers include citric acid, tartaric acid, phosphoric acid, hydrochloric acid and maleic acid. Suitable sweeteners include aspartame, acesulfame K and thaumatin. Suitable taste-masking agents include sodium bicarbonate, ion-exchange resins, cyclodextrin inclusion compounds, adsorbates or microencapsulated actives.

According to another aspect of the invention there is provided a compound of the general formula A—B in which A represents a ligand which is capable of binding to a nucleic acid and B is a group containing a trioxane moiety which is capable of acting as a source of a free radical which free radical is capable of chemically interacting with a nucleic acid.

Preferably, the free radical is an oxygen-centred or a carbon-centred free radical and the trioxane moiety acts as a controlled source of such free radicals. Typically, a free radical of this type is formed by a mechanism in accordance with or similar to the mechanisms set out in Scheme 1 or Scheme 2 above, that is, reduction of the peroxide bond by access to a one-electron reductant, such as Fe(II) or an organic reductant such as a thiol, or ring opening to provide hydroperoxide and then hydroxyl radical or, perferryl iron.

It is desirable that ligand A should be capable of aligning the trioxane moiety proximate to specified base sequences in DNA. The binding of ligand A to a nucleic acid may be accomplished by a variety of methods in order to achieve this aim. Thus, it is preferred that A represents a ligand which is capable of intercalating into a nucleic acid, binding to the minor groove of a nucleic acid or bonding to a deoxyribose or phosphate group of a nucleic acid. The bonding of the ligand A to a deoxyribose or phosphate group of a nucleic acid ideally takes place by means of hydrogen bonding.

In the case of ligands which act as intercalators, it is important that the trioxane moiety be attached to the intercalating group in a manner which does not affect its intercalation properties. Thus, the trioxane moiety must not interact chemically with the intercalating group upon activation of the peroxide moiety within the trioxane pharmacophore.

Typical ligands which are capable of binding to a nucleic acid include optionally substituted aromatic, polycyclic aromatic, glycoside and polypyrrole groups.

The group containing a trioxane moiety is preferably derived from artemisinin or an analogue thereof. However, it may also be derived from a synthetic trioxane.

In one preferred group of compounds, the compound of general formula A—B is a compound of the general formula IV

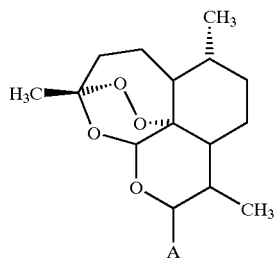

(IV)

or a salt thereof, in which A is as defined above.

Preferably, A represents an optionally substituted aryl or C-linked heteroaryl group or a group —NR$^3$R$^4$, —O—CO—R$^5$ or —OR$^6$; where R$^3$ represents a hydrogen atom or an optionally substituted alkyl group and R$^4$ represents an optionally substituted aryl or aralkyl group, or R$^3$ and R$^4$ together with the interjacent nitrogen atom represent an optionally substituted heterocyclic group; R$^5$ represents an optionally substituted aryl, aralkyl, heterocyclic or polycyclic group; and R$^6$ represents an optionally substituted aryl, aralkyl, heterocyclic or polycyclic group.

In one preferred aspect, A represents a $C_{6-18}$ aryl group or a 5- to 10-membered C-linked heteroaryl group, each group being optionally substituted by one or more substituents selected from the group consisting of halogen atoms, hydroxyl, $C_{1-4}$ alkyl, $C_{2-4}$ alkenyl, $C_{1-4}$ haloalkyl, $C_{1-4}$ alkoxy, $C_{1-4}$ haloalkoxy, amino, $C_{1-4}$ alkylamino, di($C_{1-4}$alkyl)amino and carboxyl groups.

In a particularly preferred sub-group of these compounds, A represents a phenyl, chlorophenyl, bromophenyl, trimethylphenyl, vinylphenyl, methoxyphenyl, dimethoxyphenyl, trimethoxyphenyl, carboxylphenyl, naphthyl, hydroxynaphthyl, anthryl or phenanthryl group. Compounds in which A represents a dimethoxyphenyl or trimethoxyphenyl group are especially preferred.

In another preferred aspect, A represents a group —NR$^3$R$^4$ where R$^3$ represents a hydrogen atom or a $C_{1-6}$ alkyl group and R$^4$ represents a $C_{6-10}$ aryl or $C_{7-16}$ aralkyl group, or R$^3$ and R$^4$ together with the interjacent nitrogen atom represent a 5- to 10-membered heterocyclic group, each group being optionally substituted by one or more substituents selected from the group consisting of halogen atoms, $C_{1-4}$ alkyl, $C_{1-4}$ haloalkyl, $C_{1-6}$ alkoxycarbonyl and phenyl groups.

In a particularly preferred sub-group of these compounds, A represents a phenylamino, fluorophenylamino, chlorophenylamino, bromophenylamino, iodophenylamino, methoxycarbonylphenylamino, biphenylamino, benzylamino, fluorobenzylamino, bis(trifluoromethyl) benzylamino, morpholinyl, thiomorpholinyl, morpholinosulphonyl, indolinyl or tetrahydroisoquinolinyl group. Compounds in which A represents a phenylamino or fluorophenylamino group are especially preferred.

In a further preferred aspect, A represents a group —O—CO—R$^5$ where R$^5$ represents a $C_{6-18}$ aryl, 5- to 18-membered heterocyclic or $C_{4-26}$ polycyclic group, each group being optionally substituted by one or more substituents selected from the group consisting of halogen atoms, hydroxyl, $C_{1-4}$ alkyl, $C_{1-4}$ haloalkyl, $C_{1-4}$ alkoxy, $C_{1-4}$ haloalkoxy, oxo, carboxyl and carboxylato groups. More preferably, A represents a group —O—CO—R$^5$ where R$^5$ represents a $C_{6-14}$ aryl, 5- to 14-membered heterocyclic or $C_{6-14}$ polycyclic group, each group being optionally substituted by one or more substituents selected from the group consisting of halogen atoms, hydroxyl, $C_{1-4}$ alkyl, $C_{1-4}$ haloalkyl, oxo and carboxylato groups.

In a particularly preferred sub group of these compounds, A represents a group —O—CO—R$^5$ where R$^5$ represents a phenyl, hydroxynaphthyl, anthryl, anthraquinonyl, quinolinyl, isoquinolinyl, quinoxalinyl or acridinyl group.

In another preferred aspect, A represents a group —OR$^6$ where R$^6$ represents a $C_{6-24}$ aryl, $C_{7-30}$ aralkyl, 5- to 18-membered heterocyclic or $C_{4-26}$ polycyclic group, each group being optionally substituted by one or more substituents selected from the group consisting of halogen atoms, hydroxyl, $C_{1-8}$ alkyl, $C_{1-4}$ haloalkyl, $C_{1-4}$ alkoxy, $C_{1-4}$ haloalkoxy, carboxyl and $C_{1-4}$ alkoxycarbonyl groups. More preferably, A represents a group —OR$^6$ where R$^6$ represents a $C_{6-14}$ aryl, $C_{7-18}$ aralkyl, 5- to 14-membered heterocyclic or $C_{6-18}$ polycyclic group, each group being optionally substituted by one or more substituents selected from the group consisting of halogen atoms, $C_{1-4}$ alkyl, $C_{1-4}$ haloalkyl, $C_{1-4}$ alkoxy and $C_{1-4}$ haloalkoxy groups.

In a particularly preferred sub-group of these compounds, A represents a group —OR⁶ where R⁶ represents a phenyl, methoxyphenyl, naphthyl, benzyl, fluorobenzyl, naphthylmethyl, anthrylmethyl, phenanthrylmethyl, pyrylmethyl, quinolinyl, trifluoromethylquinolinyl or cholestenyl group. Compounds in which A represents a group —OR⁶ where R⁶ represents a naphthylmethyl group are especially preferred.

In another preferred group of compounds, the compound of general formula A-B is a compound of the general formula V

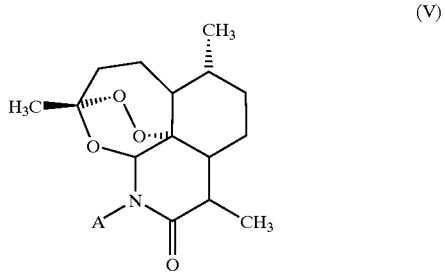

(V)

in which A is a ligand which is capable of binding to a nucleic acid.

Preferably, A represents a $C_{7-16}$ aralkyl or 5- to 10-membered-heterocyclic-$C_{1-6}$ alkyl group, each group being optionally substituted by one or more substituents selected from the group consisting of halogen atoms, cyano, nitro, $C_{1-4}$ haloalkyl, formyl, $C_{1-6}$ alkoxycarbonyl, $C_{1-6}$ alkanoyl, phenylsulphinyl, phenylsulphonyl and phenylsulphonato groups. More preferably, A represents a benzyl group optionally substituted by one or more halogen atoms or hydroxyl groups.

In a particularly preferred sub-group of these compounds, A represents a benzyl or fluorobenzyl group.

In a further preferred group of compounds, the compound of general formula A-B is a compound of the general formula VI

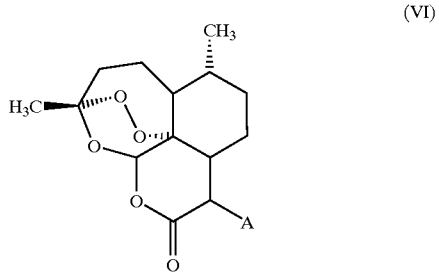

(VI)

in which A is a ligand which is capable of binding to a nucleic acid.

It is preferred that A represents a group —CH₂—NR¹R² where one of R¹ and R² represents an optionally substituted aryl or aralkyl group and the other of R¹ and R² represents an optionally substituted alkyl, cycloalkyl, aryl or aralkyl group, or R¹ and R² together with the interjacent nitrogen atom represent an optionally substituted heterocyclic group or an amino group derived from an optionally substituted amiono acid ester which contains an aromatic or heterocyclic moiety. Suitable amino acids in this respect include histidine, phenylalanine, tyrosine, tryptophan, proline and hydroxyproline.

Preferably, A represents a group —CH₂—NR¹R² where one of R¹ and R² represents a $C_{6-10}$ aryl or $C_{7-16}$ aralkyl group and the other of R¹ and R² represents a $C_{1-6}$ alkyl, $C_{6-10}$ aryl or $C_{7-16}$ aralkyl group, or R¹ or R² together with the interjacent nitrogen atom represent a 3- to 14-membered heterocyclic group, each group being optionally substituted by one or more substituents selected from the group consisting of halogen atoms, $C_{1-4}$ alkyl, $C_{1-4}$ haloalkyl and $C_{1-6}$ alkoxycarbonyl groups. More preferably, A represents a group —CH₂—NR¹R² where one or R¹ and R² represents a $C_{7-10}$ aralkyl group and the other of R¹ and R⁴ represents a $C_{1-4}$ alkyl or $C_{7-10}$ aralkyl group,, or R¹ and R⁴ together with the interjacent nitrogen atom represent a 5- to 10-membered heterocyclic group, each group being optionally substituted by one or more substituents selected from the group consisting of halogen atoms, $C_{1-4}$ alkyl, $C_{1-4}$ haloalkyl and $C_{1-4}$ alkoxycarbonyl groups.

In a particularly preferred sub-group of these compounds, A represents a dibenzylaminomethyl or indolinylmethyl group.

In formula VI, A may also represent a group —CH₂—Ar where Ar is as defined above.

In another preferred group of compounds, the compound of general formula A-B is a compound of the general formula VII

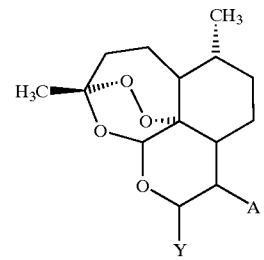

in which A is a ligand which is capable of binding to a nucleic acid and Y is a hydrogen atom or an oxo or hydroxyl group.

Preferably, A represents a group —CH₂—CR⁸R⁹ where R⁸ represents a hydrogen atom or an optionally substituted alkyl, alkenyl, alkynyl, aryl or alkoxycarbonyl group; and R⁹ represents a nitro group or an optionally substituted alkyl, alkenyl, alkynyl, aryl, alkanoyl, aroyl, alkoxycarbonyl or aryloxycarbonyl group, with the proviso that at least one or R⁸ and R⁹ represents or contains an aromatic moiety, or R⁸ and R⁹ together with the interjacent carbon atom represent an optionally substituted polycyclic group containing an aromatic moiety; with the proviso that, when R⁸ represents a hydrogen atom and R⁹ represents a benzyl or 4-chlorobenzyl group, then Y represents a hydroxyl group. More preferably, A represents a group —CH₂—CR⁸R⁹ where R⁸ represents a hydrogen atom or a $C_{1-6}$ alkyl or $C_{1-6}$ alkoxycarbonyl group and R⁹ represents a $C_{7-11}$ aroyl or $C_{6-10}$ aryloxycarbonyl group, or R⁸ and R⁹ together with the interjacent carbon atom represent a $C_{4-26}$ polycyclic group containing an aromatic moiety, each group being optionally substituted by one or more substituents selected from the group consisting of halogen atoms, hydroxyl, $C_{1-4}$ alkyl, $C_{1-4}$ haloalkyl, $C_{1-4}$ alkoxy and $C_{1-4}$ haloalkoxy groups.

In formula VII, A may also represent a group —CH₂—Ar where Ar is as defined above.

It should also be appreciated that many of the compounds of the general formula A-B are capable of existing as different geometric and optical isomers. The present invention thus includes both the individual isomers and mixtures of such isomers.

Compounds of general formula A-B as defined above may be prepared by the processes described earlier in this specification or by processes analogous to such processes.

At present, drug research relies to a large extent on ad hoc processes involving the uncovering of new chemical entities from nature and post-hoc establishment of mode of action, the ene-diyne antibiotics discussed earlier being good examples in this respect. Often a single drug candidate compound will be isolated from a natural source and structural variation must be carried out to modify undesirable properties. However, it is an advantage of the present invention that families of compounds can be easily prepared which are based on the trioxane pharmacophore and the biological activity of such compounds can be varied through variation in the nature of the binding group attached to the trioxane moiety thereby enabling different drug targets to be selected. Considerable structural variation in target compounds is possible through relatively straightforward structural variation in the ligand and trioxane moiety and this allows for fine tuning of biological activity. Moreover, since the starting materials are commercially available and the chemical transformations required to transform them into drug candidate compounds are relatively straightforward, the compounds are relatively accessible.

A further advantage of the compounds of the invention is that the compounds themselves provide a source of active free radicals and do not therefore require activation as in the case of other drugs, such as bleomycin. The utility of new drugs containing such a radical generating "warhead" is potentially enormous, particularly in the targeting of tumours. Moreover, since the compounds do not require activation, they have potential use against hypoxic cells, such as in solid tumours. It has also been shown that the compounds are more cytotoxic against rapidly replicating cells making them particularly attractive for use as antitumour agents. Moreover, many of the compounds have been found to damage DNA, particularly intracellular DNA.

The invention also provides a pharmaceutical composition which comprises a carrier and, as active ingredient, a compound of the general formula A-B as defined above. Such compositions may contain the same ingredients and be formulated in the same way as the compounds of general formula I described above.

Many of the compounds of formula A-B described above, especially those falling within the particularly preferred sub-groups of compounds, have been found to exhibit cytotoxic activity. Such compounds appear to act by selective destruction of DNA in tumour cells. The invention therefore further provides a compound of the general formula A-B as defined above for use as a cytotoxic agent, for use as an antitumour agent and/or for use in the treatment of cancer. The invention also provides the use of a compound of the general formula A-B as defined above for the manufacture of a medicament for use as a cytotoxic agent, for use as an antitumour agent and/or for the treatment of cancer.

The invention also provides a method for killing a cell which comprises exposing the cell to a compound of the general formula I or a compound of the general formula A-B as defined above. A method for treating cancer is also provided which comprises administering to an animal in need of such treatment a therapeutically effective amount of a compound of the general formula I or a compound of the general formula A-B as defined above. Preferably, the animal is a mammal, especially a human.

The invention is further illustrated by the following examples.

EXAMPLE 1

Preparation of 10β-fluoro-10-deoxodihydroartemisinin (Formula I: X=H; Y=F; Z=O; Formula IV: A=F)).

A solution of dihydroartemisinin (1.136 g, 4 mmol) in dichloromethane (24 ml) was cooled to 0° C. under nitrogen and diethylaminosulphur trifluoride (DAST) (0.6 ml, 4.8 mmol) was added. The reaction mixture was allowed to warm up to room temperature and then stirred under nitrogen for 24 hours. The yellow solution was cooled again to 0° C., $Na_2CO_3$ solution (5%, 20 ml) was added and the mixture was stirred for 2 hours at room temperature. After this the two phases were separated and the organic layer was washed with 1 molar HCl, 5% $NaHCO_3$ and water and dried over $MgSO_4$. Immediately after evaporating the solvent, the residue was purified twice by flash colum chromatography (10% ethyl acetate/hexane), followed by recrystallisation from hexane (289 mg, 50.5%); $^1H$ NMR (300 MHz, $CDCl_3$): δ ppm 0.97 (d, $J_{=6-Me,6}$=6.1 Hz, 3H, 6-$CH_3$), 1.00 (d, $J_{9-Me,9}$=7.4 Hz, 3H, 9-$CH_3$), 1.13–1.47 (m, 3H), 1.44 (s, 3H, 3-$CH_3$), 1.47–1.72 (m, 4H), 1.82–1.96 (m, 2H), 2.05 (ddd, J=14.6 Hz, J=4.9 Hz, J=3.0 Hz, 1H), 2.39 (td, J=13.5 Hz, J=4.0 Hz, 1H), 2.64 (dm, $J_{9,F}$=36.1 Hz, 1H, H-9), 5.60 (dd, J=10-F=54.4 Hz, $J_{10,9}$=2.4 Hz, 1H, H-10), 5.56 (d, J=1.83 Hz, 1H, H-12); $^{19}F$ NMR (300 MHz, $CDCl_3$): δ (ppm)=– 136.43 (dd, $J_{F,10}$=54.1 Hz, $J_{F,9}$=36.0 Hz); MS (CI): m/z (%)=304 [$M^+$+$NH_4^+$] (18), 286 [$M^+$], 284 [304-HF] (100), 267 (64), 256 (28), 239 (16), 221 (12), 163 (8), 52 (28).

EXAMPLE 2

Preparation of 10β-(phenyl)dihydroartemisinin (Formula I: X=H; Y=phenyl; Z=). Formula IV: A= phenyl)

(a) Preparation of 10-(trimethylsiloxy)dihydroartemisinin (Formula II: O=—Si($CH_3$)$_3$)

To a solution of dihydroartemisinin (1.51 g, 5.32 mmol) in pyridine (20 ml) at 0° C. under nitrogen was added dropwise chlorotrimethylsilane (5.20 ml, mmol). The mixture was stirred at room temperature for a further 1 hour and poured into ice-water mixture. The solution was extracted with diethyl ether (3×15 ml), dried ($MgSO_4$) and concentrated in vacuo. The residue was purified by flash chromatography ($SiO_2$: 5% ethyl acetate/hexanes) to give 10-(trimethylsiloxy)dihydroartemisinin as a white solid (1.47 g, 78%). $δ_H$ 5.49 (1H, s, H-12), 5.19 (1H, d, J=3.05 Hz, H-10), 2.52–2.62 (1H, m, H-9), 2.39 (1H, ddd, J=17.5, 13.4, 4.01 Hz), 2.04 (1H, ddd, J=14.5, 4.84, 3.05 Hz), 1.20–1.97 (9H, m), 1.45 (3H, s, H-14), 0.97 (3H, d, J=6.24 Hz, H-16), 0.87 (3H, d, J=7.29 Hz, H-15), 0.17 (9H, s, (C$\underline{H}_3$)$_3$Si).

(b) Preparation of 10-bromoartemisinin (Formula I: X=H; Y=Br; Z=O. Formula IV: A=Br).

A solution of 10-(trimethylsiloxy)dihydroartemisinin (372 mg, 1.04 mmol) prepared as described in (a) above in dichloromethane (5 ml) at 0° C. was treated dropwise with bromotrimethylsilane (140 μl, 1.06 mmol). The mixture was stirred at 0° C. for a further 30 minutes to produce 10-bromoartemisinin in situ.

(c) Preparation of 10β-(phenyl)dihydroartemisinin (Formula I: X=H; Y=phenyl; Z=O. Formula IV: A=phenyl).

The solution prepared in (b) above was concentrated in vacuo. The residue was dissolved in diethyl ether (5 ml). To this solution was added phenylmagnesium bromide (1.40 ml, 2.38 mmol, 1.7M) at 0° C. under nitrogen. The mixture was then stirred at 0° C. and then allowed to reach room temperature overnight. The solution was then quenched with saturated ammonium chloride solution, dried ($MgSO_4$) and concentrated in vacuo. The residue was purified by flash chromatography ($SiO_2$; 8% ethyl acetate/hexanes to give 10β-(phenyl)dihydroartemisinin (159 mg, 45%) as a white solid. Recrystallisation from ether/hexane mixture gave a colourless rectangular crystal. M.p. 122° C.; $[α]_D^{20}$ –36.0° (c 0.47/$CHCl_3$); $v_{max}$ (film) 2938, 2874, 1494, 1452, 1376, 1208, 1112, 1076, 1058, 1038, 1010, 954, 944, 904, 882, 852, 820, 740, 700; $\delta_H$ 7.19–7.34 (5H, m, Ar—H), 5.75 (1H, d, J=6.70 Hz, H-10), 5.60 (1H, s, H-12), 2.71–2.84 (1H, m, H-9), 2.31–2.42 (1H, m), 1.65–2.12 (5H, m), 1.28–1.60 (5H, m), 1.41 (3H, s, H-14), 1.01 (1H, d, J=5.77 Hz, H-16), 0.54 (1H, d, J=7.68 Hz, H-15); $\delta_C$ 141.03, 127.67, 126.24, 126.09, 102.22, 90.82, 81.10, 72.99, 51.46, 43.45, 37.46, 36.64, 34.16, 32.08, 25.68, 24.88, 24.71, 19.85, 13.62; m/z (CI, CH$_4$) 345 (M$^+$+1, 14%), 327 (14), 299 (100); Anal.Calc. for $C_{21}H_{28}O_4$: C, 73.26; H, 8.14; Found: C, 73.58; H, 8.32.

nOe-difference experiment: irradiation of the doublet signal of H-10 at 67 5.75 gave 10% enhancement in the multiplet signal of H-9 at δ 2.75; this showed that the stereochemistry of H-10 and H-9 are syn to each other.

EXAMPLE 3

Preparation of 10α-(4'-fluorobenzylamino) dihydroartemisinin (Formula I: X=H; Y=—NR$^3$R$^4$; R$^3$=H; R$^4$=4-F benzyl; Z=O. Formula IV: A=—NR$^3$R$^4$; R$^3$=H; R$^4$=4-F benzyl (a) Preparation of 10-(trimethylsiloxy)dihydroartemisinin (Formula II: Q=—Si(CH$_3$)$_3$)

To a solution of dihydroartemisinin (1.51 g, 5.32 mmol) in dichloromethane (40 ml) at 0° C. under nitrogen was added dropwise triethylamine (0.94 ml, 6.65 mmol) and chlorotrimethylsilane (0.84 ml, 6.65 mmol). The mixture was stirred at room temperature for a further 1 hour and poured into ice-water mixture. The aqueous solution was extracted with dichloromethane (2×20 ml). The combined organic layers were dried (MgSO$_4$) and concentrated in vacuo. The residue was purified by flash chromatography (SiO$_2$; 5% ethyl acetate/hexanes) to give a white 10β-(trimethylsiloxy)dihydroartemisinin as a white solid (1.48 g, 78%). $\delta_H$ 5.49 (1H, s, H-12), 5.19 (1H, d, J=3.05 Hz, H-10), 2.52–2.62 (1H, m, H-9), 2.39 (1H, ddd, J=17.5, 13.4, 4.01 Hz), 2.04 (1H, ddd, J=14.5, 4.84, 3.05 Hz), 1.20–1.97 (9H, m), 1.45 (3H, s, H-14), 0.97 (3H, d, J=6.24 Hz, H-16), 0.87 (3H, d, J=7.29 Hz, H-15), 0.17 (9H, s, (CH$_3$)$_3$Si).

When the 10-β-(trimethylsiloxy)dihydroartemisinin was recrystallised in dichloromethane, it epimerised to give the α-anomer completely. $\delta_H$ 5.32 (1H, s, H-12), 4.76 (1H, d, J 9.00 Hz, H-10), 2.25–2.45 (2H, m, H-8, H-9), 2.01 (1H, m, H-4), 1.89 (1H, m, H-5), 1.18–1.79 (8H, m, H-2a, H-2b, H-3a, H-3b, H-6a, H-6b, H-7a, H-7b), 1.31 (3H, s, 1-CH$_3$) 0.95 (3H, d, J 5.88 Hz, 9-CH$_3$), 0.86 (3H, d, J 7.14 Hz, 5-CH$_3$), 0.20 (9H, s, Me$_3$Si) ppm.

(b) Preparation of 10α-(4'-fluorobenzylamino) dihydroartemisinin (Formula I: X=H; Y=—NR$^3$R$^4$; R$^3$=H; R$^4$=4-F benzyl; Z=O. Formula IV: A=—NR$^3$R$^4$; R$^3$=H; R$^4$=4-F benzyl)

A solution of 10-(trimethylsiloxy)dihydroartemisinin (214 mg, 0.600 mmol) prepared as described in (a) above in dichloromethane (5 ml) at 0° C. was treated dropwise with bromotrimethylsilane (80 μl, 0.600 mmol). The mixture was stirred at 0° C. for a further 30 minutes after which it was then transferred by cannula into a solution of 4-fluorobenzylamine (140 μl 1.20 mmol) in tetrahydrofuran (5 ml) at 0° C. The mixture was stirred at 0° C. and then allowed to reach room temperature overnight. The suspension was washed with saturated NaHCO$_3$ solution, dried (MgSO$_4$) and concentrated in vacuo. The residue was purified by flash chromatography (SiO$_2$; 15% ethyl acetate/hexanes) to give 10α-(4'-fluorobenzylamino) dihydroartemisinin (76.9 mg, 33%) and 9,10-anhydrodehydroartemisinin (84.7 mg, 78%), both as white solids. M.p. 45.2–46.3° C. $\delta_H$ 7.32–7.37 (2H, Ar—H), 6.95–7.02 (2H, m, Ar—H), 5.29 (1H, s, H-12), 4.10 (1H, d, J=13.8 Hz, H-1'), 4.08 (1H, d, J=9.76 Hz, H-10), 3.91 (1H, d, J=13.8 Hz, H-1'), 2.33–2.42 (2H, m), 1.85–2.07 (3H, m), 1.65–1.77 (2H, m), 1.03–1.75 (5H, m), 1.46 (3H, s, H-14), 0.96 (3H, d, J=6.02 Hz, H-16), 0.93 (3H, d, J=7.19 Hz, H15); $\delta_C$ 13.642 (d, J=3.10 Hz), 129.30 (d, J=7.97 Hz), 114.75 (d, J=21.1 Hz), 103.90, 91.35, 85.47, 80.60, 51.66, 47.50, 45.82, 37.23, 36.26, 34.03, 32.72, 26.03, 24.61, 21.70, 20.15, 14.06; $\delta_F$ –118; m/z (CI, CH$_4$) 392 (M$^+$+1, 90%), 374 (54), 346 (100), 328 (20), 267 (16), 209 (16), 165 (26), 109 (18).

EXAMPLE 4

Preparation of 10-(2',4'-dimethoxyphenyl) dihydroartemisinin (Formula I: X=H; Y=2,4-dimethoxyphenyl; Z=O. Formula IV: A=2,4-dimethoxyphenyl)

(a) Preparation of 9-10-anhydroartemisinin

To a solution of dihydroartemisinin (500 mg, 1.86 mmol) in dichloromethane (28 ml) at 0°0 C. under nitrogen was added 4-(N,N-dimethylamino)pyridine (37 mg) and trifluoroacetic anhydride (0.79 ml, 5.58 mmol). The mixture was allowed to warm to room temperature and stirred overnight. The solution was then concentrated in vacuo. The residue was purified by flash chromatography (SiO$_2$; ether:hexane from 0.5:9.5 to 1.5:8.5) to give 9,10-anhydroartemisinin (180 mg, 25%) as a white solid. M.p. 100° C.; $[\alpha]_D^{20.5}$+ 155.74° (c.0.0101 in CHCl$_3$); $\nu_{max}$ (film): 2948, 2922, 2862, 2850, 1684, 1432, 1372, 1334, 1198, 1178, 1158, 1142, 1114, 1078, 1028, 1016, 992, 954, 944, 904, 880, 828, 812; $\delta_H$: 6.18 (1H, s, H-10), 5.54 (1H, s, H-12), 2.40 (1H, ddd, J=17.1, 13.2, 4.14 Hz, H-9), 2.00–2.09 (2H, m), 1.88–1.95 (1H, m), 1.07–1.73 (8H, m), 1.58 (3H, d, J=1.37 Hz, H-16), 1.42 (3H, s, H-14), 0.98 (3H, d, J=5.98 Hz, H-15); m/z (EI): 380 (M$^+$); Anal.Calc. for $C_{15}H_{22}O_4$: C, 67.67; H, 8.27; Found: C, 67.63; H, 8.51 nOe-difference experiment: (300 MHz, CDCl$_3$); irradiation or the singlet signal of H-10 at δ 6.18 gave no enhancement in the multiplet signal of H-9 at δ 2.05.

(b) Preparation of 10-(2',4'-dimethoxyphenyl) dihydroartemisinin (Formula I: X=H; Y=2,4-dimethoxyphenyl; Z=O. Formula IV: A=2,4-dimethoxyphenyl)

To a solution of 9,10-anhydroartemisin (191 mg, 0.71 mmol) prepared as described in (a) above and 1,3-dimethoxybenzene (130 μl, 1.00 mmol) in dichloromethane (10 ml) at room temperature under nitrogen was added boron trifluoride diethyl etherate (2 drops). The solution was stirred for a further 1 hour, and then quenched with 20% hydrochloric acid solution (5 ml). The mixture was extracted with diethyl ether (3×20 ml), and the ether extracts were dried (MgSO$_4$) and concentrated in vacuo. The residue was purified by flash chromatography (SiO$_2$; 15% ethyl acetate/hexanes) to give 10-(2',4'-dimethoxyphenyl) dihydroartemisinin (89.5, 44%) as a white solid. $\delta_H$ 7.56 (1H, brd, J=8.4 Hz, Ar—H), 6.40–6.58 (2H, m, Ar—H), 5.43 (1H, s, H12), 5.42 (1H, s, H-12'), 5.16 (1H, d, J=10.8 Hz, H-10), 4.96 (1H, d, J=10.3 Hz, H-10'), 3.82, 3.78 (OMe), 2.37–2.48 (2H, m), 1.05–2.07 (10H, m), 1.62 (3H, s, H-14), 1.34 (3H, s, H-14'), 1.00 (3H, d, J=6.22 Hz, H-16'), 0.90–0.93 (3H, m, H-15 & H-16), 0.59 (3H, d, J=7.22 Hz, H-15'); m/z (CI, NH$_3$) 422 (M+NH$_4^+$, 26%), 406 (84), 405 (M$^+$+1, 54), 389 (80), 359 (100), 330 (30), 317 (40), 300 (14).

EXAMPLE 5

Preparation of 10α-(2'-hydroxy-1'-naphthyl)dihydro artemisinin (Formula I: X=H; Y=2-OH naphthyl; Z=O. Formula IV: A=2-OH naphthyl)

(a) Preparation of 10β-(2'naphthoxy)dihydroartemisinin

To a solution of dihydroartemisinin (568 mg, 2.00 mmol) and 2-naphthol (288 mg, 2.00 mmol) in tetrahydrofuran (10 ml) was added triphenylphosphine (524 mg, 4.00 mmol) and diethyl azodicarboxylate (330 μl, 2.00 mmol) at ° C. under nitrogen. The mixture was stirred at room temperature overnight. The yellow solution was then concentrated in vacuo and the residue purified by flash chromatography (SiO$_2$; 5% ethyl acetate/hexanes) to give 10β-(2'-naphthyloxy)dihydroartemisinin (185 mg, 23%) as a white solid.

(b) Preparation of 10α-(2'-hydroxy-1'-naphthyl)-dihydroartemisinin

To a solution of 10β-(2'-naphthoxy)dihydroartemisinin (232 mg, 0.564 mmol) prepared as described in (a) above in dichloromethane (10 ml) was added boron trifluoride dietherate (220 μl) at 0° C. The mixture was allowed to warm to room temperature and stirred for a further 30 minutes. The solution was washed with 10% sodium hydrogen carbonate solution (2×5 ml), dried (MgSO$_4$) and concentrated in vacuo. The residue was then purified by flash chromatography (SiO$_2$; 10% ethyl acetate/hexanes) to give 10α-(2'-hydroxy-1'-naphthyl)dihydroartemisinin as a white solid (72.7 mg). δ$_H$ 8.91 (1H, s, OH), 7.28–7.91 (6H, m, Ar—H), 5.57 (1H, s, H-12), 3.11–3.19 (1H, m), 1.28–2.55 (11H, m), 1.51 (3H, s, H-14), 1.04 (3H, d, J=5.96 Hz, H-16), 0.63 (3H, d, J=7.23 Hz, H-16).

EXAMPLE 6

Preparation of 10α-(thiomorpholino) dihydroartemisinin (Formula I: X=H; Y= thiomorpholino; Z=O. Formula IV: A= thiomorpholino)

Reaction of bromide prepared from 10-(trimethylsiloxy) dihydroartemisinin (356 mg, 1.00 mmol) as described in Example 3(b) above with thiomorpholine (300 μl, 3.00 mmol) afforded 10α-(thiomorpholino)dihydroartemisinin (243 mg, 66%) as a white solid after flash chromatography (8% ethyl acetate/hexanes). M.p. 147.0–147.6° C.; [α]$_D^{20}$+ 17° (c 0.021/CHCl$_3$); ν$_{max}$ (film) 2924, 2872, 1454, 1418, 1376, 1326, 1278, 1226, 1198, 1184, 1154, 1130, 1100, 1056, 1038, 1018, 988, 940, 926, 880, 850, 828, 756; δ$_H$ 5.23 (1H, s, H-12), 3.93 (1H, d, J=10.21 Hz, H-10), 3.20–3.28 (2H, m), 2.85–2.93 (2H, m), 2.53–2.68 (5H, m), 2.25–2.36 (1H, m), 1.93–2.01 (1H, m), 1.78–1.86 (1H, m), 1.63–1.70 (2H, m), 1.14–1.52 (5H, m), 1.36 (3H, s, H-14), 0.90–1.04 (1H, m), 0.91 (3H, d, J=6.14 Hz, H-16), 0.76 (3H, d, J=7.18 Hz, H-15); δ$_C$: 103.70, 92.28, 91.42, 80.11, 51.54, 50.39, 45.66, 37.19, 36.14, 34.12, 28.15, 25.84, 24.59, 21.44, 20.15, 13.41; m/z (CI, NH$_3$) 370 (M$^+$+1, 100), 324 (70), 310 (10): Anal. Calc. for C$_{19}$H$_{31}$NO$_4$S: C, 61.76; H, 8.46; N, 3.79%; found C, 62.04; H, 8.39; N, 3.65.

EXAMPLE 7

Preparation of 10α-(4'-S,S-dioxothiomorpholinyl) dihydroartemisinin (Formula I: X=H; Y=4-S,S-dioxothiomorpholinyl; Z=O, Formula IV: A=4-S,S-dioxothiomorpholinyl)

To a solution of 10α-(thiomorpholino)dihydroartemisinin (388 mg, 1.05 mmol) prepared as described in Example 6 above in dichloromethane (10 ml) at room temperature under nitrogen was added NMO (369 mg, 3.15 mmol), powdered molecular sieve (525 mg, 4 Å), and TPAP (18.5 mg, cat.). The mixture was stirred at room temperature overnight after which it was filtered through a pad of SiO$_2$ and the residue was washed with ethyl acetate (3×15 ml). The filtrate was concentrated in vacuo. The residue was then purified by flash chromatography (SiO$_2$; 35% ethyl acetate/hexanes) to give 10α-(4'-S,S-dioxothiomorpholinyl) dihydroartemisinin as a white solid (421 mg, 100%). M.p. 152.3–152.7° C.; [α]$_D^{20}$+13° (c 0.035/CHCl$_3$); ν$_{max}$ (film) 2928, 2872, 1454, 1378, 1308, 1270, 1228, 1198, 1124, 1040, 1018, 976, 940, 878, 846, 826, 752, 704, 666; δ$_H$: 5.27 (1H, s, H-12), 4.21 (1H, d, J=10.30 Hz, H-10), 3.18–3.46, (8H, m), 2.54–2.62 (1H, m), 2.28–2.36 (1H, m), 1.20–2.02 (9H, m), 1.35 (3H, s, H-14), 0.92–1.06 (1H, m), 0.93 (3H, d, J=5.99 Hz, H-15), 0.78 (3H, J=7.13 Hz, H-16); δ$_C$: 174.20, 104.09, 91.92, 90.84, 90.04, 51.74, 51.27, 46.88, 45.46, 37.29, 36.02, 34.04, 28.91, 25.76, 24.66, 21.45, 20.10, 13.31; m/z (CI,NH$_3$) 402 (M$^+$+1, 100), 373 (30), 356 (64), 342 (16), 356 (20); Anal. Calc. for C$_{19}$H$_{31}$NO$_6$S: C, 56.84; H, 7.78; N, 3.49; found: C, 56.83; H, 7.82; N, 3.37.

EXAMPLE 8

Preparation of 10-dihydroartemisinyl ethanoate (α- and β-isomers) (Formula I: X=H; Y=—O—CO—R$^5$; R$^5$=—CH$_3$; Z=). Formula IV: A=—O—CO—R$^5$; R$^5$=—CH$_3$)

To a solution of dihydroartemisinin (284 mg, 1.00 mmol) in dichloromethane (15 ml) at 0° C. under nitrogen was added 4-(N,N-dimethylamino)pyridine (20 mg) and acetic anhydride (330 μl, 3.00 mmol). The mixture was allowed to warm to room temperature and stirred overnight. The solution was concentrated in vacuo. Flash chromatography (SiO$_2$; 20% ethyl acetate/hexanes), gave 10α-dihydroartemisinyl ethanoate as a white solid (321 mg, 98%). Recrystallisation of the product with ethyl acetate/hexane gave the acyl derivative of dihydroartemisinin as needle-shaped crystals. M.p. 128–129° C.; [α]$_D^{20}$: +76.2° (c 0.93/CHCl$_3$); ν$_{max}$ (film): 2926, 2870, 1752, 1448, 1376, 1228, 1132, 1102, 1028, 876, 848, 826, 754; δ$_H$: 5.80 (1H, d, J=9.85 Hz, H-10), 5.45 (1H, s, H-12), 2.55 (1H, m, H-9), 2.39 (1H, ddd, J=17.5, 13.4, 3.91 Hz), 2.14 (3H, s, CH$_3$CO), 2.04 (1H, ddd, J=14.6, 4.82, 3.00 Hz), 1.23–1.94 (9H, m), 1.45 (3H, s, H-14), 0.97 (3H, d, J=5.94 Hz, H-15), 0.86 (3H, d, J=7.15 Hz, H-16); m/z (EI): 326 (M$^+$). Anal. Calcd. for C$_{17}$H$_{26}$O$_6$: C, 62.56; H, 8.03; Found C, 62.87; H; 8.36.

nOe-Difference experiment: (300 MHz, CDCl$_3$): irradiation of the doublet signal of H-10 at δ 5.80 gave no enhancement in the multiplet signal of H-9 at δ 2.55, this showed that the stereochemistry of H-9 and H-10 are anti to each other.

The presence of the ethanoic acid arising from decomposition caused residual α-ethanoate to epimerise into the β-ethanoate; $^1$H nmr (300 MHz, CDCl$_3$) of the β-acetate, δ$_H$ 6.24 (1H, d, J 3.27 Hz, H-10), 5.48 (1H, s, H-12), 2.79 (1H, m, H-9), 2.38 (1H, m, H-8), 2.08 (3H, s, CH$_3$CO), 1.21–2.04 (10H, m, H-4, H-5, H-2a, H-2b, H-3a, H-3b, H-6a, H-6b, H-7a, H-7b), 1.42 (3H, s, 1-CH$_3$), 0.97 (3H, d, J 6.12 Hz, 9-CH$_3$), 0.86 (3H, d, J 2.40 Hz, 5-CH$_3$) ppm.

EXAMPLE 9

Preparation of 10β-dihydroartemisinyl benzoate (Formula I: X=H; Y=—O—CO—R$^5$; R$^5$=phenyl; Z=O. Formula IV: A=—O—CO—R$^5$; R$^5$=phenyl)

To a solution of dihydroartemisinin (568 mg, 2.00 mmol) and benzoic acid (244 mg, 2.00 mmol) in tetrahydrofuran at 0° C. under nitrogen was added triphenylphosphine (524 mg, 2.00 ml) and diethyl azodicarboxylate (ml). The mixture was allowed to warm to room temperature and stirred overnight. The solution was concentrated in vacuo. Flash chromatography (SiO$_2$; 10% ethyl acetate/hexanes) gave 10β-dihydroartemisinyl benzoate as a white solid (419 mg, 53%). M.p. 151.4–153.0° C.; [α]$_D^{20}$ +119° (c 0.19/CHCl$_3$); ν$_{max}$ (film): 2942, 2872, 1724, 1452, 1378, 1268, 1176, 1114, 1064, 1024, 976, 902, 858, 832, 754, 712; δ$_H$ 7.43–8.03 (5H, m, Ar—H), 6.52 (1H, d, J=3.43, H-10), 5.58 (1H, s, H-12), 2.91–3.01 (1H, m, H-9), 2.42 (1H, ddd, J=17.4, 13.3, 3.91 Hz), 1.33–2.10 (10H, m), 1.45 (3H, s, H-14), 1.02 (3H, d, J=6.11 Hz, H-15), 0.98 (3H, d, J=7.35 Hz, H-14); δ$_C$: 165.31, 133.03, 129.96, 129.48, 128.39, 104.30, 95.29, 88.66, 88.63, 80.42, 52.27, 43.84, 37.44, 36.10, 34.43, 29.98, 25.78, 24.50, 24.25, 20.14, 12.50; m/z (EI): 388 (M$^+$).

EXAMPLE 10

Preparation of 10α-dihydroartemisinyl benzoate (Formula I: X=H; Y=—O—CO—R$^5$; R$^5$=phenyl; Z=O. Formula IV: A=—O—CO—R$^5$, R$^5$=phenyl)

To a solution of dihydroartemisinin (284 mg, 1.00 mmol) and benzoic acid (122 mg, 1.00 mmol) in dichloromethane (15 ml) at 0° C. under nitrogen was added dicyclohexylcarbodiimide (1.05 mmol). The mixture was stirred at 0° C. for 4 hours. The solution was washed with water (3×15 ml), dried (MgSO$_4$) and concentrated in vacuo. Flash chromatography (SiO$_2$; 15% ethyl acetate/hexanes) gave 10α-dihydroartemisinyl benzoate as a white solid (137 mg, 35%). δ$_H$: 8.11–8.14 (2H, m, Ar—H), 7.28–7.60 (3H, m, Ar—H), 6.02 (1H, d, J=9.84, H-10), 5.54 (1H, s, H-12), 2.75–2.79 (1H, m, H-9), 2.35–2.44 (1H, m), 2.03–2.08 (1H, m), 1.66–1.89 (4H, m), 1.26–1.54 (4H, m), 1.44 (3H, s, H-14), 0.89–1.07 (1H, m), 0.99 (3H, d, J=5.95 Hz, H-14), 0.94 (3H, d, J=7.15 Hz, H-15); δ$_C$: 165.22, 133.24, 130.05, 129.55, 128.23, 104.36, 92.46, 91.52, 80.12, 51.58, 45.28, 37.21, 36.19, 34.06, 31.93, 25.89, 24.52, 21.99, 20.18, 12.17.

EXAMPLE 11

Preparation of 10β-[(2',2',2'-trifluoroethyl)oxy]-dihydroartemisinin (Formula I: X=H; Y=—OR$^6$; R$^6$=—CH$_2$CF$_3$; Z=O. Formula IV: A=—OR$^6$; R$^6$=—CH$_2$CF$_3$)

To a solution of dihydroartemisinin (426 mg, 1.50 mmol) and 2,2,2-trifluoroethanol (220 μl, 3.00 mmol) in diethyl ether (30 ml) at room temperature under nitrogen was added boron trifluoride dietherate (3 drops). The mixture was stirred at room temperature for 6 hours. The reaction was quenched with saturated NaHCO$_3$ solution, dried (MgSO$_4$) and concentrated in vacuo. Flash chromatography (SiO$_2$: 8% ethyl acetate/hexanes) gave 10β-[(2',2',2'-trifluoroethyl) oxy]dihydroartemisinin (157 mg, 29%) and 9,10-anhydrodehydroartemisinin (133 mg, 46%) both as white solids. Ether: M.p. 113.4–114.2° C.; [α]$_D^{20}$: +133° (c 0.30/CHCl$_3$); ν$_{max}$ (film): 2984, 2960, 2928, 2870, 1454, 1414, 1378, 1308, 1278, 1174, 1150, 1110, 1052, 1036, 990, 972, 918, 874, 824; δ$_H$: 5.43 (1H, s, H-12), 4.90 (1H, d, J=3.46 Hz, H-10), 4.15 (1H, dq, J=12.2, 8.87 Hz, H-1'), 3.89 (1H, d, J=12.2, 8.67 Hz, H-1'), 2.65–2.75 (1H, m, H-9), 2.40 (1H, ddd, J=17.5, 13.4, 4.02 Hz), 2.07 (1H, ddd, J=14.6, 4.83, 3.01 Hz), 1.64–1.96 (5H, m), 1.22–1.58 (4H, m), 1.46 (3H, s, H-14), 0.98 (3H, d, J=5.94 Hz, H-16), 0.97 (3H, d, J=7.69 Hz, H-15); δ$_C$: 104.13, 102.41, 87.93, 80.73, 64.91 (d, J=34.3 Hz), 52.32, 43.99, 37.29, 36.17, 34.39, 30.44, 25.90, 24.47, 24.11, 20.13, 12.47; m/z (CI, NH$_3$): 384 (M+NH$_4^+$, 16%), 367 (M$^+$+1, 2), 284 (100), 267 (72).

EXAMPLE 12

Preparation of 10β-[4'-(7'-trifluoromethyl-quinolinoxy)]dihydroartemisinin (Formula I: X=H; Y=—OR$^6$; R$^6$=7-CF$_3$ quinolin-4-yl; Z=O. Formula IV: A=OR$^6$; R$^6$=7-CF$_3$ quinolin-4-yl To a solution of dihydroartemisinin (286 mg, 1.00 mmol) and 7-trifluoromethyl-4-quinolinol (213 mg, 1.00 mmol) in tetrahydrofuran (10 ml) was added triphenylphosphine (262 mg, 2.00 mmol) and diethyl azodicarboxylate (165 μl, 1.00 mmol) at 0° C. under nitrogen. The mixture was stirred at room temperature overnight. The yellow solution was concentrated in vacuo. The residue was purified by flash chromatography (SiO$_2$: 40% ethyl acetate/hexanes) to give 10β-[4'-(7'-trifluoromethylquinolinoxy)]-dihydroartemisinin (315 mg, 66%) as a white solid. The white solid was recrystallised from ethyl acetate-hexane mixture to give a white needle-shaped crystal. M.p. 270–272° C.; [α]$_D^{21.5}$+ 73.30° (c. 0.0179 in CHCl$_3$); ν$_{max}$ (Nujol): 2922, 1596, 1570, 1510, 1456, 1378, 1332, 1302, 1194, 1162, 1132, 1098, 1064, 1040, 1014, 984, 950, 930, 898, 874, 828, 738, 684 cm$^{-1}$; δ$_H$: 7.39–8.91 (5H, m, Ar—H), 5.84 (1H, d, J=3.35 Hz, H-10), 5.47 (1H, s, H-12), 2.99–3.07 (1H, m, H-9), 2.38–2.48 (1H, m), 1.69–2.23 (7H, m), 1.35–1.49 (3H, m), 1.49 (3H, s, H-14), 1.15 (3H, d, J=7.35 Hz, H-15), 0.99 (3H, d, J=5.67 Hz, H-16); δ$_F$: 61.09; m/z (CI, CH$_4$): 480 (M$^+$+1, 12%), 460 (28), 267 (80), 221 (100), 214 (72), 163 (60).

EXAMPLE 13

Preparation of 10α and β-[(2'-naphthylmethyl)oxy] dihydroartemisinin (Formula I: X=H; Y=—OR$^6$; R$^6$=—CH$_2$-(2-naphthyl); Z=O. Formula IV: A=—OR$^6$; R$^6$=—CH$_2$-(2-naphthyl)

(a) Preparation of 10-(trimethylsiloxy)dihydroartemisinin

To a solution of dihydroartemisinin (1.51 g, 5.32 mmol) in pyridine (20 ml) at 0° C. under nitrogen was added dropwise chlorotrimethylsilane (5.20 ml, mmol). The mixture was stirred at room temperature for a further 1 hour and poured into ice-water mixture. The solution was extracted with diethyl ether (3×15 ml), dried (MgSO$_4$) and concentrated in vacuo. The residue was purified by flash chromatography (SiO$_2$; 5% ethyl acetate/hexanes) to give 10-(trimethylsiloxy)dihydroartemisinin as a white solid (1.47 g, 78%). δ$_H$ 5.49 (1H, s, H-12), 5.19 (1H, d, J=3.05 Hz, H-10), 2.52–2.62 (1H, m, H-9), 2.39 (1H, ddd, J=17.5, 13.4, 4.01 Hz), 2.04 (1H, ddd, J=14.5, 4.84, 3.05 Hz), 1.20–1.97 (9H, m), 1.45 (3H, s, H-14), 0.97 (3H, d, J=6.24 Hz, H-16), 0.87 (3H, d, J=7.29 Hz, H-15), 0.17 (9H, s, (CH$_3$)$_3$Si).

(b) Preparation of 10α- and β-[(2'-naphthylmethyl)oxy] dihydroartemisinin (Formula I: X=H; Y=—OR$^6$; R$^6$=—CH$_2$-(2-naphthyl); Z=O. Formula IV: A=OR$^6$; R$^6$=—CH$_2$-(2-naphthyl)).

Procedure 1 (at −78° C.).

To a solution of 10-(trimethylsiloxy)dihydroartemisinin (238 mg, 0.67 mmol) prepared as described in (a) above and 2-naphthylmethanol trimethylsilyl ether (170 mg, 0.74 mmol) in distilled dichloromethane (8 ml) was added a catalytic amount of trimethylsilyl trifluoromethanesulphonate (TMSOTf) solution (5 μl TMSOTf in 1 ml dichloromethane) under a nitrogen atmosphere at −78° C. The reaction mixture was continuously stirred at −78° C. for 18 hours, then it was diluted with dichloromethane (20 ml), washed with sodium hydrogen carbonate solution (10%, 2×10 ml) and dried over anhydrous magnesium sulphate. After filtration of the magnesium sulphate, the filtrate was evaporated in vacuo. The two anomers were separated by repeated column chromatography (SiO$_2$, -ether:hexane from 1:3 to 3:7). The β-anomer was obtained as a white foam (93 mg, 33%) and the α-anomer was obtained as a colourless viscous liquid (35 mg, 12%).

Procedure 2 (at 0° C.).

The same reaction with the same amount of reactants was performed at 0° C., the reaction mixture was stirred at 0° C. for 2 hours, the α- and β-anomers were separated by column chromatography using the same solvent system. The α-anomer (30 mg, 11%) was the minor product and the β-anomer was the major product (237 mg, 84%). Raising the temperature of this reaction decreases the amount of the side products (dimers of the two reactants involved) or increases the yield of the anomers but changes the ratio of the 2 anomers.

Procedure 3 (higher yield of the α-anomer).

To a solution of dihydroartemisinin (100 mg, 0.35 mmol) and 2-naphthylmethanol (61 mg, 0.39 mmol) in dichloromethane at −20° C. under a nitrogen atmosphere was added a catalytic amount of chlorotrimethylsilane.

The resulting mixture was stirred at −20° C. until the reaction was complete. The reaction was then quenched with a saturated solution of NaHCO$_3$ the organic layer was isolated and dried. After evaporation of the solvent, the product was isolated by column chromatography (SiO$_2$, ether:hexane, from 2:8 to 3:7) to give a pair of anomeric ethers (28.8 mg, 78%) with α:β ratio of 1:3. β-anomer: M.p. 51–52° C.; $[α]_D^{20.5}$+108.73° (c. 0.0102 in CHCl$_3$); $ν_{max}$ (Neat): 3056, 2922, 2874, 1604, 1510, 1450, 1376, 1344, 1322, 1310, 1266, 1226, 1194, 1176, 1158, 1140, 1100, 1060, 1012, 956, 940, 876, 824, 738 cm$^{-1}$; $^1$H nmr (300 MHz, CDCl$_3$, $δ_H$ 7.38–7.84 (7H, m, Ar—H), 5.50 (1H, s, H-12), 5.04 (1H, d, J 12.36 Hz, Ha-1'), 4.95 (1H, d, J 3.45 Hz, H-10), 4.68 (1H, d, J 12.36 Hz, Hb-1'), 2.69 (1H, m, H-9), 2.38 (1H, dt, J 14.13, 4.17 Hz, H-8), 2.01 (1H, m, H-4), 1.18–1.91 (9H, m, H-2×2, H-3×2, H-5, H-6×2, H-7× 2), 1.44 (3H, s, 1-CH$_3$), 0.95 (3H, d, J 7.35 Hz, 9-CH$_3$), 0.91 (3H, d, J 5.97 Hz, 5-CH$_3$) ppm; m/z (CI, NH$_3$): 441 ([M+NH$_3$]$^+$, 2), 378 ([M−3CH$_3$−1]$^+$, 27), 221 ([M—C$_{11}$H$_9$O—O$_2$—CH$_3$+1]$^+$, 100), 141 (71); Anal.Calc. for C$_{26}$H$_{32}$O$_5$: 73.56; H, 7.60; Found, C, 73.27; H, 7.64.

nOe-difference experiment: (300 MHz, CDCl$_3$): irradiation of the doublet signal of H-10 at δ 4.95 gave 9.4% enhancement in the multiplet signal of H-9 at δ 2.69, this showed that the stereochemistry of H-9 and H-10 are syn to each other.

α-anomer: $[α]_D^{20.5}$−54.66° (c. 0.0118 in CHCl$_3$); $ν_{max}$ (Neat): 3058, 2924, 1636, 1450, 1976, 1132, 1032, 878, 852, 824, 742 cm$^{-1}$; $^1$H nmr (300 MHz, CDCl$_3$) $δ_H$ 7.41–7.85 (7H, m, Ar—H), 5.34 (1H, s, H-12), 5.12 (1H, d, J 12.60 Hz, Ha-1'), 4.81 (1H, d, J 12.60 Hz, Hb-1'), 4.55 (1H, d, J 9.21 Hz, H-10), 2.55 (1H, m, H-9), 2.40 (1H, m, H-8), 2.05 (1H, m, H-4), 1.10–1.92 (9H, m, H-2×2, H-3×2, H-5, H-6×2, H-7×2), 1.48 (3H, s, 1-CH$_3$), 0.92 (6H, d×2, J 7.35 Hz, 5-CH$_3$, 9-CH$_3$) ppm; m/z (CI, NH$_3$): 441 ([M+NH$_3$]$^+$, 1), 378 ([M—3CH$_3$−1]$^+$, 26), 267 ([M—C$_{11}$H$_9$O]$^+$, 18), 221 ([M—C$_{11}$H$_9$O—O$_2$—CH$_3$+1]$^+$, 100), 163 (13), 141 (88);

nOe difference experiment: (300 MHz, CDCl$_3$): irradiation of the doublet signal of H-10 at δ 4.55 gave 65% enhancement in the singlet signal of H-12 at δ 5.34, this showed that the stereochemistry of H-12 and H-10 are syn to each other.

EXAMPLE 14

Preparation of 11-azaartemisinin (Formula I: X=H; Y=O; Z=NR$^7$; R$^7$=H. Formula V: A=H)

To a saturated solution of methanolic ammonia (12 ml) at room temperature was added artemisinin (1.128 g, 4 mmol). The solution was stirred for 1.5 hours and concentrated under reduced pressure to give a light yellow solid. The solid was dissolved in dichloromethane (180 ml), and 2,6-di-tert-butyl-4-methylphenol (BHT) (80 mg, 0.36 mmol), 15% sulphuric acid (0.8 ml), and silica gel (8.0 g) were added in succession. After stirring overnight at room temperature, the reaction mixture was filtered and the silica gel washed with dichloromethane. The combined organic solution and washes were concentrated under reduced pressure. Column chromatography of the residue on silica gel with acetone:dichloromethane (8:92) gave crystalline solid 11-azaartemisinin (510 mg, 45%): mp 143–145° C.; R$_f$=0.40 (acetone:CH$_2$Cl$_2$, 15:85); $[α]^{25}_D$=−40.9° (c 0.127, CH$_2$Cl$_2$); IR 3313, 3223, 2928, 2873, 1668 cm$^{-1}$; CIMS (NH$_3$) 299 (M+NH$_4$$^+$, 76), 282 (M+1,100); $^1$H NMR δ 0.93–1.01 (2H, m), 0.93 (3H, d, J=5.5 Hz), 1.07 (3H, d, J=7.2 Hz), 1.30 (3H, s), 1.25–1.42 (3H, m), 1.61–1.70 (2H, m), 1.71–1.77 (1H, m), 1.92 (2H, dm, J=10.2 Hz), 2.34 (1H, m), 3.17 (1H, pent, J=6.8 Hz), 5.33 (1H, s), 5.93 (1H, bs).

EXAMPLE 15

Preparation of 11-aza-N-(2-fluorobenzyl)artemisinin (Formula I: X=H; Y=O; Z=NR$^7$; R$^7$=2-F benzyl. Formula V: A=2-F benzyl)

Artemisinin (410 mg, 1.44 mmol) was suspended in methanol (4.5 ml) and cooled to 0° C. Freshly distilled 2-fluorobenzylamine (360 mg, 2.88 mmol) was added and the reaction mixture was stirred under nitrogen at 0° C. for 48 hours. After this time, the solvent was evaporated and the residue quickly dissolved in dichloromethane (67.5 ml). Para-toluene sulphonic acid (550 mg, 2.88 mmol)) was added and the solution stirred at room temperature overnight, extracted with 5% NaHCO$_3$ solution and water, dried over magnesium sulphate and evaporated. Flash chromatography (10% ethyl acetate/hexane) gave 11-aza-N-(2-fluorobenzyl)artemisinin (210 mg, 37%) as a yellow viscous liquid. Recrystallisation from light petroleum ether gave white needles: M.p. 70.5–71° C.; $[α]_D^{20.5}$+5.55° (c. 0.0182 in CHCl$_3$); $ν_{max}$ (Neat): 2928, 1660 ($ν_{C=O}$, amide), 1586, 1490, 1446, 1378, 1330, 1270, 1228, 1204, 1136, 1098, 1072, 1028, 1002, 952, 918, 88, 836, 756, 700 cm$^{-1}$; $^1$H NMR (300 MHz, CDCl$_3$): $δ_K$ (ppm)=0.83–1.08 (m, 1 H), 0.97 (d, J$_{6-Me,6}$=5.8 Hz, 3H, 6-CH$_3$), 1.02(s, 3H, 3-CH$_3$), 1.18 (d, J$_{9-Me,9}$=7.4 Hz, 3H, 9-CH$_3$), 1.25–1.51 (m, 3H), 1.65–1.76 (m, 3H), 1.80 (td, J=12.9 Hz, J=3.6 Hz, 1H), 1.91–2.04 (m, 2H), 2.32–2.43 (m, 1H), 3.40 (dq, J$_{9,9-Me}$=7.4 Hz, J$_{9,8a}$=4.9 Hz, 1H, H-9), 4.67 (d, J=15.2 Hz, 1H, H-1'β), 4.89 (d, J=15.2 Hz, 1H, H-1'α), 5.24 (s, 1H, H-12), 6.96–7-38 (m, 4H, phenyl-H); MS (FAB: m/z(%)=390 [M$^+$+1] (56), 357 [M$^+$-O$_2$] (4), 307 (24), 289 (12), 165 (8), 154 (100), 136 (68); Anal. Calc. for C$_{22}$H$_{28}$FNO$_4$: C, 67.85; H, 7.25; N, 3.59; Found: C, 67.81; H, 7.55; N, 3.48.

EXAMPLE 16

Preparation of 11-aza-N-(ethoxycarbonylethyl) artemisinin (Formula I: X=H; Y=O; Z=NR$^7$; R$^1$=—CH$_2$CH$_2$COOC$_2$H$_5$. Formula V: A=—CH$_2$CH$_2$COOC$_2$H$_5$)

To a solution of 11-azaartemisinin produced as described in Example 1 (27 mg, 0.01 mmol) in anhydrous tetrahydrofuran (2 ml) were added at room temperature a trace of powdered sodium hydroxide and freshly distilled ethyl acrylate (31 μl, 0.03 mmol). After stirring for one hour, another trace of sodium hydroxide was added and stirring continued for one additional hour. The reaction was then quenched by adding dilute aq. sodium sulphite solution (5 ml). The water layer was extracted with dichloromethane (3×10 ml). The combined organic layers were successively washed with saturated aqueous sodium hydrogen carbonate, brine, water, and dried over sodium sulphate. Evaporation of the solvent gave a crude oily product which was purified by silica gel chromatography (ethyl acetate/hexane, 4:1). This gave N-ethoxycarbonyl-ethyl-11-azaartemisinin as a clear oil (31.6 mg, 86%): CIMS (NH$_3$) 399 (M+NH$_4^+$, 100), 382 (M+1,90); $^1$H NMR (CDCl$_3$, 300 MHz) δ 0.92–0.98 (2H, m) 0.99 (3H, d, J=5.97 Hz), 1.13 (3H, d, J=7.16 Hz), 1.25 (3H, t, J=7.06 Hz), 1.37 (3H, s), 1.26–1.43 (3H, m), 1.63–1.78 (3H, m), 2.01 (2H, dm, J=10.1 Hz), 2.41 (1H, m), 2.50–2.61 (1H, m), 2.75–2.85 (1H, m), 3.27 (1H, p, J=6.95 Hz), 3.61–3.70 (1H, m), 3.79–3.88 (1H, m), 4.12 (2H, q, J=7.13 Hz), 5.33 (1H, s); $^{13}$C NMR (CDCl$_3$, 75.4 MHz) δ 13.2, 14.5, 20.1, 23.0, 25.4, 25.8, 33.0, 33.5, 34.0, 37.0, 37.9, 38.8, 45.9, 51.8, 60.8, 79.2, 80.5, 105.2, 172.2, 172.9.

EXAMPLE 17

Preparation of 9-(N,N-dibenzylaminomethyl) artemisinin (Formula I: X=—NR$^1$R$^2$; R$^1$=R$^2$=benzyl, Y==O; Z=O Formula VI: A=—CH$_2$N (benzyl)$_2$)

(a) Preparation of 9,10-anhydrodehydroartemisinin

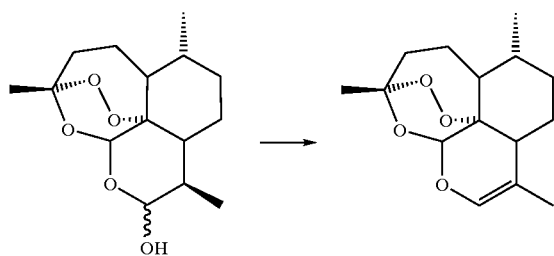

To a solution of dihydroartemisinin (10.4 g) in diethyl ether (550 ml) at room temperature under nitrogen was added dropwise boron trifluoride dietherate (1.0 ml). The solution was stirred at room temperature overnight, washed with 5% NaHCO$_3$ solution (3×100 ml); dried (MgSO$_4$) and concentrated in vacuo. The residue was then purified by flash chromatography (SiO$_2$; 10% ethyl acetate/hexanes) to give 9,10-anhydrodehydroartemisinin as a white solid (16.8 g, 97%). δ$_H$: 6.20 (1H, q, J=1.41 Hz, H-10), 5.55 (1H, s, H-12), 2.33–3.50 (1H, m), 1.03–2.18 (10H, m), 1.60 (3H, d, J=1.41 Hz, H16), 1.44 (3H, s, H-14), 1.00 (3H, d, J=5.98 Hz, H-15).

(b) Preparation of 9-hydroperoxyartemisitene

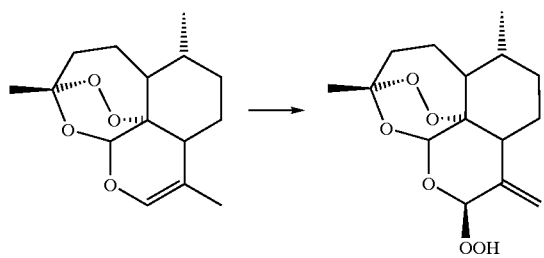

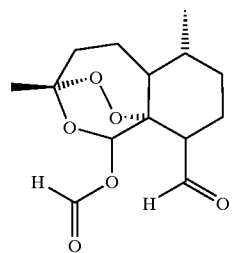

To a solution of 9,10-anhydrodehydroartemisinin (5.32 g, 19.9 mmol) prepared as described in (a) above in dichloromethane (250 ml) was added methylene blue (2 mg). The light blue solution was bubbled with oxygen for 10 minutes after which the solution was then irradiated under an oxygen atmosphere. After completion of reaction, the solution was concentrated in vacuo. The residue was then purified by flash chromatography (SiO$_2$; gradient elution; ethyl acetate/hexanes 20:80 to 30:70) to give two white solids. The less polar product was the ring opened formyl aldehyde (0.58 g, 9.7%) and the more polar product was the desired hydroperoxide (2.13 g, 36%). Hydroperoxide: m.p. 149–150° C.; [α]$_D^{20}$: +162 (c=0.06, CHCl$_3$); δ$_H$: 10.2 (1H, s, OOH), 5.88 (1H, s, H-12), 5.76 (1H, s, H-10), 5.33 (1H, s, =CH$_2$), 5.20 (1H, s, =CH$_2$), 1.48 (3H, s, H-14), 0.99 (3H, d, J=5.84 Hz, H-15).

Formyl aldehyde: m.p. 103–104° C.; [α]$_D^{20}$: −59 (c=0.05 CHCl$_3$); δ$_H$: 7.94 ($_1$H, s, H-10), 6.58 (1H, s, H-12), 2.52 (3H, s, CH$_3$CO), 1.48 (3H, s, H-14), 1.05 (3H, d, J=6.24 Hz, H-15).

(c) Preparation of artemisitene

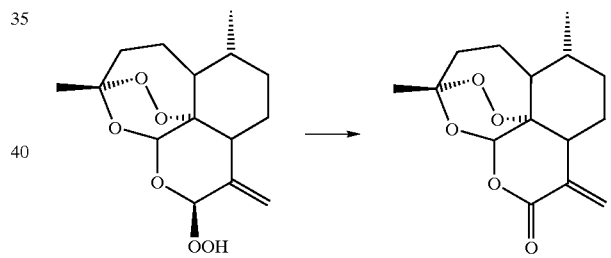

To a solution of hydroperoxide (2.00 g, 6.67 mmol) prepared as described in (b) above in acetic anhydride (12 ml) was added pyridine (0.6 ml). The mixture was stirred at room temperature for 1 hour. The solution was washed with 1 N hydrochloric acid (3×10 ml), 5% NaHCO$_3$ solution (3×10 ml) and water (3×10 ml); dried (MgSO$_4$) and concentrated in vacuo. The residue was then purified by flash chromatography (SiO$_2$; ethyl acetate/hexanes 25:75) to give artemisitene as a white solid (1.72 g, 92%). m.p. 161–162° C.; [α]$_D^{20}$: +132 (c=0.06 CHCl$_3$); δ$_H$: 6.58 (1H, s, =CH$_2$), 6.01 (1H, s, =CH$_2$), 5.69 (1H, s, H-12), 2.50 (1H, dd, J=13.5, 4.45 Hz), 2.38–2.48 (1H, m), 1.97–2.11 (2H, m), 1.73–1.83 (2H, m), 1.40–1.69 (4H, m), 1.47 (3H, s, H-14), 1.15–1.27 (1H, m), 1.03 (3H, d, J=5.62 Hz, H-15).

(d) Preparation of 9-(N,N-dibenzylaminomethyl)artemisinin (Formula I: X=—NR$^1$R$^2$; R$^1$=R$^2$=benzyl, Y==O; Z=O. Formula VI: A=—CH$_2$N (benzyl)$_2$)

To a solution of dibenzylamine (110 μl, 0.550 mmol) in tetrahydofuran at −78° C. under nitrogen was added dropwise n-butyllithium (220 μl, 0.550 mmol, 2.5 M). The solution was stirred for a further 15 minutes. A precooled (0° C.)solution of artemisitene (140 mg, 0.500 mmol prepared as described in Example 1(c) above in tetrahydrofuran was then added dropwise through cannula to the above solution. The mixture was stirred for a further 1 hour, then quenched with saturated $NH_4Cl$ solution, extracted with diethyl ether (3×15 ml), dried ($MgSO_4$) and concentrated in vacuo. The residue was purified by flash chromatography ($SiO_2$; 20% ethyl acetate/hexanes) to give 9-(N,N-dibenzylaminomethyl)artemisinin as a colourless oil (150 mg, 63%). $\delta_H$ 7.23–7.38 (10H, m, Ar—H), 5.86 (1H, s, H-12), 3.77 (2H, d J=13.6 Hz, $(PhCH_2)_2N$), 3.50 (2H, d J=13.6 Hz, $(PhCH_2)_2N$), 3.04–3.16 (2H, m, H-16), 2.18–2.30 (2H, m), 1.88–2.07 (3H, m), 1.65–1.71 (1H, m), 0.86–1.50 (6H, m), 1.41 (3H, s, H-14), 1.00 (3H, d, J=6.15 Hz, H-15); $\delta_C$: 170.75, 139.17, 129.05, 128.13, 126.87, 104.97, 93.68, 80.23, 58.73, 58.51, 50.17, 43.78, 39.81, 37.46, 35.66, 34.06, 31.03, 25.33, 24.63, 19.83; m/z (CI, $CH_4$) 478 ($M^++1$, 20), 298 (100), 268 (34), 198 (6).

EXAMPLE 18

Preparation of 9- [2,2-di(ethoxycarbonyl)ethyl]-artemisinin (Formula I: 1 X=—$CHR^8R^9$; $R^8=R^9$=—CO—$OC_2H_5$; Y==O; Z=). formula VII: A=—$CH_2$—CH(CO—$OC_2H_5)_2$; Y==O)

To an ice-cold solution of malonic acid diethyl ester (800.8 mg, 5 mmol) in 10 ml tetrahydrofuran was slowly added sodium hydride (218.2 mg, 5 mmol, 55% in paraffin oil). The resulting solution was then added to an ice-cold solution of artemisitene (1.4 g, 5 mmol) prepared as described in Example 17 (c) above in 20 ml tetrahydrofuran under nitrogen. The mixture was stirred for 4 hours at 0° C., then at room temperature overnight. After this, it was poured into 50 ml ice-water, neutralised and extracted with ether. After drying over $MgSO_4$, the solvent was evaporated and the residue purified by column chromatography to give 9-[2,2-di(ethoxycarbonyl)ethyl]artemisinin (785.1 mg, 35.6%); $\delta_H$: 5.92 (1H, s, H-12), 4.12–4.30 (2×2H, m, $OCH_2CH_3$), 3.90 (1H, dd, J=9.08, 6.44 Hz, H-17), 2.58–2.65 (1H, m, H-9), 1.01–1.31 (2×3H, m, $OCH_2CH_3$), 1.00 (3H, d, J=5.80 Hz, H-15).

EXAMPLE 19

Preparation of 9-[2-(ethoxycarbonyl)ethyl]artemisinin (Formula I: X=—$CHR^8R^9$; $R^8$=H; $R^9$=—CO—$OC_2H_5$; Y==O; Z=O. Formula VII: A=—$(CH_2)_2$—CO—)$C_2H_5$; Y==O)

Method 1

Artemisitene (280 mg, 1 mmol) prepared as described in Example 17 (c) above was dissolved in dry tetrahydrofuran (5 ml) under nitrogen and the silylated reagent acetic acid ketene-ethyltrimethylsilylacetal (2 mmol) was added at a temperature of 0° C. Subsequently, this mixture was added to a −78° C. cold suspension of tris(dimethylamino) sulphur (trimethylsilyl)difluoride (TASF) (56 mg, 0.2 mmol) in tetrahydrofuran (5 ml) and the reaction was stirred at −78° C. overnight. Glacial acetic acid (40 ml) was added and the mixture stirred for a further 30 minutes at room temperature. After this time, the solvent was evaporated and the residue was dried in vacuo before purification by flash chromatography to give 9-[2-(ethoxycarbonyl)ethyl]artemisinin (109.9 mg, 29.8%) as an oil.

Method 2

A solution of ethyl acetate (105 μl, 1.10 mmol) in tetrahydrofuran (5 ml) at −78° C. under nitrogen was added dropwise to lithium diisopropylamide (0.74 ml, 1.10 mmol, 1.5 M). The mixture was stirred at −78° C. for a further 15 minutes after which it was then added dropwise to a solution of artemisitene (280 mg, 1.00 mmol) prepared as described in Example 1 (c) above in tetrahydrofuran (5 ml) at −78° C. The solution was stirred for a further 1 hour, quenched with saturated $NH_4Cl$ solution, extracted with diethyl ether (3×15 ml); dried ($MgSO_4$) and concentrated in vacuo. The residue was purified by flash chromatography ($SiO_2$; 28% ethyl acetate/hexanes) to give 9-[2-(ethoxycarbonyl)ethyl]artemisinin as a colourless oil (209 mg, 57%). $\delta_H$: 5.92 (1H, s, H-12), 4.13 (2H, q, J=7.16 Hz, $OCH_2CH_3$), 2.22–2.66 (6H, m), 1.90–2.13 (3H, m), 1.69–1.86 (3H, m), 1.05–1.57 (4H, m), 1.46 (3H, s, H-14), 1.26 (3H, t, J=7.16 Hz, $OCH_2CH_3$), 1.00 (3H, d, J=5.90 Hz, H-15); $\delta_C$: 173.08, 171.14, 105.14, 93.69, 79.98, 60.23, 50.35, 43.66, 43.64, 37.41, 35.78, 33.82, 30.85, 31.21, 29.31, 25.32, 24.54, 19.72, 14.08; m/z (CI, $CH_4$): 369 ($M^++1$, 30%), 323 (32), 305 (68), 277 (100), 259 (44).

EXAMPLE 20

Preparation of 10-desoxo-9-[2-(ethoxycarbonyl) ethyl]-artemisinin (Formula I: X=$CHR^8R^9$; $R^8$=H; $R^9$=—CO—$OC_2H_5$; Y=—H; Z=O. Formula VII: A=—$(CH_2)_2$—CO—$OC_2H_5$; Y=—H)

9-[2-(Ethoxycarbonyl)ethyl]artemisinin (0.5 mmol) prepared as described in Example 19 above was mixed with boron trifluoride etherate (1.86 ml, 15 mmol) in tetrahydrofuran (5 ml) under nitrogen with ice-cooling. This solution was added to a suspension of sodium borohydride (44 mg, 1.12 mmol) in 5 ml tetrahydrofuran at 0° C. The mixture was stirred under nitrogen at 0° C. for a further 3 hours and then boiled for 10 minutes. Subsequently, ice was added to the cooled solution and the latter neutralised with $NaHCO_3$ and extracted with ether. The solvent was evaporated and the residue purified by column chromatography to give 10-desoxo-9-[2-(ethoxycarbonyl)ethyl]artemisinin as an oil (23.6 mg, 13.4%); $\delta_H$: 4.94 (1H, s, H-12), 4.12 (2H, q, J=7.14 Hz, $OCH_2CH_3$), 3.75–3.87 (2H, m, H-10), 3.40–3.56 (2H, m, H-17), 1.17–2.46 (14H, m), 1.55 (3H, s, H-14), 1.25 (3H, t, J=7.14 Hz, $OCH_2CH_3$), 1.01 (3H, d, J=6.27 Hz, H-15).

EXAMPLE 21

Preparation of 16-(2'-propyl)artemisinin (9-(2-methylpropyl)artemisinin) (Formula I: X=—$CHR^8R^9$; $R^8=R^9$=$CH_3$; Y==O; Z=O. Formula VII: =A=—$CH_2CH(CH_3)_2$; Y==O)

To a solution of artemisitene (280 mg, 1.00 mmol) prepared as described in Example 1 (c) above and 2-bromopropane (140 μl, 1.50 mmol) in 1,2-dimethoxyethane (15 ml) was added a catalytic amount of AIBN (50 mg). The mixture was heated at 80° C. for 3 hours. The solution was concentrated in vacuo. The residue was then purified by flash chromatography ($SiO_2$; 15% ethyl acetate/hexanes) to give 16-(2'-propyl)artemisinin (9-(2-methylpropyl)artemisinin) as a white solid (0.293 g, 90%). M.p. 105.5–106.6° C.; $[\alpha]_D^{20}$: +79.7° (c 0.37/$CHCl_3$); $\nu_{max}$ (film) 2956, 2870, 1738, 1456, 1376, 1198, 1154, 1108, 1032, 1006, 982, 938, 876, 832, 760; $\delta_H$ 5.92 (1H, s, H-12), 2.36–2.46 (1H, m), 2.22–2.27 (1H, m), 1.88–2.16 (3H, m), 1.62–1.83 (5H, m), 1.05–1.58 (5H, m), 1.47 (3H, s, H-14), 1.01 (3H, d, J=5.80 Hz, H-15), 0.96 (3H, d, J=6.34 Hz, $CH_3CHCH_3$), 0.91 (3H, d, J=6.34 Hz, $CH_3CHCH_3$); m/z (CI, $CH_4$) 325 ($M^++1$, 28%), 308 (56), 291 (40), 279 (56), 261 (68), 251 (100), 221 (26); Anal. Calc. for $C_{18}H_{28}O_5$: C, 66.64; H, 8.70; Found: C, 66.38, H, 8.77.

EXAMPLE 22

Preparation of 16-(N-1'-indolinyl)artemisinin (Formula I: X=—NR$^1$R$^2$; R$^1$,R$^2$=1'indolyl, Y==O; Z=O. Formula VI: A=—CH$_2$-indolyl)

To a solution of indoline (135 μl, 1.2 mmol) in tetrahydofuran at −78° C. under nitrogen was added dropwise n-butyllithium (440 μl, 1.1 mmol, 2.5 M). The solution was stirred for a further 15 minutes. A precooled (0° C.) solution of artemisitene (280 mg, 1.00 mmol prepared as described in Example 17(c) above in tetrahydrofuran was then added dropwise through cannula to the above solution. The mixture was stirred for a further 1 hour, then quenched with saturated NH$_4$Cl solution, extracted with diethyl ether (3×15 ml), dried (MgSO$_4$) and concentrated in vacuo. The residue was purified by flash chromatography (SiO$_2$; 23% ethyl acetate/hexanes) to give 16-(N-1'-indolyl)artemisinin, M.p. 64.9–65.1° C.; $[\alpha]_D^{20}$+74.4° (c 0.018/CHCl$_3$); $\nu_{max}$ (film): 2926, 1732, 1606, 1488, 1456, 1376, 1276, 1228, 1154, 1126, 1106, 1030, 998, 880, 830, 748; $\delta_H$ 7.08–7.12 (2H, m, Ar—H), 6.59–6.72 (2H, m, Ar—H), 6.00 (1H, s, H-12), 3.81 (1H, dd, J=13.5, 11.3 Hz, ArCH$_2$), 3.57 (1H, ddd, J=9.06, 8.89, 5.24 Hz, NCH$_2$), 3.49 (1H, dd, J=13.5, 4.79 Hz, ArCH$_2$), 3.29 (1H, ddd, J=9.33, 9.06, 8.89 Hz, NCH$_2$), 2.93–3.12 (2H, m, H-16), 2.42–2.62 (2H, m), 1.94–2.17 (3H, m), 1.37–1.75 (6H, m), 1.51 (3H, s, H-14), 1.09–1.22 (1H, m), 1.00 (3H, d, J=5.89 Hz), H-15); $\delta_C$ 170.21, 152.44, 129.36, 127.37, 124.32, 117.61, 106.73, 105.32, 93.80, 80.39, 54.14, 53.73, 50.22, 44.29, 39.59, 37.45, 35.75, 33.78, 31.28, 28.50, 25.35, 24.65, 19.72; m/z (CI, CH$_4$): 400 (M$^+$+1, 100), 399 (M$^+$, 76), 371 (14), 132 (90); Anal. Calc. for C$_{23}$H$_{29}$NO$_5$: C, 69.15; H, 7.32; N, 3.50; Found, 69.28; H, 7.33; N, 3.31.

EXAMPLE 23

Preparation of 10α-(4'-benzylpiperazin-1'-yl)-10-deoxo-10-dihydroartemisinin (Formula I: Y=4'-benzyl-1'-piperazinyl) X=H, Z==O; Formula VI: A=4'-benzyl-1'-piperazinyl Reaction of the bromide prepared from 10β-(trimethylsiloxy)dihydroartemisinin (356 mg, 1.00 mmol) as described in Example 3(b) with 1-benzylpiperazine (212.1 μl, 1.22 mmol) afforded 10α-(4'-benzylpiperazin-1'-yl) -10-deoxo-10-dihydroartemisinin (144.3 mg, 40%) as a white solid after flash chromatography (40% ethyl acetate/hexane). M.p. 105–106° C.; $[\alpha]_D^{20}$+10.3° (c. 0.909 CHCl$_3$); $\nu_{max}$ (film): 2954, 2920, 2860, 2802, 1494, 1454, 1376, 1344, 1294, 1270, 1204, 1132, 1114, 1062, 1042, 1016, 986, 942, 924, 880, 852, 824, 738, 694 cm$^{-1}$; $^1$H NMR (300 MHz, CDCl$_3$) $\delta_H$ 7.43–7.30 (5H, m, Ar—H), 5.35 (1H, s, H-12), 4.10 (1H, d, J=10.2 Hz, H-10), 3.62 (1H, d, J=13.1 Hz, benzylic-H), 3.55 (1H, d, J=13.1 Hz, benzylic-H), 3.11–3.06 (2H, m), 2.80–2.70 (2H, m), 2.70–2.30 (7H, m), 2.15–2.02 (1H, m), 2.02–1.85 (1H, m), 1.85–1.70 (2H, m), 1.70–1.20 (9H, m), 1.20–1.00 (4H, m), 0.88 (3H, d, J=7.2 Hz, 6-methyl) ppm; $^{13}$C NMR (76 MHz, CDCl$_3$) $\delta_C$ 138.3, 129.13, 128.1, 126.9, 103.8, 91.6, 90.4, 80.3, 63.1, 53.5, 51.7, 45.9, 37.4, 36.3, 34.3, 28.5, 26.0, 24.8, 21.6, 20.3, 13.4 ppm; MS (CI, CH$_4$) m/e 443 (M$^+$+1, 10). Anal. Calcd. for C$_{26}$H$_{38}$N$_2$O$_4$: C, 7056, H, 8.65, N, 6.33; Found: C, 70.24, H, 8.67, N, 6.28.

EXAMPLE 24

Preparation of 10α-(2'-furyl)-10-deoxo-10-dihydroartemisinin (Formula I: Y=2-furyl) X=H, Z==O; Formula VI: A=2-furyl Method 1:

To a solution of dihydroartemisinin (284 mg, 1.0 mmol) in dichloromethane (10 mL) at 20° C. was added trichloroacetonitrile (2.0 mL, 20.0 mmol) and one drop of 1,8-diazabicyclo[5.4.0]undecane. The mixture was stirred at 20° C. for 2 hours after which it was concentrated in vacuo at 20° C. The residue was then taken up in dichloromethane (10 mL) at 0° C. and cooled to −40° C. The solution was treated sequentially with furan (1.09 mL, 15.0 mmol) and boron trifluoride diethyl etherate (123 μl, 1.0 mmol), and the resulting mixture was stirred at −40° C. for another 30 min. The mixture was quenched with saturated NaHCO$_3$ solution and extracted with dichloromethane (2×10 mL). The extracts were dried (MgSO$_4$) and concentrated in vacuo. The residue was purified by flash chromatography (SiO$_2$; 15% ethyl acetate/hexanes) to give the captioned compound (11.0 mg, 3.3%) as a colourless oil. Analytical sample was obtained from recrystallization from hexanes.

Method 2:

(a) Preparation of 10β-benzoyloxy-10-dihydroartemisinin (10β-dihydroartemisinyl benzoate)

To a solution of dihydroartemisinin (568 mg, 2.00 mmol) and benzoic acid (244 mg, 2.00 mmol) in tetrahydrofuran at 0° C. under nitrogen was added triphenylphosphine (524 mg, 2.00 mmol) and diethyl azodicarboxylate (ml). The mixture was allowed to warm to room temperature and stirred overnight. The solution was concentrated in vacuo. Flash chromatography (SiO$_2$; 10% ethyl acetate/hexanes) gave 10β-dihydroartemisinyl benzoate as a white solid (419 mg, 53%). M.p. 151.4–153.0° C.; $[\alpha]_D^{20}$+119° (c 0.19/CHCl$_3$); $\nu_{max}$ (film): 2942, 2872, 1724, 1452, 1378, 1268, 1176, 1114, 1064, 1024, 976, 902, 858, 832, 754, 712; $\delta_H$ 7.43–8.03 (5H, m, Ar—H), 6.52 (1H, d, J=3.43, H-10), 5.58 (1H, s, H-12), 2.91–3.01 (1H, m, H-9), 2.42 (1H, ddd, J=17.4, 13.3, 3.91 Hz), 1.33–2.10 (10H, m), 1.45 (3H, s, H-14), 1.02 (3H, d, J=6.11 Hz, H-15), 0.98 (3H, d, J=7.35 Hz, H-14); $\delta_C$: 165.31, 133.03, 129.96, 129.48, 128.39, 104.30, 95.29, 88.66, 88.63, 80.42, 52.27, 43.84, 37.44, 36.10, 34.43, 29.98, 25.78, 24.50, 24.25, 20.14, 12.50; m/z (EI): 388 (M$^+$).

(b) Preparation of 10α-(2'-furyl)-10-deoxo-10-dihydroartemisinin (Formula I: Y=2-furyl) X=H, Z==O; Formula VI: A=2-furyl A solution of 10β-benzoyloxy-10-dihydroartemisinin (193 mg, 0.50 mmol) in dichloromechane (5 mL) at −45° C. was treated sequentially with furan (542 μl, 7.5 mmol) and boron trifluoride diethyl etherate (123 μl, 1.0 mmol). The resulting mixture was stirred at −45° C. for another 1 hr. The mixture was quenched with saturated NaHCO$_3$ solution and extracted with dichloromethane (3×10 mL). The extracts were dried (MgSO$_4$) and concentrated in vacuo. The residue was purified by flash chromatography (SiO$_2$; 15% ethyl acetate/hexanes) to give the captioned compound (53.7 mg, 32%) as a colourless oil. M.p. 96–97° C.; $^1$H NMR (300 MHz, CDCl$_3$) $\delta_H$ 7.38 (1H, m, H-5'), 6.34–6.30 (2H, m, H-3 & H-4'), 5.38 (1H, s, H-12), 4.46 (1H, d, J=10.9 Hz, H-10), 2.84 (1H, m), 2.60–2.20 (2H, m), 2.20–1.20 (9H, m), 1.20–0.80 (6H, m), 0.62 (3H, d, J=7.2 Hz, 6-methyl) ppm; $^{13}$C NMR (76 MHz, CDCl$_3$) $\delta_C$ 153.2, 142.0, 110.0, 108.3, 104.2, 92.2, 80.4, 76.6, 71.1, 52.0, 45.7, 37.4, 36.3, 34.1, 31.5, 26.1, 24.7, 21.3, 20.3, 13.7 ppm; MS (CI, CH$_4$) m/e 335 (M$^+$+1, 43).

EXAMPLE 25

Preparation of 10α-(Pyrrol-2'-yl)-10-deoxo-10-dihydroartemisinin (Formula I: Y=2-pyrrolyl) X=H, Z==O; Formula VI: A=2-pyrrolyl A solution of 10β-benzoyloxy-10-deoxoartemisinin (700.8 mg, 1.80 mmol) prepared as described in Example 24, Method 2(a) in dichloromethane (30 mL) at −50° C. was treated sequentially with pyrrole (624 μl, 9.00 mmol) and boron trifluoride diethyl etherate (332 μl, 2.70 mmol), and then stirred at −50° C. for 1 hr. The mixture was quenched with saturated $NaHCO_3$ solution, and extracted with dichloromethane (3×10 mL). The extracts were dried ($MgSO_4$) and concentrated in vacuo. The residue was purified by flash chromatography ($SiO_2$; 30% diethyl ether/hexanes) to give the captioned compound (486.6 mg, 81%) as a colourless oil. $[\alpha]_D^{20}$+198.7° (c 0.105 $CHCl_3$); $\nu_{max}$ (film): 2924, 2854, 1460, 1376, 1066, 1024, 722 $cm^{-1}$; $^1H$ NMR (300 MHz, $CDCl_3$) $\delta_H$ 8.80 (1H, br s, NH), 6.71 (1H, m, H-5'), 6.04 (2H, m, H-3' & H-4'), 5.39 (1H, s, H-12), 4.47 (1H, d, J=10.8 Hz), 2.58 (1H, m), 2.50–2.10 (2H, m), 2.10–1.95 (1H, m), 1.93 (1H, m), 1.80–1.68 (2H, m), 1.68–1.15 (7H, m), 1.15–0.80 (4H, m), 0.93 (3H, d, J=7.1 Hz, 6-methyl) ppm; $^{13}C$ NMR (76 MHz, $CDCl_3$) $\delta_C$ 129.9, 117.6, 107.2, 106.7, 104.1, 91.9, 80.5, 71.9, 60.2, 51.8, 45.7, 37.2, 36.2, 34.0, 32.9, 25.9, 24.6, 21.2, 20.1, 14.0, 13.9 ppm; MS (CI, butane) m/e 334 ($M^+$+1, 100). Anal. Calcd. for $C_{19}H_{27}NO_4$: C, 68.44, H, 8.16, N, 4.20; Found: C, 68.77, H, 8.56, N, 3.85.

EXAMPLE 26

Preparation of 10α-(4'-Benzyl-4'-methylpiperazinium-1'-yl)-10-deoxo-10-dihydroartemisinin Iodide Salt (Formula I: Y=4'-benzyl-4'-methylpiperazinium-1'-yl) X=H, Z==O; Formula VI: A=4'-benzyl-4'-methylpiperazinium-1'-yl A solution of 10α-(4'-benzyipiperazin-1'-yl)-10-deoxo-10-dihydroartemisinin (272 mg, 0.62 mmol) prepared as described in Example 23 above in a mixture of dichloromethane (1.8 mL) and diethyl ether (5.4 mL) under nitrogen atmosphere at 0° C. was treated dropwise with iodomethane (36.7 μl, 0.59 mmol). The mixture was agitated and allowed to warm to 20° C. gradually overnight. The precipitate was collectent and washed with diethyl ether (2×5 mL) and dried in high vacuum. It was further purified by recrystallization from methanol/diethyl ether to yield rectangular-plate shaped crystals (87 mg, 24%). M.p. 159–161° C.; $[\alpha]_D^{20}$+18.4° (c 0.436 $CHCl_3$); $\nu_{max}$ (film): 3448, 2928, 2196, 1457, 1378, 1210, 1133, 1099, 1041, 982, 918, 880, 852, 828, 766, 732, 642 $cm^{-1}$; $^1H$ NMR (300 MHz, $CDCl_3$) $\delta_H$ 8.00–7.60 (2H, d, J=6.2 Hz, H-2" & H-6"), 7.60–7.35 (3H, m, Ar—H), 5.32 (1H, s, H-12), 5.25–5.05 (2H, m, benzylic-H), 4.13 (1H, d, J=10.2 Hz, H-10), 3.95–3.55 (4H, n), 3.55–2.90 (9H, m), 2.65–2.20 (2H, m), 2.20–1.15 (14H, m), 1.15–0.87 (4H, m), 0.80 (3H, d, J=6.9 Hz, 6-methyl) ppm; $^{13}C$ NMR (76 MHz, $CDCl_3$) $\delta_C$ 133.4, 130.6, 129.1, 126.5, 104.0, 91.5, 90.1, 80.1, 67.4, 59.5, 59.3, 51.5, 45.5, 37.2, 36.1, 34.0, 28.4, 25.9, 24.5, 21.5, 20.1, 13.3 ppm

EXAMPLES 27 to 104

By processes similar to those described in Examples 1 to 26 above, further compounds according to the invention were prepared as detailed. In Tables I, II, III and IV. In these tables, the compounds are identified by reference to formula I. In Table I, X is a hydrogen atom and Z is an oxygen atom in all examples. In Table II, X is a hydrogen atom, Y is an oxo group and Z is a group =NR' in all examples. In Table III, X is a group —$NR^1R^2$, Y is an oxo group and Z is an oxygen atom in all examples. In Table IV, X is a group —$CHR^8R^9$ and Z is an oxygen atom in all examples. It should also be noted that the compounds of Table I are also compounds of Formula IV, the compounds of Table II are also compounds of Formula V and the compounds of Table III are also compounds of Formula VI and the compounds of Table IV are also compounds of Formula VII.

TABLE I (X = H; Z = O)

| Ex. No. | Y | $R^3$ | $R^4$ | Physical data |
|---|---|---|---|---|
| 27 | 2,4,6-(—$OCH_3$)$_3$ phenyl (mixture of isomers) | — | — | White foam. $[\alpha]_D^{20.5}$ +49.51° (c. 0.053 in $CHCl_3$); $\nu_{max}$ (Neat): 2936, 2872, 1608, 1496, 1456, 1420, 1374, 1330, 1278, 1224, 1204, 1152, 1120, 1050, 1040, 974, 954, 930, 902, 880, 856, 834, 814, 734, 702 $cm^{-1}$: $\delta_H$ 6.10–6.18(2H, m, Ar—H), 5.46(1H, s, H12), 5.38(1H, s, H-12'), 5.31(1H, d, J=10.4Hz, H-10), 5.07(1H, d, J= 10.9Hz, H-10'), 3.88, 3.81, 3.80, 3.76 (OMe), 3.36–3.42(1H, m), 2.35–2.41(1H, m), 1.05–2.15(10H, m), 1.63(3H, s, H-14), 1.39(3H, s, H-14'), 0.99(3H, d, J=6.27Hz, H-16'), 0.88–0.93(3H, m, H-15 & H-16), 0.58(3H, d, J=7.26Hz, H-15'); m/z (CI, $NH_3$) 452($M+NH_4^+$, 4%), 436(16), 435($M^+$+1, 12), 419(100), 389 (74), 347(28). Anal. calc. for $C_{24}H_{34}O_7$: C, 66.36; H, 7.83; Found: C, 66.42; H, 7.89. |
| 28 | 2-naphthyl (10β-isomer) | — | — | White solid. M.p. 145–146° C.; $[\alpha]_D^{20}$: −67.8° (c 0.027/$CHCl_3$); $\nu_{max}$ (film) 2950, 2874, 1510, 1452, 1376, 1208, 1106, 1074, 1040, 1010, 954, 936, 886, 854, 824, 786, 750; $\delta_H$ 7.80–7.85(5H, m, Ar—H), 7.42–7.51(3H, m, Ar—H), 5.93(1H, d, J= 6.59Hz, H-10), 5.67(1H, s, H-12), 2.81–2.94(1H, m, H-9), 2.33–2.48(1H, m), 0.86–2.13(10H, m), 1.42(3H, s, H-14), 1.02(1H, d, J=6.09Hz, H-16), 0.55 (1H, d, J=7.66Hz, H-15); $\delta_C$ 134.85, 127.82, 127.42, 127.12, 125.65, 125.17, |

TABLE I-continued (X = H; Z = O)

| | | | | |
|---|---|---|---|---|
| | | | | 124.84, 124.26, 90.92, 73.04, 51.48, 43.44, 37.48, 36.64, 34.15, 32.10, 25.69, 24.89, 24.77, 19.85, 13.65; m/z (CI, CH$_4$) 395(M$^+$+1, 16%), 394(M+, 32), 362(44), 349(84), 331(16), 304(20), 291(26), 182(100), 168(60). Anal. Calcd. for C$_{25}$H$_{30}$O$_4$: C, 76.11; H, 7.66; found: C, 76.24; H, 7.69. |
| 29 | 2-OCH$_3$ phenyl (10β-isomer) | — | — | White solid. M.p. 61° C.; $[\alpha]_D^{20}$ −41.4° (c 0.049 CHCl$_3$); δ$_H$ 6.83–7.50(4H, m, Ar—H), 5.94(1H, d, J=6.65Hz, H-10), 5.58(1H, s, H-12), 3.84(3H, s, OC$\underline{H}_3$), 2.86–2.99 (1H, m, H-9), 2.30–2.40(1H, m), 1.19–2.11(10H, m), 1.39(3H, s, H-14), 1.01(1H, d, J=5.77Hz, H-16), 0.43(1H, d, J=7.64Hz, H-15); δ$_C$ 134.85, 127.00, 126.37, 120.02, 109.19, 90.86, 68.63, 55.19, 51.30, 43.39, 37.53, 36.72, 34.21, 29.87, 25.68, 24.97, 24.75, 19.83, 13.45; m/z (CI, CH$_4$) 375(M$^+$+1, 12%), 374(M$^+$, 16), 342(100), 329(48), 311(14), 284(28), 182(56), 148(76), 137(60); 121(48). Anal. Calcd. for C$_{22}$H$_{30}$O$_5$: C, 70.56; H, 8.07; found: C, 70.78; H, 8.28. |
| 30 | —NR$^3$R$^4$ (10α-isomer) | —H | phenyl | White solid. M.p. 159–160° C.; $[\alpha]_D^{20}$ −51.4° (c 0.35/CHCl$_3$); ν$_{max}$ (film) 3348, 2924, 2872, 1604, 1502, 1444, 1376, 1314, 1270, 1196, 1152, 1116, 1098, 1040, 1012, 994, 944, 926, 878, 856, 826, 748, 690; δ$_H$ 7.17–7.22(2H, m, Ar—H), 6.75–6.87(3H, m, Ar—H), 5.45(1H, s, H-12), 4.85(1H, dd, J=9.86, 9.81Hz, H-10), 4.32(1H, d, J=9.81Hz, NH), 2.49–2.61(1H, m, H-9), 2.35–2.45(1H, m), 2.00–2.08(1H, m), 1.74–1.92(4H, m), 1.26–1.65(7H, m), 1.42(3H, s, H-14), 1.05–1.10(1H, m), 1.01(3H, d, J=6.18 Hz, H-16), 0.95(3H, d, J=7.18Hz, H-15); δ$_C$ 128.99, 118.56, 114.02, 91.08, 80.70, 80.39, 51.71, 45.76, 37.18, 36.26, 34.03, 32.71, 25.97, 24.60, 21.79, 20.17, 13.80; m/z (CI, CH$_4$) 360(M$^+$+1, 56%), 359 (M+, 56), 342(98), 324(20), 314(100), 296(98), 267(50), 249(22), 221(80), 163(40), 133(100), 94(38). Anal. Calcd. for C$_{21}$H$_{29}$NO$_4$: C, 70.17; H, 8.13; N, 3.90; found: C, 70.25; H, 8.24; N, 3.73. |
| 31 | —NR$^3$R$^4$ (10α-isomer) | —H | 4-F phenyl | White solid. M.p. 170.1° C.; $[\alpha]_D^{20}$ −51.5° (c 0.013 CHCl$_3$); ν$_{max}$ (Nujol): 3358(ν$_{NH}$), 2924, 2854, 1512, 1460, 1378, 1264, 1216, 1194, 1116, 1099, 1046, 1022, 942, 924, 880, 846, 832, 810, 780 cm$^{-1}$, δ$_H$ 6.66–6.92 (4H, m, Ar—H), 5.44(1H, s, H-12), 4.76 (1H, dd, J=10.0, 10.0Hz, H-10), 4.32 (1H, d, J=10.0Hz, NH), 2.49–2.61(1H, m, H-9), 2.40*(1H, ddd, J=17.3, 13.4, 3.93Hz), 2.05(1H, ddd, J=14.6, 4.79, 3.07Hz), 1.05–1.97(9H, m), 1.42(3H, s, H-14), 1.00(3H, d, J=6.11Hz, H-16), 0.95(3H, d, J=7.18Hz, H-15); δ$_C$ 141.95, 115.34(d, J=17.7Hz), 115.15 (d, J=2.69Hz), 104.13, 91.10(d, J= 2.22Hz), 81.41, 80.41, 51.69, 45.73, 37.29, 36.25, 34.01, 32.60, 25.94, 24.60, 21.79, 20.17, 13.81; m/z (CI, CH$_4$) 378 (M$^+$+1, 44%), 377(M$^+$, 100), 358(70), 314 (14), 267(26), 221(18), 163(34), 151 (42), 111(6). Anal. Calc. for C$_{21}$H$_{28}$FNO$_4$: C, 66.82; H, 7.48; N, 3.71; Found C, 67.06; H, 7.60; N, 3.51. |
| 32 | —NR$^3$R$^4$ (10α-isomer) | —H | 4-Cl phenyl | White solid. M.p. 179.0° C.; $[\alpha]_D^{20}$ −63.5° (c 0.20/CHCl$_3$); ν$_{max}$ (film): 3346, 2926, 2874, 1604, 1514, 1494, 1454, 1378, 1268, 1196, 1152, 1094, 1040, 1012, 992, 944, 926, 878, 818, 756; δ$_H$ 7.09–7.14(2H, m, Ar—H), 6.66–6.71(2H, m, Ar—H), 5.44(1H, |

TABLE I-continued (X = H; Z = O)

| # | | | | Data |
|---|---|---|---|------|
| | | | | s, H-12), 4.78(1H, brs, H-10), 4.42(1H, brs, NH), 2.49–2.61(1H, m, H-9), 2.40 (1H, ddd, J=17.4, 13.5, 3.98Hz), 2.05 (1H, ddd, J=14.6, 4.78, 3.12Hz), 1.05–1.97(9H, m), 1.41(3H, s, H-14), 1.00(3H, d, J=6.12Hz, H-16), 0.94(3H, d, J=7.18Hz, H-15); $\delta_C$ 144.31, 128.76, 123.20, 115.28, 104.15, 91.09, 80.76, 80.38, 51.66, 45.67, 37.28, 36.23, 33.99, 32.56, 25.93, 24.59, 21.78, 20.16, 13.73; m/z (CI, CH$_4$) 393(M$^+$+1, 16%), 376 (8), 347(20), 330(16), 267(10), 221 (16), 167(100), 127(8). Anal. Calc. for C$_{21}$H$_{28}$ClNO$_4$: C, 64.03; H, 7.16; N, 3.55; Found C, 64.16; H, 7.40; N, 3.45. |
| 33 | —NR³R⁴ (10α-isomer) | —H | 4-Br phenyl | White solid. M.p. 183.1° C.; $[\alpha]_D^{20}$ −60.0° (c 0.23/CHCl$_3$); $\nu_{max}$ (film) 3346, 2924, 2872, 1598, 1514, 1492, 1452, 1378, 1268, 1196, 1152, 1122, 1094, 1040, 1012, 992, 926, 878, 816, 756; dH 7.20–7.25(2H, m, Ar—H), 6.61–6.66(2H, m, Ar—H), 5.44(1H, s, H-12), 4.78(1H, dd, J=10.0, 9.95Hz, H-10), 4.48(1H, d, J=10.0Hz, NH), 2.49–2.61(1H, m, H-9), 2.40(1H, ddd, J=14.0, 13.7, 3.87Hz), 1.05–2.08(10H, m), 1.41(3H, s, H-14), 1.00(3H, d, J=6.07 Hz, H-16), 0.94(3H, d, J=7.15Hz, H-15), $\delta_C$ 144.79, 131.61, 115.76, 110.32, 104.17, 91.09, 80.65, 80.39, 51.67, 45.67, 37.29, 36.24, 33.99, 32.54, 25.92, 24.60, 21.78, 20.17, 13.71; m/z (CI, CH$_4$) 439 (M$^+$+1, 12%), 422(14), 392(100), 376 (36), 267(14), 221(50), 154(34). Anal. Calc. for C$_{21}$H$_{28}$BrNO$_4$: C, 57.54; H, 6.44; N, 3.19; Found: C, 57.81; H, 6.64; N, 3.14. |
| 34 | —NR³R⁴ (10α-isomer) | —H | 4-I phenyl | White solid. $[\alpha]_D^{20}$ −68.8° (c 0.16/CHCl$_3$); $\nu_{max}$ (film) 3346, 2924, 1592, 1510, 1454, 1378, 1268, 1196, 1040, 994, 926, 878, 818, 754; $\delta_H$ 7.36–7.41(2H, m, Ar—H), 6.51–6.56(2H, m, Ar—H), 5.43(1H, s, H-12), 4.78(1H, dd, J=10.0, 9.97Hz, H-10), 4.56(1H, d, J=10.0Hz, NH), 2.34–2.56(2H, m, H-9), 1.05–2.08 (10H, m), 1.41(3H, s, H-14), 1.00(3H, d, J=6.04Hz, H-16), 0.93(3H, d, J=7.13 Hz, H-15); $\delta_C$ 145.46, 137.45, 116.35, 104.18, 91.09, 80.46, 79.59, 51.66, 45.66, 37.29, 36.25, 34.00, 32.50, 25.91, 24.61, 21.79, 20.19, 13.71; m/z (CI, CH$_4$) 486 (M$^+$+1, 4%), 485(M+, 6), 468(12), 440 (100), 422(34), 267(6), 259(20), 221 (20). Anal. Calc. for C$_{21}$H$_{28}$INO$_4$: C, 51.97; H, 5.81; N, 2.89; Found: C, 52.22; H, 5.83; N, 2.57. |
| 35 | —NR³R⁴ (10α-isomer) | —H | 4-biphenyl | White solid. $[\alpha]_D^{20}$ −76.5° (c 0.51/CHCl$_3$); $\nu_{max}$ (film) 3348, 2924, 2872, 1614, 1528, 1488, 1446, 1378, 1268, 1196, 1152, 1128, 1040, 1012, 992, 926, 878, 826, 760, 698; $\delta_H$ 7.25–7.58(7H, m, Ar—H), 6.82–6.87 (2H, m, Ar—H), 5.49(1H, s, H-12), 4.90 (1H, dd, J=9.85, 9.85Hz, H-10), 4.50 (1H, d, J=9.85Hz, NH), 2.36–2.62(2H, m), 1.07–2.09(10H, m), 1.44(3H, s, H-14), 1.02(3H, d, J=6.12Hz, H-16), 0.98(3H, d, J=7.17Hz, H-15); $\delta_C$ 145.22, 141.16, 131.53, 128.45, 127.71, 126.29, 125.98, 114.30, 104.14, 91.14, 80.67, 80.42, 51.72, 45.76, 37.30, 36.27, 34.04, 21.68, 25.98, 24.62, 21.81, 20.19, 13.81; m/z (CI, CH$_4$): 436(M$^+$+1, 2%), 412(100), 395(42), 379(8), 284(2), 267(2), 170 (2). Anal. Calc. for C$_{27}$H$_{31}$NO$_4$: C, 74.45; H, 7.64; N, 3.22; found: C, 73.51; H, 7.67; N, 3.12. |

TABLE I-continued (X = H; Z = O)

| | | | | |
|---|---|---|---|---|
| 36 | —NR³R⁴ (10α-isomer) | —H | benzyl | White solid. $[\alpha]_D^{20}$ −26.7° (c 0.15/CHCl₃); $\nu_{max}$ (film) 3348, 2924, 2870, 1452, 1376, 1158, 1116, 1056, 1042, 1014, 992, 942, 926, 878, 828, 736, 700; $\delta_H$ 7.21–7.42(5H, m, Ar—H), 5.32(1H, s, H-12), 4.17(1H, d, J=13.9Hz, H-1'), 4.13(1H, d, J=9.63 Hz, H-10), 3.97(1H, d, J=13.9Hz, H-1'), 2.29–2.45(2H, m), 2.29(1H, brs, NH), 2.01–2.09(1H, m), 1.86–1.95(1H, m), 1.65–1.78(2H, m), 1.44–1.59(2H, m), 1.48 (3H, s, H-14), 1.22–1.40(3H, m), 0.91–1.09(1H, m), 0.97(3H, d, J=5.94 Hz, H-16), 0.96(3H, d, J=7.14 Hz, H-15); $\delta_C$ 140.82, 128.03, 127.84, 126.45, 103.91, 91.39, 85.68, 80.65, 51.69, 48.21, 45.86, 37.24, 36.29, 34.07, 32.77, 26.07, 24.63, 21.73, 30.19, 14.12; m/z (CI, CH₄) 374(M⁺+1, 100%), 356(54), 338(42), 328(38), 309(12), 253(16), 221(10), 119(16). Anal. Calc. for C₂₂H₃₁NO₄: C, 70.75; H, 8.37; N, 3.75; Found; C, 70.78; H, 8.82; N, 3.75. |
| 37 | —NR³R⁴ (10α-isomer) | —H | 2-F benzyl | White solid. M.p. 47.4–48.7° C., $[\alpha]_D^{20}$ −16.9° (c 1.46/CHCl₃); $\nu_{max}$ (film) 3336, 2924, 2872, 1584, 1486, 1454, 1376, 1226, 1196, 1158, 1116, 1056, 1042, 1014, 994, 926, 878, 826, 756; $\delta_H$ 6.99–7.50(4H, m, Ar—H), 5.34(1H, s, H-12), 4.21(1H, d, J=14.5Hz, H-1'), 4.15(1H, d, J=6.72 Hz, H-10), 3.99(1H, d, J=14.5Hz, H-1'), 2.35–2.45(2H, m), 0.90–2.08(10H, m), 1.47(3H, s, H-14), 0.98(3H, d, J=5.99 Hz, H-16), 0.94(3H, d, J=7.16Hz, H15); $\delta_C$ 129.63(d, J=4.79Hz), 127.94(d, J=8.05Hz), 123.64(d, J=3.40Hz), 114.89 (d, J=21.6Hz), 103.90, 91.35, 86.03, 80.59, 51.69, 45.86, 41.96(d, J=3.53 Hz), 37.26, 36.28, 34.08, 32.66, 26.02, 24.62, 21.72, 20.17, 14.00; $\delta_F$ −120; m/z (CI, CH4) 392(M⁺+1, 24%), 374(46), 346 (100), 328(34), 267(2), 221(4), 209 (6), 165(82), 154(50), 109(42). Anal. Calcd. for C₂₂H₃₀NO₄F: C, 67.50; H, 7.72; N, 3.58; found C, 67.75, H, 7.92; N, 3.49. |
| 38 | —NR³R⁴ (10α-isomer) | —H | 3,5-(CF₃)₂ benzyl | Colourless oil. M.p. 51.0–52.8° C.; $[\alpha]_D^{20}$ −27° (c 0.027 CHCl₃); $\delta_H$ 7.88(2H, brs, Ar—H), 7.56(1H, brs, Ar—H), 5.31(1H, s, H-12), 4.24(1H, d, J=15.1Hz, H-1'), 4.12(1H, d, J=15.1Hz, H-1'), 4.06(1H, d, J=9.82Hz, H-10), 2.34–2.45(2H, m), 0.90–2.09(10H, m), 1.47(3H, s, H-14), 0.98(3H, d, J=7.26Hz, H-15), 0.97(3H, d, J=4.94Hz, H16); $\delta_F$ −64.1; m/z (CI, CH₄) 510(M⁺+1, 48%), 490(100), 464(74), 441(38), 283(24), 267(30), 244(10), 221(20), 163(22). Anal. Calcd. for C₂₄H₂₉NO₄F₆: C, 56.58; H, 5.74; N, 2.75; found: C, 56.75, H, 5.76; N, 2.70. |
| 39 | —NR³R⁴ (10α-isomer) | —H | —ⁿC₃H₇ | White solid. M.p. 96.1–97.3° C. (changed colour before melting); $[\alpha]_D^{20}$ +24.8° (c 0.33/CHCl₃); $\nu_{max}$ (film) 3304, 2952, 2924, 2870, 1492, 1454, 1378, 1208, 1160, 1118, 1042, 1012, 974, 942, 922, 878, 844, 828, 754; $\delta_H$ 5.31(1H, s, H-12), 4.11(1H, d, J=9.78Hz, H-10), 2.95(1H, ddd, J=11.4, 8.07, 6.55Hz, CH2NH), 2.61(1H, ddd, J=11.4, 8.07, 6.45Hz, CH₂NH), 2.26–2.43 (2H, m), 2.03(1H, ddd, J=14.5, 4.54, 2.49Hz), 1.84–1.93(1H, m), 1.00–1.83 (10H, m), 1.44(3H, s, H-14), 0.97(3H, d, J=6.10Hz, H-16), 0.92(3H, t, J=7.36 Hz, CH3), 0.89(3H, d, J=7.18Hz, H-15); |

TABLE I-continued (X = H; Z = O)

$\delta_C$ 103.82, 91.34, 86.17, 51.69, 46.27, 45.88, 37.27, 36.27, 34.10, 32.49, 26.04, 24.61, 23.49, 21.72, 20.19, 14.03, 11.62; m/z (CI, CH$_4$) 326(M$^+$+1, 100%), 308(56), 280(48), 221(16), 163(18). Anal. Calcd. for C$_{18}$H$_{13}$NO$_4$: C, 66.43; H, 9.60; N, 4.36; Found: C, 66.17, H, 9.68; N, 4.20.

| 40 | morpholino (10α-isomer) | — | — | White solid. M.p. 121.2° C.; [α]$_D^{20}$ +15.3° (c 0.30/CHCl$_3$); ν$_{max}$ (film) 2924, 2850, 1450, 1376, 1294, 1258, 1202, 1158, 1110, 1056, 984, 930, 880, 846, 826, 744; δ$_H$ 5.29(1H, s, H-12), 3.99(1H, d, J=10.23Hz, H-10), 3.63–3.76(4H, m, O(CH$_2$)$_2$), 2.96–3.03(2H, m, CH$_2$NCH$_2$), 2.64–2.71(2H, m, CH$_2$NCH$_2$), 2.53–2.61(1H, m, H-9), 2.31–2.41(1H, m), 1.00–2.06(10H, m), 1.41(3H, s, H-14), 0.96(3H, d, J=6.14 Hz, H-16), 0.83(3H, d, J=7.18Hz, H-15); δ$_C$ 103.74, 91.48, 90.51, 80.16, 67.25, 51.57, 47.52, 45.66, 37.25, 36.16, 34.14, 28.04, 25.84, 24.62, 21.50, 20.14, 13.25; m/z (EI) 353(M+, 6), 294(4), 236 (4), 221(16), 209(12), 163(14), 127 (32), 116(100), 88(24). Anal. Calcd. for C$_{19}$H$_{31}$NO$_5$: C, 64.56; H, 8.84; N, 3.96%; Found: C, 64.67; H, 9.10; N, 3.90. |
| --- | --- | --- | --- | --- |
| 41 | —NR$^3$R$^4$ (10α-isomer) | —C$_2$H$_5$ | —C$_2$H$_5$ | White solid. δ$_H$ 5.37(1H, s, H-12), 4.76 (d, J=7.54Hz, H-10), 2.80–3.03(4H, m, N(CH$_2$CH$_3$)$_2$), 2.29–2.44(1H, m, H-9), 0.94–1.89(11H, m), 1.53(3H, s, H-14), 1.14(6H, dd, J=7.20, 7.12Hz, N(CH$_2$CH$_3$)$_2$), 1.04(3H, d, J=7.23Hz, H-15), 0.91(3H, d, J=5.72Hz, H-16); δ$_C$ 105.33, 96.11, 81.43, 51.68, 45.23, 41.48, 35.12, 34.52, 33.96, 29.56, 23.77, 22.24, 21.88, 18.52, 15.56, 11.50. m/z (CI, CH$_4$): 340(M$^+$+1, 52%), 251(100), 221(26). |
| 42 | indolinyl (10α-isomer) | — | — | White solid. M.p. 147.8–148.2° C.; [α]$_D^{20}$ −11.6° (c 0.19/CHCl$_3$); ν$_{max}$ (film) 2926, 2872, 1606, 1488, 1462, 1376, 1258, 1200, 1158, 1126, 1040, 1010, 926, 880, 828, 746, 718; δ$_H$ 7.03–7.09(2H, m, Ar—H), 6.60–6.71(2H, m, Ar—H), 5.44(1H, s, H-12), 4.98(1H, d, J=10.4Hz, H-10), 3.79(1H, apparent dt, J=10.4, 9.08Hz, ArCH$_2$), 3.56(1H, apparent dt, J=9.08, 4.36Hz, ArCH$_2$), 2.94–3.12(2H, m, NCH$_2$), 2.67–2.79(1H, m, H-9), 2.39(1H, ddd, J= 14.3, 13.3, 3.94Hz), 2.03(1H, ddd, J= 14.5, 4.73, 2.97Hz), 1.75–1.95(4H, m), 1.06–1.69(6H, m), 1.38(3H, s, H-14), 1.00(3H, d, J=6.17Hz, H-16), 0.94(3H, d, J=7.16Hz, H-15); δ$_C$ 150.51, 130.18, 126.92, 124.57, 118.19, 107.47, 103.90, 91.46, 81.53, 80.05, 51.58, 45.61, 44.83, 37.28, 36.20, 34.12, 29.75, 27.99, 25.83, 24.61, 21.51, 20.16, 13.30; m/z (CI, CH$_4$) 386(M$^+$+1, 100), 340(50), 326(14), 267 (6). Anal. Calcd. for C$_{23}$H$_{11}$NO$_4$: C, 71.66; H, 8.10; N, 3.63; Found: C, 71.45; H, 8.07; N, 3.57. |

TABLE I-continued (X = H; Z = O)

| | | | | |
|---|---|---|---|---|
| 43 | 1,2,3,4-tetrahydro-isoquinolinyl<br>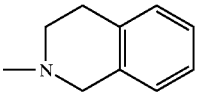<br>(10α-isomer) | — | — | White solid. M.p. 125.3–126.6° C.; [α]$_D^{20}$ +14.7° (c 0.19/CHCl$_3$); ν$_{max}$ (film) 2924, 2870, 1452, 1376, 1278, 1200, 1154, 1130, 1100, 1040, 1014, 982, 926, 880, 826, 742; δ$_H$ 7.07–7.15(4H, m, Ar—H), 5.36(1H, s, H-12), 4.26(1H, d, J=10.2Hz, H-10), 4.20(1H, d, J=15.2Hz, ArCH$_2$N), 3.97(1H, d, J=15.2Hz, ArCH$_2$N), 3.26–3.36(1H, m, ArCH$_2$), 2.70–3.00(4H, m, 3H—CH$_2$CH$_2$N & 1H), 2.40(1H, ddd, J= 14.4, 13.6, 3.93Hz), 2.00–2.07(1H, m), 1.86–1.95(1H, m), 1.71–1.81(2H, m), 1.19–1.65(4H, m), 1.41(3H, s, H-14), 1.02–1.12(1H, m), 0.99(3H, d, J=6.09 Hz, H-16), 0.87(3H, d, J=7.19Hz, H-15); δ$_C$ 135.74, 134.94, 128.55, 126.59, 125.45, 125.21, 103.76, 91.61, 90.60, 80.31, 51.64, 49.18, 45.82, 45.65, 37.29, 36.21, 34.20, 29.89, 28.66, 25.88, 24.67, 21.53, 20.19, 13.46; m/z (CI, CH$_4$) 400 (M$^+$+1, 100), 398(22), 354(54), 340(20), 267(4), 162(44), 134(14). Anal. Calcd. for C$_{24}$H$_{33}$NO$_4$: C, 72.15; H, 8.33; N, 3.51; found: C, 71.98; H, 8.36; N, 3.36. |
| 44 | —NR$^3$R$^4$<br>(10α,1'S-isomer) | —H | —CH(CH$_3$)phenyl | White solid. M.p. 55.4–57.5° C.; δ$_H$ 7.20–7.42(5H, m, Ar—H), 5.13(1H, s, H-12), 4.45(1H, q, J=6.62Hz, H-1'), 3.77(1H, d, J=9.79Hz, H-10), 2.23–2.43 (2H, m), 2.03(1H, ddd, J=14.5, 4.73, 3.08Hz), 0.96–1.88(9H, m), 1.48(3H, s, H-14), 1.31(3H, d, J=6.62Hz, CH$_3$), 0.91(3H, d, J=5.94Hz, H-16), 0.91(3H, d, J=7.14Hz, H-15); δ$_C$ 146.07, 128.01, 126.96, 126.39, 103.81, 91.38, 83.80, 80.70, 52.37, 51.71, 45.82, 37.08, 36.30, 33.95, 33.40, 26.11, 25.53, 24.57, 21.64, 20.14, 14.22; m/z (CI, CH$_4$) 388(M$^+$+1, 100%), 370(22), 342(64), 267(8), 221 (10). Anal. Calcd. for C$_{23}$H$_{33}$NO$_4$: C, 71.29; H, 8.58; N, 3.61; found: C, 71.20; H, 8.72; N, 3.62. |
| 45 | —NR$^3$R$^4$<br>(10α,1'R-isomer) | —H | —CH(CH$_3$)phenyl | White solid. δ$_H$ 7.20–7.43(5H, m, Ar—H), 5.36(1H, s, H-12), 4.44(1H, q, J=6.41 Hz, H-1'), 4.31(1H, d, J=9.70Hz, H-10), 2.21–2.40(2H, m), 2.00–2.08(1H, m), 1.02–1.95(9H, m), 1.45(3H, s, H-14), 1.31(3H, d, J=6.41Hz, CH$_3$), 0.99(3H, d, J=6.18Hz, H-16), 0.93(3H, d, J= 7.16Hz, H-15); δ$_C$ 147.01, 128.06, 127.01, 126.59, 103.85, 91.33, 83.03, 80.56, 51.72, 51.51, 45.92, 37.29, 36.28, 34.14, 33.09, 26.01, 24.66, 22.35, 21.83, 20.21, 14.22; m/z (CI, CH$_4$) 388(M$^+$+1, 100%), 370 (56), 342(42), 309(30), 267(18), 253 (32), 221(20), 119(34). Anal. Calcd. for C$_{23}$H$_{33}$NO$_4$: C, 71.29; H, 8.58; N, 3.61; found: C, 71.22; H, 8.73; N, 3.49. |
| 46 | —NR$^3$R$^4$<br>(10α,1'R-isomer) | —H | —CH(CO—OCH$_3$)phenyl | Colourless oil. ν$_{max}$ (Neat): 3342(ν$_{NH}$), 2926, 2827, 1742(ν$_{C=O}$, ester), 1602, 1494, 1452, 1376, 1246, 1198, 1158, 1130, 1042, 1014, 994, 928, 880, 844, 826, 736, 700 cm$^{-1}$; $^1$H nmr (300MHz, CDCl$_3$) δ$_H$ 7.21–7.50 (5H, m, Ar—H), 5.13(1H, s, H-12), 4.94 (1H, s, H-2'), 3.85(1H, d, — J=9.81Hz, H-10), 3.65(3H, s, OMe), 2.74 (1H, br.s., NH), 2.35(1H, m, H-9), 1.05–2.07(11H, m, H-2 × 2, H-3 × 2, H-4, H-5, H-6 × 2, H-7 × 2, H-8), 1.47(3H, s, 1-CH$_3$), 0.90(6H, d × 2, signals overlap, 5-CH$_3$, 9-CH$_3$) ppm; m/z (CI, CH$_4$) 432(M$^+$+1, 96%), 386(100), 372(44), 312(14), 267 (24), 221(28), 166(96). Anal. Calcd. for C$_{24}$H$_{33}$NO$_6$: C, 66.80; H, 7.71; N, 3.24; Found: C, 66.98; H, 7.53; N, 3.05. |

TABLE I-continued

(X = H; Z = O)

| | | | | |
|---|---|---|---|---|
| 47 | —NR³R⁴ (10α,1'S-isomer) | —H | —CH(CO—OCH₃)phenyl | Colourless oil; ¹H nmr (300 MHz, CDCl₃) $\delta_H$ 7.28–7.51(5H, m, Ar—H), 5.22(1H, s, H-12), 5.04(1H, s, H-2'), 4.28(1H, d, J 9.81Hz, H-10), 3.68(3H, s, OMe), 2.57 (1H, br.s., NH), 2.29–2.44(1H, m, H-9), 0.96–2.44(1H, m, H-2 × 2, H-3 × 2, H-4, H-5, H-6 × 2, H-7 × 2, H-8), 1.43(3H, s, 1-CH₃), 0.97(3H, d, J 6.11Hz, H-15), 0.90(3H, d, J 7.16Hz, H-16)ppm; m/z (CI, CH₄) 432(M⁺+1, 90%), 386(100), 372(50). Anal. Calcd. for C₂₁H₁₁NO₆: C, 66.17, H, 7.48, N, 3.35; found C, 65.57; H, 7.57; N, 3.36. |
| 48 | —NR³R⁴ (10α-isomer) | —H | 4-(CO—OCH₃)phenyl | White solid. M.p. 117.7–118.5° C.; $[\alpha]_D^{20}$ −84.1 (c 0.82/CHCl₃); $\nu_{max}$ (film) 3344, 2948, 1710, 1608, 1528, 1434, 1378, 1270, 1178, 1110, 1040, 1012, 926, 878, 842, 768; $\delta_H$ 6.66–7.76(4H, m, Ar—H), 5.46(1H, s, H-12), 5.06(1H, d, J=9.96Hz, NH), 4.88(1H, dd, J=9.89, Hz, H-10), 3.83(3H, s, OMe), 2.56–2.60(1H, m), 2.33–2.42(1H, m), 0.85–2.04(10H, m), 1.39(3H, s, H-14), 0.99(3H, d, J=6.09Hz, H-15), 0.92 (3H, d, J=7.11Hz, H-16); $\delta_C$: 167.06, 149.99, 131.04, 119.64, 113.01, 104.30, 91.21, 80.49, 80.02, 51.70, 51.40, 45.67, 37.34, 36.20, 34.04, 32.50, 25.92, 24.66, 21.84, 20.94, 20.22, 14.10, 13.67; m/z (CI, CH₄) 418(M⁺+1, 32), 400(6), 372 (100), 358(8), 221(28), 152(26). Anal. Calcd. for C₂₃H₃₁NO₆: C, 66.17, H, 7.48, N, 3.35; found C, 65.57; H, 7.57; N, 3.36. |
| 49 | —NR³R⁴ (α-isomer) | —H | cyclopentyl | White solid. M.p. 114.1–114.9° C.; $[\alpha]_D^{20}$: −1.6° (c 0.98/CHCl₃); $\nu_{max}$ (film) 3314, 2950, 2870, 1446, 1376, 1198, 1154, 1114, 1098, 1042, 1014, 976, 944, 924, 878, 860, 826, 754; $\delta_H$: 5.29(1H, s, H-12), 4.08(1H, d, J=9.76Hz, H-10), 3.52–3.60(1H, m, H-1'), 2.23–2.41(2H, m), 1.24–2.05(17H, m), 1.43(3H, s, H-14), 0.84–1.11(1H, m), 0.96(3H, d, J=6.15Hz, H-15), 0.85(3H, d, J=7.17Hz, H-16); $\delta_C$ 103.91, 91.44, 85.08, 80.77, 54.33, 51.84, 46.01, 37.38, 36.40, 34.23, 34.20, 33.11, 32.70, 26.17, 24.74, 23.63, 21.89, 20.31, 14.30; m/z (CI, CH₄) 352(M⁺+1, 14), 334(10), 306 (100), 288(14), 251(4), 221(4), 125 (10); Anal. Calcd. for C₂₀H₃₃NO₄: C, 68.34; H, 9.46; N, 3.98; found: C, 67.89; H, 9.46; N, 3.92. |
| 50 | —NR³R⁴ (α-isomer) | —H | cyclohexyl | White solid. $\delta_H$ 5.28(1H, s, H-12), 4.17 (1H, d, J=9.69Hz, H-10), 2.93–3.00(1H, m H-1'), 2.16–2.41(2H, m), 0.84–2.03 (19H, m), 1.42(3H, s, H-14), 0.95(3H, d, J=6.11Hz, H-15), 0.85(3H, d, J=7.18Hz, H-16); $\delta_C$ 103.87, 91.36, 83.36, 80.70, 51.84, 50.94, 46.04, 37.36, 36.38, 34.58, 34.21, 33.18, 32.79, 26.29, 26.12, 24.75, 24.71, 24.27, 21.88, 20.29, 14.29, 14.39; m/z (CI, CH₄) 366(M⁺+1, 10), 348(10), 329 (100), 318(12), 221(4), 139(8); Anal. Calcd. for C₂₁H₃₅NO₄: C, 69.01; H, 9.65; N, 3.83; found: C, 68.85, H, 9.85; N, 3.80. |

TABLE I-continued (X = H; Z = O)

| | | | | |
|---|---|---|---|---|
| 51 | N-methyl-piperazino<br>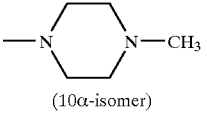<br>(10α-isomer) | — | — | Brownish yellow solid. M.p. 112–114° C.; $[\alpha]_D^{20}$ +12.95° (c. 0.0149 in CHCl$_3$); $\nu_{max}$ (Neat): 2934, 2872, 2792, 1454, 1376, 1286, 1226, 1192, 1162, 1132, 1102, 1054, 1014, 984, 926, 880, 830 cm$^{-1}$; $^1$H nmr (300 MHz, CDCl$_3$) $\delta_H$ 5.26(1H, s, H-12), 4.02 (1H, d, J 10.20Hz, H-10), 3.03(2H, m, H-6'a, H-6'b), 2.70(2H, m, H-2'a, H-2'b), 2.59(1H, m, H-9), 2.30–2.50(5H, m, H-8, H-3'a, H-3'b, H-5'a, H-5'b), 2.28(3H, s, N—Me), 1.18–2.05(10H, m, H-2a, H-2b, H-3a, H-3b, H-4, H-5, H-6a, H-6b, H-7a, H-7b), 1.36(3H, s, 1-CH$_3$), 0.94(3H, d, J 6.12Hz, 9-CH$_3$), 0.80(3H, d, J 7.17Hz, 5-CH$_3$) ppm; $\delta_C$ 104.46, 92.16, 90.96, 90.98, 56.18, 52.36, 46.82, 38.05, 36.96, 34.97, 29.16, 26.55, 25.46, 22.30, 20.96, 14.03 m/z (CI, CH$_4$) 367([M+1]$^+$, 100), 321([M−3CH$_3$]$^+$, 26). |
| 52 | 4-vinylphenyl<br>(10β-isomer) | — | — | White solid. $[\alpha]_D^{22}$ −64.6° (c 0.028/CHCl$_3$); $\nu_{max}$ (film) 2948, 2876, 1630, 1512, 1452, 1406, 1376, 1200, 1116, 1074, 1010, 944, 904, 882, 844, 788, 756; $\delta_H$: 7.37(2H, d, J=8.26Hz, Ar—H), 7.27(2H, d, J=8.26Hz, Ar—H), 6.71(1H, dd, J=17.62, 10.90Hz, vinyl-H), 5.69–5.76(2H, m, vinyl-H, H-10), 5.57(1H, s, H-12), 5.20(1H, d, J=10.90Hz, vinyl-H), 2.71–2.78(1H, m), 2.28–2.38(1H, m), 1.17–2.09(9H, m), 1.38 (3H, s, H-14), 0.83–0.99(1H, m), 0.98 (3H, d, J=5.74Hz, H-15), 0.54(3H, d, J=7.67Hz, H-16); $\delta_C$: 140.91, 136.75, 135.74, 126.36, 125.72, 113.09, 102.40, 90.89, 81.24, 73.07, 51.58, 43.58, 37.58, 36.73, 34.26, 32.19, 25.80, 24.98, 24.80, 19.97, 13.75. Anal. Calcd. for C$_{23}$H$_{30}$O$_4$: C, 74.56; H, 8.16; found: C, 74.58; H, 8.26. |
| 53 | 4-Br phenyl<br>(10β-isomer) | — | — | White rectangular crystal. M.p. 156–159° C.; $[\alpha]_D^{20.4}$ −45.14° (c 0.0216 in CHCl$_3$); $\nu_{max}$ (Nujol): 2924, 1492, 1454, 1374, 1112, 1008, 942, 902, 882, 840, 780 cm$^{-1}$; $^1$H nmr (300MHz, CDCl$_3$) $\delta_H$ 7.43(2H, d, J 8.40Hz, H-3', H-5'), 7.19(2H, d, J 8.40 Hz, H-2', H-6'), 5.70(1H, d, J 6.60Hz, H-10), 5.55(1H, s, H-12), 2.72(1H, m, H-9), 2.33(1H, m, H-8), 1.19–2.10(10H, m, H-2a, H-2b, H-3a, H-3b, H-4, H-5, H-6a, H-6b, H-7a, H-7b), 1.40(3H, s, 1-CH$_3$), 0.98(3H, d, J 5.70Hz, 9-CH$_3$), 0.48 (3H, d, J 7.80Hz, 5-CH$_3$) ppm; m/z (CI, CH$_4$) 453([M(Br$^{81}$)+2CH$_4$]$^+$, 18), 451 ([M(Br$^{79}$)+2CH$_4$]$^-$, 20), 425 ([M(Br$^{81}$)+1]$^+$, 51), 423([M(Br$^{79}$)+1]$^+$, 53), 407(40), 405(32), 392(35), 390(48), 379(100), 377(88), 335(20), 333(28), 267(32), 221(41), 209(78), 191(78), 191(26), 163(59). |
| 54 | 4-Cl phenyl<br>(10β-isomer) | — | — | White rectangular crystal. M.p. 141–146° C.; $[\alpha]_D^{20.4}$ −10.35° (c 0.0508 in CHCl$_3$); $\nu_{max}$ (Nujol): 2924, 1494, 1456, 1374, 1114, 1008, 942, 902, 840, 782 cm$^{-1}$; $^1$H nmr (300MHz, CDCl$_3$) $\delta_H$ 7.30(2H, d, J=8.16Hz, H-3', H-5'), 7.24(2H, d, J=8.16Hz, H-2', H-6'), 5.69(1H, d, J 6.60Hz, H 10), 5.55(1H, m, H 12), 2.71 (1H, m, H-9), 2.32(1H, m, H-8), 1.21–2.08(10H, m, H-2a, H-2b, H-3a, H-3b, H-4, H-5, H-6a, H-6b, H-7a, H-7b), 1.36(3H, s, 1-CH$_3$), 0.98(3H, d, J 5.76Hz, 9-CH$_3$), 0.49 (3H, d, J 7.68Hz, 5-CH$_3$) ppm; $\delta_C$ 140.37, 132.75, 128.66, 128.31, 103.10, 91.64, 81.91, 73.28, 52.23, 44.16, 38.28, 37.41, 34.93, 32.80, 26.47, 25.53, 20.63, 14.36; m/z (CI, CH$_4$) 407([M(Cl$^{37}$)+2CH$_4$]$^+$, 6), 405 ([M(Cl$^{35}$)+2CH$_4$]$^+$, 5), 379([M(Cl$^{37}$)—$^+$]$^+$, 97). |

TABLE I-continued (X = H; Z = O)

| | | | | |
|---|---|---|---|---|
| | | | | 377([M(Cl³⁴)−1]⁺, 100), 355(14), 333 (26), 182(12). Anal. calc. for $C_{23}H_{22}O_4Cl$ C, 66.57; H, 7.18; found C, 66.42; H, 7.05. |
| 55 | 9-anthryl (10β-isomer) | — | — | White solid. $\delta_H$ 9.00–9.05(1H, m, Ar—H), 8.31–8.41(2H, m, Ar—H), 7.05–8.04(2H, m, Ar—H), 7.39–7.57(4H, m, Ar—H), 7.23(1H, d, J=7.51Hz, H-10), 5.81(1H, s, H-12), 3.10–3.23(1H, m), 0.86–2.49(11H, m), 1.39(3H, s, H-14), 1.09(3H, d, J=5.81 Hz, H-15), 0.57(3H, d, J=7.72Hz, H-16); $\delta_C$: 134.12, 131.70, 131.05, 130.88, 129.59, 129.19, 128.73, 128.47, 127.61, 126.05, 124.55, 124.51, 124.32, 123.71, 102.64, 91.22, 81.42, 72.62, 51.50, 44.18, 37.69, 36.87, 34.33, 33.02, 25.71, 25.09, 25.00, 19.94, 13.81. |
| 56 | 9-phenanthryl (10β-isomer) | — | — | White solid. M.p. 89–891° C.; $[\alpha]_D^{20}$: −68.8° (c 0.016 CHCl₃); $v_{max}$ (film) 2922, 2874, 2362, 1498, 1450, 1376, 1246, 1220, 1110, 1040, 1010, 956, 930, 906, 886, 832, 794, 748, 726; $\delta_H$: 8.68–8.81(2H, m, Ar—H), 7.91–8.10(3H, m, Ar—H), 7.57–7.72 (4H, m, Ar—H), 6.50(1H, d, J=6.54Hz, H-10), 5.75(1H, s, H-12), 3.06–3.19(1H, m), 2.37–2.48(1H, m), 2.00–2.16(3H, s), 1.73–1.84(2H, m), 0.86–1.60(5H, m), 1.41 (3H, s, H-14), 1.06(3H, d, J=5.67Hz, H-15), 0.39(3H, d, J=7.61Hz, H-16); $\delta_C$: 135.21, 131.68, 130.14, 129.96, 129.59, 128.84, 126.66, 126.52, 126.04, 126.01, 123.84, 123.68, 123.19, 122.33, 102.47, 91.34, 81.42, 69.92, 51.45, 43.77, 37.71, 36.89, 34.27, 31.55, 25.79, 25.11, 24.95, 19.96, 13.22; m/z (CI, CH₄) 445(M⁺+1, 22), 444(100), 398(40), 384(16), 352(16), 328(44), 267(6), 218(84), 203(48), 178 (60), 163(44), 138(70), 107(62). |
| 57 | 2-OCH₃ phenyl (10β-isomer) | — | — | White solid. M.p. 61° C.; $[\alpha]_D^{20}$: −14.4° (c 0.049 CHCl₃); $v_{max}$ (film) 2928, 2874, 1590, 1492, 1462, 1374, 1284, 1240, 1178, 1110, 1102, 1052, 1010, 944, 882, 854, 754; $\delta_H$ 6.83–7.50(4H, m, Ar—H), 5.94(1H, d, J=6.65, Hz, H-10), 5.58(1H, s, H-12), 3.84(3H, s, OCH₃), 2.86–2.99(1H, m, H-9), 2.30–2.40(1H, m), 1.19–2.11(10H, m), 1.39(3H, s, H-14), 1.01(1H, d, J=5.77 Hz, H-16), 0.43(1H, d, J=7.64Hz, H-15); $\delta_C$ 134.85, 127.00, 126.37, 120.02, 109.19, 90.86, 68.63, 55.19, 51.30, 43.39, 37.53, 36.72, 34.21, 29.87, 25.68, 24.97, 24.75, 19.83, 13.45; m/z (CI, CH₄) 375(M⁺+1, 12%), 374(M⁺, 16), 342(100), 329(48), 311(14), 284(28), 182(56), 148(76), 137(60), 121(48): Anal. Calcd. for $C_{22}H_{30}O_5$: C, 70.56; H, 8.07; found: C, 70.78; H, 8.28. |
| 58 | 2,4-(OCH₃)₂phenyl (10β-isomer) | — | — | White snow-like crystal. M.p. 62° C.; $[\alpha]_D^{20.5}$ −64.21° (c. 0.0114 in CHCl₃); (Found C, 68.55; H, 8.14 $C_{23}H_{32}O_6$ requires C, 68.29; H, 7.97%); $v_{max}$ (Nujol): 2920, 1614, 1590, 1506, 1464, 1376, 1286, 1258, 1208, 1156, 1120, 1040, 1010, 946, 880, 832, 780, 726 cm⁻¹; ¹H nmr (300MHz, CDCl₃) $\delta_H$ 7.33(1H, d, J 8.40Hz, H-6'), 6.47 (1H, dd, J 8.40, 2.40Hz, H-5'), 6.42(1H, d, J 2.40Hz, H-3'), 5.84(1H, d, J 6.60 Hz, H-10), 5.54(1H, s, H-12), 3.80, 3.79 (6H, 2xs, 2xOMe), 2.84(1H, m, H-9), 2.32 (1H, m, H-8), 1.20–2.10(10H, m, H-2a, H-2b, H-3a, H-3b, H-4, H-5, H-6a, H-6b, H-7a, H-7b), 1.37(3H, s, 1-CH₃), 1.00(3H, d, J 5.70Hz, 9-CH₃), 0.40(3H, d, J 7.50 Hz, 5-CH₃) ppm; m/z (CI, CH₄) 405([M+1]⁺, 15), 359([−3CH₃]⁺, 100), 317(6), 275 |

TABLE I-continued (X = H; Z = O)

| | | | | |
|---|---|---|---|---|
| 59 | 2,4,6-(OCH$_3$)$_3$ phenyl (10β-isomer) | — | — | (28), 221(8), 154(22). Anal. Calc. for C$_{23}$H$_{32}$O$_6$: C, 68.29; H, 7.97%; found C, 68.55; H, 8.14; C, 68.47; H, 8.37. Colourless oil. [α]$_D^{22}$ +10.6° (c 0.016/ CHCl$_3$); ν$_{max}$ (film) 2938, 1608, 1456, 1204, 1154, 1126, 1006, 954; δ$_H$: 6.16(1H, d, J=8.09Hz, H-10), 6.13(2H, s, Ar—H), 5.52 (1H, s, H-12), 3.81(3H, s, OMe), 3.78 (2x3H, s, OMe), 2.64–2.72(1H, m), 2.29– 2.38(1H, m), 1.97–2.08(2H, m), 1.68–1.84 (4H, m), 1.20–1.57(3H, m), 1.40(3H, s, H-14), 0.84–1.11(1H, m), 1.00(3H, d, J=5.73Hz, H-15), 0.72(3H, d, J=7.70Hz, H-16); m/z (CI, CH$_4$) 435(M$^+$+1, 10), 417 (8), 389(100), 371(6), 347(10), 329 (16), 221(8): Anal. Calcd. for C$_{24}$H$_{34}$O$_7$; C, 66.34: H, 7.89; found: C 66.57; H, 8.04. |
| 60 | 2,4,6-(CH$_3$)$_3$ phenyl (10β-isomer) | — | — | Colourless oil. [α]$_D^{22}$ +13.7 (c 0.019/ CHCl$_3$); ν$_{max}$ (film) 2938, 2874, 1452, 1376, 1208, 1106, 1076, 1008, 958, 942, 896, 880, 848, 780, 756, 724; δ$_H$: 6.81(2H, s, Ar—H), 6.05(1H, d, J=7.57Hz, H-10), 5.55 (1H, s, H-12), 2.74–2.85(1H, m), 2.48 (3H, s, Me), 2.26–2.40(1H, m), 2.32(3H, s, Me), 2.27(3H, s, Me), 2.05–2.11(2H, m), 1.64–1.90(4H, m), 1.29–1.50(3H, m), 1.41(3H, s, H-14), 0.84–1.04(1H, m), 1.03(3H, d, J=5.91Hz, H-15), 0.64(3H, d, J=7.84Hz, H-16); δ$_C$: 137.22, 135.56, 135.21, 133.52, 130.81, 128.37, 102.30, 90.71, 80.94, 71.82, 51.32, 43.92, 37.59, 36.79, 34.24, 30.44, 25.72, 25.04, 24.46, 22.28, 20.70, 20.63, 19.87, 13.22; m/z (CI, CH$_4$) 387(M$^+$+1, 6), 386(8), 385(10), 341(100), 327(8), 299(8), 267(14), 221 (10), 209(4), 163(8), 133(8); Anal. Calcd. C$_{24}$H$_{34}$O$_4$: C, 74.58, H, 8.87; found: C, 74.49; H, 8.86. |
| 61 | 2,4,5-(CH$_3$)$_3$ phenyl (10β-isomer) | — | — | Colourless Oil. M.P. 141° C.; [α]$_D^{20}$: 55.6° (C 0.068/CHCl$_3$); ν$_{max}$ (film) 2922, 2874, 1502, 1452, 1374, 1278, 1220, 1202, 1180, 1120, 1100, 1056, 1040, 1000, 978, 954, 934, 896, 880, 820, 754; δ$_H$: 7.32(1H, s, Ar—H), 6.99(1H, s, Ar—H), 5.94(1H, d, J=6.71Hz, H-10), 5.67(1H, s, H-12), 2.80–2.90(1H, m), 2.38–2.48(1H, m), 2.33 (2x3H, s, Me), 2.31(3H, s, Me), 2.10–2.19 (2H, m), 1.78–2.00(3H, m), 1.40–1.55(4H, m), 1.47(3H, s, H-14), 0.97–1.11(1H, m), 1.11(3H, d, J=5.75Hz, H-15), 0.55(3H, d, J=7.68Hz, H-16); δ$_C$: 136.62, 134.02, 133.13, 131.04, 130.76, 127.09, 102.11, 91.04, 81.07, 70.00, 51.33, 43.49, 37.57, 36.73, 34.23, 29.89, 25.57, 25.01, 24.81, 19.89, 19.17, 18.73, 13.65; m/z (CI, CH$_4$) 387(M$^+$+1, 10), 386(M$^+$, 44), 354(60), 341 (84), 296(6), 282(18), 109(20, 182 (28), 160(100), 149(56), 133(38), 121 (30); Anal. Calcd for C$_{24}$H$_{34}$O$_4$: C, 74.58; H, 8.87; found: C, 74.63, H, 8.73. |
| 62 | 4-COOH phenyl (10β-isomer) | — | — | White solid. [α]$_D^{20}$ -63.2° (c 0.019/ CHCl$_3$); ν$_{max}$ (film) 2954, 2878, 2670, 2546, 2252, 1688, 1612, 1578, 1512, 1452, 1424, 1376, 1314, 1286, 1222, 1208, 1178, 1116, 1074, 1056, 1040, 1012, 980, 968, 954, 944, 908, 882, 854, 824, 802, 766, 732; δ$_H$ 8.09(2H, d, J=8.34Hz, Ar—H), 7.45(2H, d, J=8.34Hz, Ar—H), 5.82(1H, d, J=6.63 Hz, H-10), 5.60(1H, s, H-12), 2.76–2.83 (1H, m), 2.31–2.40(1H, m), 1.23–2.10(9H, m), 1.41(3H, s, H-14), 0.87–1.02(1H, m) 1.01(3H, d, J=5.49Hz, H-15), 0.51(3H, d, J=7.62Hz, H-16); δ$_C$ 171.66, 147.41, 129.71, 127.33, 126.15, 102.29, 90.80, 81.07, 72.74, 51.35, 43.29, 37.42, 36.53, 34.04, 31.94, 29.05, 25.60, 24.67, 19.78, 13.42; m/z (CI, CH$_4$) 389(M$^+$+1, 8), 329 |

TABLE I-continued (X = H; Z = O)

(100), 283(36), 267(20), 219(26), 177 (80), 129(64) Anal. Calcd. for $C_{22}H_{28}O_6$: C, 68.02; H, 7.27; found: C, 67.77; H, 7.31.

| Ex. No. | Y | $R^5$ | Physical data |
|---|---|---|---|
| 63 | —O—CO—$R^5$ | isoquinolin-1-yl 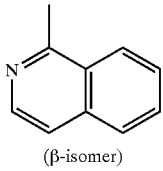 (β-isomer) | White solid. M.p. 167.1–169.3° C. $[\alpha]_D^{20}$ +142° (c 0.37/CHCl$_3$); $\nu_{max}$ (film): 2942, 2870, 1726, 1452, 1376, 1280, 1248, 1226, 1180, 1142, 1102, 1074, 1002, 986, 900, 872, 850, 758; $\delta_H$: 7.67–8.71 (6H, m, Ar—H), 6.66(1H, d, J=3.35Hz, H-10), 5.69(1H, s, H-12), 2.91–3.01(1H, m, H-9), 2.40(1H, ddd, J=13.6, 4.08, 3.87Hz), 1.29–2.08(10H, m), 1.46(3H, s, H-14), 1.04(3H, d, J=7.33Hz, H-14), 0.95(3H, d, J=6.08Hz, H-16); $\delta_C$ 165.01, 141.75, 136.54, 130.32, 128.42, 126.87, 126.40, 126.10, 123.53, 104.25, 96.09, 88.99, 80.63, 52.35, 43.95, 37.18, 36.15, 34.47, 30.22, 25.83, 24.49, 23.68, 20.15, 12.54; m/z (EI) 439(M$^+$, 40), 394(34), 380(44), 354 (64), 336(100), 322(44), 309(46), 299(80). Anal. Calcd. for $C_{25}H_{29}NO_6$: C, 68.32; H, 6.65; N, 3.19; found: C, 68.03; H, 6.90; N, 3.13 |
| 64 | —O—CO—$R^5$ | anthryl 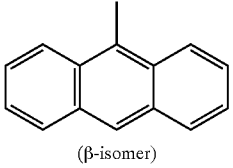 (β-isomer) | White solid. M.p. 131° C.; $[\alpha]_D^{20}$ +49.2° (c 0.73/CHCl$_3$); $\nu_{max}$ (film): 2922, 1732, 1448, 1376, 1196, 1152, 1102, 1076, 984, 896, 876, 844, 738; $\delta_H$: 855(1H, s, Ar—H-10), 8.04–8.15(4H, m, Ar—H), 7.52–7.61(4H, m, Ar—H), 6.91(1H, d, J=3.45Hz, H-10), 5.59 (1H, s, H-12), 3.00–3.10(1H, m, H-9), 2.42(1H, ddd, J=17.5, 13.3, 4.00Hz), 2.08(1H, ddd, J=15.3, 4.77, 2.96Hz), 1.83–1.92(1H, m), 0.76–1.56(8H, m), 1.54(3H, s, H-14), 1.13(3H, d, J=7.39Hz, H-16), 0.84(3H, d, J=6.22Hz, H-15). $\delta_C$: 168.32, 130.83, 129.03, 128.44, 128.09, 126.92, 125.40, 124.75, 104.34, 96.14, 89.08, 89.05, 80.40, 52.19, 43.69, 37.01, 36.14, 34.00, 29.91, 25.87, 24.42, 23.58, 19.93, 12.63; m/z (CI, NH$_3$): 506(M+NH$_4^+$, 24%), 488(M$^+$, 2), 396(48), 379 (100), 284(44), 267(24), 205(6). Anal. Calcd. for $C_{30}H_{32}O_6$: C, 73.75; H, 6.60; found: C, 73.96; H, 6.84 |
| 65 | —O—CO—$R^5$ | acridin-9-yl 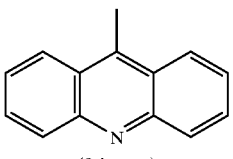 (β-isomer) | White solid. $[\alpha]_D^{20}$ +125° (c 0.15/CHCl$_3$); $\nu_{max}$ (film) 2948, 1738, 1518, 1462, 1378, 1208, 1104, 986, 892, 876, 848, 764; $\delta_H$ 7.59–8.31(8H, m, Ar—H), 6.91(1H, d, J=3.39 Hz, H-10), 5.54(1H, s, H-12), 3.00–3.10(1H, m, H-9), 2.41(1H, ddd, J= 17.3, 13.4, 4.00Hz), 2.08(1H, ddd, J=14.7, 4.67, 2.88 Hz), 1.83–1.92(1H, m), 1.24–1.59(8H, m), 1.53(3H, s, H-14), 1.12(3H, d, J=7.32Hz, H-16), 0.84(3H, d, J=6.22Hz, H-15); $\delta_C$ 168.35, 148.55, 136.90, 130.28, 129.80, 127.16, 124.75, 121.97, 104.45, 96.93, 89.13, 80.27, 52.10, 43.50, 37.02, 36.06, 33.90, 29.82, 25.81, 24.38, 23.58, 19.89, 12.59; m/z (EI): 489(M$^+$, 6%), 266(24), 223(100), 167(42), 195(18). Anal. Calcd. for $C_{29}H_{31}NO_6$: C, 71.15; H, 6.38; N, 2.86; found: C, 70.87; H, 6.46; N, 2.83 |
| 66 | —O—CO—$R^5$ | anthraquinon-2-yl 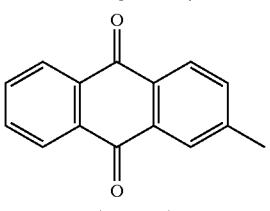 (β-isomer) | Yellow solid. $[\alpha]_D^{20}$ +35.8° (c 0.052/CHCl$_3$); $\nu_{max}$ (film) 2942, 1732, 1678, 1594, 1452, 1378, 1326, 1296, 1266, 1242, 1172, 1102, 1070, 1054, 1032, 1014, 978, 932, 898, 876, 856, 798, 754; $\delta_H$: 7.81–8.88(7H, m, Ar—H), 6.56(1H, d, J=3.34Hz, H-10), 5.62(1H, s, H-12), 2.93–3.03(1H, m, H-9), 2.35–2.45(1H, m), 0.96–2.10(10H, m), 1.44(3H, s, H-14), 1.03 (3H, d, J=5.66Hz, H-15), 1.01(3H, d, J=7.10Hz, H-16); $\delta_C$: 182.33, 181.99, 163.94, 136.12, 135.00, 134.46, 134.40, 133.54, 133.29, 133.26, 128.40, 127.68, 127.36, 127.32, 104.48, 96.43, 88.86, 80.44, 52.32, 43.84, 37.54, 36.14, 24.49, 30.05, 25.80, 24.57, 24.43, 20.23, 14.13, 12.59; m/z (EI): 519(M$^+$, 66), 436(100), 256(66), 221(26), 203(18); Anal. Calcd. for $C_{30}H_{30}O_8$: C, 69.49; H, 5.83; found: C, 69.85; H, 6.07 |
| 67 | —O—CO—$R^5$ | quinolin-3-yl 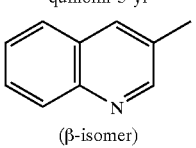 (β-isomer) | White solid. $[\alpha]_D^{22}$ +81.2° (c 0.025/CHCl$_3$); $\nu_{max}$ (film) 2942, 1726, 1620, 1498, 1460, 1376, 1284, 1236, 1196, 1110, 1092, 1072, 1054, 1034, 974, 898, 874, 852, 790, 754; $\delta_H$ 9.41(1H, d, J=1.96Hz, Ar—H), 8.86 (1H, d, J=1.29Hz, Ar—H), 8.17(1H, d, J=8.53Hz, Ar—H), 7.97(1H, d, J=8.18Hz, Ar—H), 7.84–7.89(1H, m, Ar—H), 7.63–7.68(1H, m, Ar—H), 6.61(1H, d, J=3.45Hz, H-10), 5.61(1H, s, H-12), 2.94–3.04(1H, m), 2.30–2.46(1H, m), 1.23–2.09(9H, m), 1.45(3H, s, H-14), 0.88–1.08 (1H, m), 1.01(2x3H, d, J=6.62Hz, H-15, H-16); $\delta_C$ 164.27, 149.83, 149.51, 139.37, 132.10, 129.39, 129.19, 127.59, 126.86, 122.96, 104.51, 96.03, 88.86, 80.45, 52.31, 43.82, 37.58, 36.14, 34.45, 30.05, 25.84, 24.57, 24.48, 20.17, 12.60. |

TABLE I-continued (X = H; Z = O)

| | | | |
|---|---|---|---|
| 68 | —O—CO—R⁵ | quinoxalin-2-yl 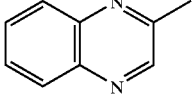 (β-isomer) | White solid. $[\alpha]_D^{22}$ +71.7° (c 0.017/CHCl₃) $\nu_{max}$ (film) 2938, 1728, 1494, 1466, 1364, 1304, 1280, 1230, 1156, 1112, 1096, 1074, 1054, 1034, 1014, 978, 900, 874, 852, 804, 778, 752; $\delta_H$ 9.50(1H, s, Ar—H), 8.19–8.26 (2H, m, Ar—H), 7.86–7.97(2H, m, Ar—H), 6.66(1H, d, J=3.02Hz, H-10), 5.69(1H, s, H-12), 2.96–3.06(1H, m), 0.89–2.48(11H, m), 1.46(3H, s, H-14), 1.01–1.04(6H, m, H-15, H-16); $\delta_C$ 163.09, 144.75, 143.63, 142.52, 141.80, 132.40, 130.93, 130.81, 129.29, 104.51, 96.84, 89.06, 80.58, 52.41, 43.92, 37.57, 36.19, 34.64, 30.22, 25.86, 24.62, 24.14, 20.28, 12.61. |
| 69 | —O—CO—R⁵ | 2-hydroxynaphth-1-yl 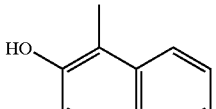 (β-isomer) | White solid. $[\alpha]_D^{20}$ +146° (c 0.024/CHCl₃); $\nu_{max}$ (film) 2942, 1660, 1636, 1600, 1578, 1462, 1412, 1390, 1336, 1272, 1252, 1208, 1160, 1104, 1088, 1072, 1054, 1032, 1014, 976, 964, 926, 898, 874, 850, 796, 772, 716; $\delta_H$ 12.12(1H, s, OH), 11.92(1H, s, OH), 8.52(1H, d, J=8.20Hz, Ar—H), 7.86(1H, d, J=8.01Hz, Ar—H), 7.53–7.73(4H, m, Ar—H), 7.39(1H, d, J=8.79Hz, Ar—H), 6.64(1H, d, J=3.48Hz, H-10), 6.13(1H, d, J=9.81 Hz, H-10), 5.68Hz(1H, s, H-12), 5.64(1H, s, H-12), 3.02–3.12(1H, m), 2.39–2.54(1H, m), 1.88–2.16(6H, m), 1.34–1.78(3H, m), 1.54(3H, s, H-14), 0.97–1.17(1H, m), 1.10(3H, d, J=6.10Hz, H-15), 1.09(3H, d, J=7.35Hz, H-16); $\delta_C$ 170.28, 161.74, 137.16, 129.61, 127.38, 125.89, 124.83, 124.01, 123.88, 123.56, 118.72, 104.52, 95.92, 88.85, 80.46, 52.34, 43.84, 37.54, 36.17, 34.51, 30.12, 25.88, 24.58, 24.40, 20.23, 12.61; m/z (EI) 455(M⁺+1, 4), 454(M⁺, 4), 286(24), 284(50), 256 (20), 224(14), 221(8); Anal. Calcd. for C₂₆H₃₀O₇: 68.71; H, 6.65; found: C, 68.64, H, 6.78 |
| 70 | —O—CO—R⁵ | 1-hydroxynaphth-2-yl 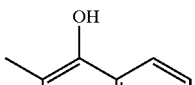 (β-isomer) | White solid. $\delta_H$ 11.95(1H, s, OH), 8.70(1H, d, J=8.69Hz, Ar—H), 7.99 (1H, d, J=9.02Hz, Ar—H), 7.86(1H, dd, J=7.93, 1.11Hz, Ar—H), 7.35–7.59(2H, m, Ar—H), 7.27(1H, d, J=8.95Hz, Ar—H), 6.87(1H, d, J=3.65 Hz, H-10), 5.70(1H, s, H-12), 3.08–3.18(1H, m), 2.44–2.53(1H, m), 2.13–2.19(1H, m), 0.97–2.05(9H, m), 1.56(3H, s, H-14), 1.15(3H, d, J=7.41Hz, H-15), 1.04(3H, d, J=5.74Hz, H-16); $\delta_C$ 172.00, 164.12, 136.64, 131.41, 129.01, 128.58, 127.62, 125.31, 123.72, 119.48, 104.61, 96.76, 89.34, 80.47, 52.30, 43.60, 37.47, 36.19, 34.30, 30.21, 25.90, 24.59, 24.18, 20.21, 12.84; m/z (CI, CH₄) 455(M⁺+1, 4), 454(4), 437 (6), 409(34), 267(80), 249(70), 221(100), 189(54), 163(50); Anal. Calcd. for C₂₆H₃₀O₇: C, 68.71; H, 6.65; found: C, 68.93, H, 6.81 |
| 71 | —O—CO—R⁵ | iooquinolin-4-yl 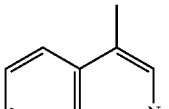 (β-isomer) | |
| 72 | —O—CO—R⁵ | quinolin-2-yl (β-isomer) | White solid. M.p. 75.7–76.4° C. $[\alpha]_D^{20}$ +138° (c 0.013 CHCl₃); $\nu_{max}$ (film) 2940, 1728, 1462, 1378, 1292, 1210, 1140, 1110, 1092, 1074, 1034, 986, 902, 874, 854, 778: $\delta_H$: 7.28–8.33(6H, m, Ar—H), 6.62(1H, d, J=3.16Hz, H-10), 5.72(1H, s, H-12), 2.93–3.02(1H, m), 2.28–2.48(2H, m), 1.82–2.11(5H, m), 0.84–1.72 (4H, m), 1.46(3H, s, H-14), 1.00–1.05(6H, m, H-15, H-16); $\delta_C$: 164.40, 147.86, 147.74, 137.02, 130.93, 130.12, 129.27, 128.58, 127.51, 120.76, 104.41, 96.31, 89.04, 80.74, 52.52, 44.10, 37.56, 36.26, 34.80, 30.34, 24.66, 24.07, 20.37, 12.68; m/z (CI, NH₃) 440(M⁺+1, 100), 284(42), 256(60), 221(10), 174(16); Anal. Calcd. for C₂₅H₂₉NO₆: C, 68.32; H, 6.65; N, 3.19; found: C, 68.30, H, 6.96, N, 3.59. |

| Ex. No. | Y | R⁶ | Physical data |
|---|---|---|---|
| 73 | —OR⁶ | 4-OCH₃ phenyl (β-isomer) | White solid. $\delta_H$: 6.80–7.09(4H, m, Ar—H), 5.55(1H, s, H-12), 5.39(1H, d, J=3.37Hz, H-10), 3.78(3H, s, OMe), 2.74–2.84(1H, m), 2.35–2.45(1H, m), 1.87–2.09(4H, m), 1.28–1.73(5H, m), 0.97–1.05(1H, m), 1.45(3H, s, H-14), 1.04(3H, d, J=7.31Hz, H-15), 0.98(3H, d, J=6.07Hz, H-16); $\delta_C$: 154.73, 151.68, 118.08, 114.56, 104.13, 101.58, 88.16, 81.03, 55.65, 52.54, 44.44, 37.39, 36.37, 34.63, 31.03, 26.07, 24.63, 24.43, 20.31, 13.00. |
| 74 | —OR⁶ | 1-naphthyl (β-isomer) | White solid. $\delta_H$ 8.11–8.15(1H, m, Ar—H), 7.79–7.84(1H, m, Ar—H), 7.37–7.51(5H, m, Ar—H), 5.72(1H, d, J=3.42Hz, H-10), 5.55(1H, s, H-12), 2.89–2.99(1H, m, H-9), |

TABLE I-continued (X = H; Z = O)

| | | | |
|---|---|---|---|
| | | | 2.35–2.45(4H, m), 1.02–2.28(7H, m), 1.42(3H, s, H-14), 1.13(3H, d, J=7.39Hz, H-15), 0.98(3H, d, J= 5.98Hz, H-16); m/z (EI) 410(M$^+$). |
| 75 | —OR$^6$ | 2-naphthyl (β-isomer) | White solid. $\delta_H$ 7.21–7.76(7H, m, Ar—H), 5.66(1H, d, J=3.30Hz, H-10), 5.54(1H, s, H-12), 2.81–2.92(1H, m, H-9), 2.35–2.46(2H, m), 1.86–2.13(7H, m), 0.96–1.68(2H, m), 1.46(3H, s, H-14), 0.96–1.07(2x3H, m, H-15 & H-16); m/z (EI) 410(M$^+$). |
| 76 | —OR$^6$ | benzyl (β-isomer) | White solid. $\delta_H$ 7.28–7.39(5H, m, Ar—H), 5.49(1H, s, H-12), 4.95(1H, d, J=3.55Hz, H-10), 4.94(1H, d, J=12.4Hz, H1'), 4.55(1H, d, J=12.4Hz, H-1'), 2.65–2.75 (1H, m, H-9), 2.41(1H, ddd, J=17.6, 9.49, 3.94Hz), 2.07(1H, ddd, J=14.5, 4.68, 2.92Hz), 0.87–1.97(9H, m), 1.48(3H, s, H-14), 0.97(3H, d, J=7.39Hz, H-15), 0.96(3H, d, J=5.86Hz, H-16); m/z (CI, NH$_3$): 392 (M+NH$_4^+$, 26%), 329(64), 284(100), 267(72), 221(16). Anal. Calcd. for C$_{22}$H$_{30}$O$_5$: C, 70.56; H, 8.07; found: C, 70.89; H, 8.25. |
| 77 | —OR$^6$ | 2-F benzyl (β-isomer) | Colourless oil which solidified on standing. M.p. 81.4–81.9° C. [α]$_D^{20}$: +121° (c 0.37/CHCl$_3$); ν$_{max}$ (film) 2950, 2874, 1586, 1492, 1456, 1376, 1228, 1194, 1158, 1140, 1124, 1098, 1012, 978, 958, 938, 876, 756; $\delta_H$ 7.02–7.42 (4H, m, Ar—H), 5.50(1H, s, H-12), 5.01(1H, d, J=12.4 Hz, H-1'), 4.96(1H, d, J=3.41Hz, H-10), 4.54(1H, d, J=12.4Hz, H-1'), 2.68–2.71(1H, m, H-9), 2.40(1H, ddd, J= 17.5, 13.4, 3.97Hz), 2.06(1H, ddd, J=14.6, 4.83, 3.03Hz), 1.77–1.94(3H, m), 1.21–1.67(6H, m), 1.48(3H, s, H-14), 0.96(3H, d, J=6.34Hz, H-16), 0.94(3H, d, J= 7.55Hz, H-15); $\delta_C$: 129.46(d, J=4.5Hz), 129.01(d, J=8.1Hz), 125.36(d, J=14.7Hz), 123.74(d, J=3.4 Hz), 115.03(d, J=21.1Hz), 103.97, 101.59(d, J=1.8 Hz), 87.87(d, J=2.3Hz), 80.97, 64.03(d, J=3.8Hz), 52.44, 44.27, 37.24, 36.28, 34.48, 30.77, 26.04, 24.53, 24.30, 20.20, 12.82; m/z (CI, NH$_3$) 410(M+NH$_4^+$, 16%), 393 (M$^+$+1, 2), 347(28), 284(100), 267(64), 126(4). Anal. Calc. for C$_{22}$H$_{29}$O$_5$F: C, 67.33, H, 7.45; found: C, 67.23; H 7.48 |
| 78 | —OR$^6$ | 3-F benzyl (β-isomer) | Colourless oil which solidified on standing. M.p. 83.9–84.4° C. [α]$_D^{20}$: +111° (c 0.77/CHCl$_3$); ν$_{max}$ (film) 2922, 2874, 1618, 1592, 1488, 1450, 1376, 1360, 1254, 1194, 1136, 1102, 1032, 1012, 940, 876, 826, 874; $\delta_H$: 6.95–7.35 (4H, m, Ar—H), 5.47(1H, s, H-12), 4.93(1H, d, J=5.12 Hz, H-10), 4.92(1H, d, J=12.6Hz, H-1'), 4.54(1H, d, J= 12.6Hz, H-1'), 2.66–2.76(1H, m, H-9), 2.40(1H, ddd, J= 17.4, 13.4, 3.91Hz), 2.06(1H, ddd, J=14.5, 4.81, 2.99Hz), 1.81–1.95(3H, m), 1.22–1.70(6H, m), 1.48(3H, s, H-14), 0.98(3H, d, J=7.40Hz, H-16), 0.97(3H, d, J= 6.04Hz, H-15); $\delta_C$: 140.85, 129.63(d, J=8.3Hz), 122.37(d, J=2.7Hz), 114.02(d, J=20.9Hz), 113.60, 104.03, 101.36, 87.88(d, J=2.4Hz), 80.94, 68.85, 52.41, 44.20, 37.27, 36.26, 34.44, 30.75, 26.03, 24.52, 24.36, 20.18, 12.93; m/z (CI, NH$_3$) 410(M+NH$_4^+$, 16%), 393 (M$^+$+1, 2), 347(32), 284(100), 267, 66), 126(4). Anal. Calcd. for C$_{22}$H$_{29}$O$_5$F: C, 67.33; H, 7.45; found: C, 67.07, H, 7.48 |
| 79 | —OR$^6$ | 4-F benzyl (β-isomer) | Colourless oil which solidified on standing. M.p. 71.2–71.8° C. [α]$_D^{20}$: +126° (c 0.34/CHCl$_3$); ν$_{max}$ (film): 2920, 1604, 1510, 1450, 1376, 1224, 1156, 1100, 1028, 1012, 956, 938, 876, 826; $\delta_H$: 7.28–7.34(2H, m, H-4' & H-6'), 7.00–7.08(2H, m, H-3' & H-7'), 5.47(1H, s, H-12), 4.91 (1H, d, J=3.50Hz, H-10), 4.87(1H, d, J=12.2Hz, H-1'), 4.51(1H, d, J=12.2Hz, H-1'), 2.64–2.74(1H, m, H-9), 2.41(1H, ddd, J=17.4, 13.4, 3.91Hz), 2.07(1H, ddd, J=14.6, 4.77, 2.98Hz), 1.76–1.95(3H, m), 1.26–1.69(6H, m), 1.48(3H, s, H-14), 0.97(3H, d, J= 6.01Hz, H-16), 0.95(3H, d, J=7.36Hz, H-15); $\delta_C$: 133.93(d, J=3.2Hz), 128.83(d, J=8.2Hz), 114.99(d, J=21.5Hz), 104.01, 101.12, 87.88(d, J=2.4Hz), 80.97, 68.91, 52.42, 44.23, 37.28, 36.28, 34.45, 30.72, 26.05, 24.53, 24.35, 20.18, 12.91; m/z (CI, NH$_3$): 410 (M+NH$_4^+$, 12%), 347(32), 284(100), 267(70), 126(4). Anal. Calcd. for C$_{22}$H$_{29}$O$_5$F: C, 67.33; H, 7.45; found: C, 67.17; H, 7.43 |
| 80 | —OR$^6$ | —CH$_2$-(1-naphthyl) (α- and β-isomers) | Colourless oils. α-isomer: $\delta_H$ 7.40–8.20(7H, m, Ar—H), 5.46(1H, d, J=12.4Hz, H-1'), 5.38(1H, s, H-12), 5.04 (1H, d, J=12.4Hz, H-1'), 4.57(1H, d, J=9.20Hz, H-10), 0.85–2.55(11H, m), 1.50(3H, s, H-14), 0.94(3H, |

TABLE I-continued

| | | (X = H; Z = O) | |
|---|---|---|---|
| | | | d, J=6.00Hz, H-16), 0.86(3H, d, J=7.40Hz, H-15); m/z (CI, NH₃) Anal. Calc. for C₂₆H₃₂O₅: 73.56; H, 7.60; Found, C, 73.77; H, 7.60.: β-isomer: δ_H: 7.40–8.10(7H, m, Ar—H), 5.53(1H, s, H-12), 5.38(1H, d, J=12.5Hz, H-1'), 5.03(1H, d, J=10.8Hz, H-10), 4.93(1H, d, J= 12.5Hz, H-1'), 2.69(1H, m, H-9), 1.20–2.40(10H, m), 1.49(3H, s, H-14), 0.94(3H, d, J=6.00Hz, H-16), 0.86 (3H, d, J=7.40Hz, H-15); m/z (CI, NH₃). Anal. Calc. for C₂₆H₃₂O₅: 73.56; H, 7.60; Found, C, 73.66; H, 7.59. |
| 81 | —OR⁶ | —CH₂-(10-anthryl) (β-isomer) | Yellow solid. M.p. 97.2–98.7° C.; [α]_D²⁰: +112.5° (c 0.63/CHCl₃); ν_max (film) 2920, 1448, 1374, 1194, 1098, 1010, 938, 874, 846, 826, 754; δ_H 8.41–8.48(3H, m, Ar—H), 8.02–8.05(2H, m, Ar—H), 7.50–7.58(3H, m, Ar—H), 5.86 (1H, d, J=11.6Hz, H-1'), 5.69(1H, s, H-12), 5.51(1H, d, J=11.6Hz, H-1'), 14(1H, d, J=3.42Hz, H-10), 1.23–2.70(12H, m), 1.57(3H, s, H-14), 0.92(3H, d, J= 5.83Hz, H-16), 0.77(3H, d, J=7.35Hz, H-15); m/z (CI, NH₃) 492(M+NH₄⁺, 18%), 474(8), 446(6), 284(32), 267 (18), 207(10), 191(100). Anal. Calc. for C₃₀H₃₄O₅: C, 75.92; H, 7.22; found: C, 75.78; H, 6.84. |
| 82 | —OR⁶ | —CH₂-(1-phenanthryl) (β-isomer) | White solid. M.p. 93.8–94.3° C. [α]_D²⁰: +99.2° (c 0.26/CHCl₃). ν_max (film): 2920, 1450, 1376, 1248, 1194, 1098, 1042, 1006, 956, 938, 874, 826, 748, 724; δ_H: 7.59–8.77(9H, m, Ar—H), 5.60(1H, s, H-12), 5.43(1H, d, J=12.3Hz, H-1'), 5.10(1H, d, J=3.36Hz, H-10), 5.00 (1H, d, J=12.3Hz, H1'), 2.69–2.75(1H, m, H-9), 2.43 (1H, ddd, J=18.3, 13.5, 3.94Hz), 1.26–2.12(9H, m), 1.52(3H, s, H-14), 0.96(3H, d, J=6.03Hz, H-16), 0.89 (3H, d, J=7.38Hz, H-15); m/z (CI, NH₃): 492(M+NH₄⁺, 32%), 446(22), 429(100), 284(100), 267(58), 208(60), 191(34). Anal. Calcd. for C₃₀H₃₄O₅; C, 75.92; H, 7.22; found: C, 75.94; H, 7.54 |
| 83 | —OR⁶ | —CH₂-(1-pyryl) (β-isomer) | Yellow solid. [α]_D²² +84.3° (c 0.019/CHCl₃); ν_max (film) 2920, 1456, 1374, 1192, 1138, 1098, 1010, 938, 874, 846, 826, 754, 710; δ_H: 8.01–8.35(9H, m, Ar—H), 5.67(1H, d, J= 12.2Hz, H-1'), 5.63(1H, s, H-12), 5.22(1H, d, J= 12.2Hz, H-1'), 5.13(1H, d, J=3.38Hz, H-10), 2.69–2.79 (1H, m, H-9), 2.43(1H, ddd, J=17.6, 13.6, 4.00Hz), 2.11(1H, ddd, J=14.5, 4.70, 2.96Hz), 1.70–1.98(3H, m), 0.86–1.61(6H, m), 1.54(3H, s, H-14), 0.95(3H, d, J= 6.00Hz, H-16), 0.91(3H, d, J=7.37Hz, H-15); δ_C 131.40, 131.23, 131.08, 130.77, 129.03, 127.47, 127.42, 127.29, 126.57, 125.89, 125.16, 124.80, 124.70, 124.48, 123.48, 104.17, 101.48, 88.20, 81.19, 68.48, 52.55, 44.40, 37.37, 36.43, 34.54, 30.99, 26.24, 24.67, 24.47, 20.30, 13.07; m/z (CI, NH₃): 516(M+NH₄⁺, 6%), 470(8), 329(8), 284(28), 215(100). Anal. Calc. for C₃₂H₃₄O₅: C, 77.08; H, 6.87; Found: C, 76.81; H, 7.13. |
| 84 | —OR⁶ | 4-quinolinyl (β-isomer) | White solid. M.p. 131–134° C.; [α]_D²¹·⁵ +45.93° (c. 0.028 in CHCl₃); ν_max (Neat): 3252, 2990, 1592, 1532, 1506, 1308, 1244, 1098, 1068, 928, 874, 768 cm⁻¹; δ_H: 7.28–8.22(6H, m, Ar—H), 5.82(1H, d J=3.36Hz, H-10), 5.49(1H, s H-12), 2.95–3.05(1H, m, H-9), 2.42(1H, ddd, J=16.8, 13.2, 4.07Hz), 1.10–2.18(10H, m), 1.49(3H, s, H-14), 1.15 (3H, d, J=7.38Hz, H-15), 0.99(3H, d, J=5.84Hz, H-16); m/z (CI, CH₄): 412(M⁺+1, 48%), 284(36), 267(24), 221(12), 191(100), 146(84). |
| 85 | —OR⁶ | cholest-5-en-3-yl (β-isomer) | White solid. [α]_D²⁰: +82.5° (c 0.16/CHCl₃); ν_max (film): 2936, 1462, 1376, 1100, 1012, 878, 826, 754; δ_H: 5.48 (1H, s, H-12), 5.36(1H, d, J=4.91Hz, olefinic-H), 4.95 (1H, d, J=3.35Hz, H-10), 3.57–3.62(1H, m, —CHOCH-10-), 2.60–2.65(1H, m, H-9), 0.87–2.44(39H, m), 1.46(3H, s, H-14), 0.98(3H, d, J=6.23Hz, H-16), 0.94 (3H, d, J=6.51Hz, CH₃CH), 0.90(3H, d, J=7.28Hz, H-15), 0.89(3H, d, J=6.56Hz, CH₃CHCH₃), 0.88(3H, d, J= 6.55Hz, CH₃CHCH₃). |

TABLE II (X = H; Y = = O; A = = NR$^7$)

| Ex. No. | R$^7$ | Physical data |
|---|---|---|
| 86 | 4-F benzyl | colourless needle-shaped crystal; M.p. : 163.5–164.5; [α]$_n^{20.5}$ + 25.83° (c. 0.0096 in CHCl$_3$); ν$_{max}$ (Nujol): 3068, 2922, 1650 (ν$_{c=o}$, amide), 1604, 1508, 1454, 1378, 1350, 1284, 1238, 1216, 1152, 1098, 1070, 1030, 992, 966, 946, 920, 886, 854, 842, 820, 796, 766 cm$^{-1}$; $^1$H NMR (300 MHz, CDCl$_3$): δ$_H$ (ppm) = 0.67–0.81 (dq, J=13.2 Hz, J=3.35 Hz, 1H), 0.84–1.09 (m, 1H), 0.94(d, J$_{6-Me,6}$= 6.1 Hz, 3H, 6-CH$_3$), 1.14(s, 3H, 3-CH$_3$), 1.18(d, J$_{9-Me,9}$=7.32 Hz, 3H, 9-CH$_3$), 1.19–1.47(m, 3H), 1.60–1.71(m, 2H), 1.77(qd, J=13.2 Hz, J=3.6 Hz, 1H), 1.92–2.00 (m, 2H), 2.34–2.44(m, 1H), 3.37(dq, J$_{9,9-Me}$=7.3 Hz, J$_{9,8a}$=4.9 Hz, 1H, H-9), 4.58(d, J=14.5 Hz, 1H, H-1'β), 4.85(d, J=14.5 Hz, 1H, H-1'α), 6.94-7.08(m, 2H,H-3', H-7'), 7.26–7.38(m, 2H, H-4', H-6'); MS (FAB): m/z (%) = 390 [M$^+$ + 1] (12), 307(26), 289(12), 273(4), 165(8), 155 (28), 154(100), 136(68), 69(26), 55(30); Anal. Calc. for C$_{22}$H$_{28}$FNO$_4$: C, 67.85; H, 7.25; N, 3.59; Found: C, 67.68; H, 7.20; N, 3.53. |
| 87 | 3-F benzyl | colourless needle-shaped crystal; M.p. 106–107.1° C.; [α]$_D^{20.5}$ + 28.85° (c. 0.0104 in CHCl$_2$); ν$_{max}$ (Nujol): 2922, 1650(ν$_{c=o}$, amide), 1613, 1581, 1488, 1419, 1388, 1275, 1250, 1212, 1013, 998, 944, 919, 888, 850, 801 cm$^{-1}$; $^1$H NMR (300 MHz, CDCl$_3$): δ$_H$ (ppm) = 0.74–0.88(dq, J=13.1 Hz, J=3.2 Hz, 1H), 0.92–1.02 (m, 1H), 0.95 (d, J$_{6-Me,6}$=5.9 Hz, 3H, 6-CH$_3$), 1.12(s, 3H, 3-CH$_3$), 1.19 (d, J$_{9-Me,9}$=7.6 Hz, 3H, 9-CH$_3$), 1.25–1.48(m, 3H), 1.59–1.75(m, 2H), 1.80 (qd, J=13.2 Hz, J=3.5 Hz, 1H), 1.93–1.99(m, 2H), 2.34–2.44 (m, 1H), 3.39 (dq, J$_{9,9-Me}$7.6 Hz, J$_{9,8a}$=4.9 Hz, 1H, H-9), 4.68(d, J=14.8 Hz, 1H, H-1'β), 4.78(d, J=14.8 Hz, 1H, H-1'α), 5.30(s, 1H, H-12), 6.88–7.29 (m, 4H, phenyl-H); MS(FAB): m/z (%) = 390 [M + 1] (4), 329(2), 307(24), 289(16), 273(4), 165(6), 154(100), 136(64), 107(20), 91(16); Anal. Calc. for C$_{22}$H$_{28}$FNO$_4$: C, 67.85; H, 7.25; N, 3.59; Found: C, 67.96; H, 7.34; N, 3.59. |
| 88 | benzyl | crystalline solid; M.p. 113–115° C.; R$_f$ = 0.42 (EtOAc:hexane, 1:4); [α]$^{25}_D$ = 27.2° (C 0.58, CH$_2$Cl$_2$); IR 2928, 2873, 1653 cm$^{-1}$; CIMS (NH$_3$) 389(M + NH$_4^+$, 65), 372(M + 1,100); $^1$H NMR δ 0.70–0.87(2H, m), 0.94(3H, d, J=6.1 Hz), 0.94–1.08 (1H, m), 1.15(3H, s), 1.20(3H, d, J=7.3 Hz), 1.15–1.42(3H, m), 1.62–1.81(3H, m), 1.92–2.00(2H, m), 2.36(1H, m), 3.39(1H, m), 4.62 (1H, d, J=14.5 Hz), 4.95(1H, d, J=14.6 Hz), 7.22–7.32(5H, m). |
| 89 | —CH$_3$ | crystalline solid; R$_f$ = 0.67(EtOAc:hexane, 3:7); [α]$^{25}_D$ = 15.9° (c 0.375, CH$_2$Cl$_2$); IR 2926, 2873, 1649 cm$^{-1}$; CIMS (NH$_3$) 313(M + NH$_4^+$, 24), 296(M + 1, 100); $^1$H NMR δ 0.9–1.06 (2H, m), 0.96(3H, d, J=6.8 Hz), 1.14(3H, d, J=7.4 Hz), 1.36 (3H, s), 1.35–1.55(2H, m), 1.63–1.81(4H, m), 1.97–2.04(2H, m), 2.42(1H, m), 2.95(3H, s), 3.27(1H, pent, J=5.6 Hz), 5.15 (1H, s). |
| 90 | —CH$_2$CH$_2$(CH$_3$)$_2$ | crystalline solid. M.p. 100–101° C.; R$_f$ = 0.72 (EtOAc:hexane, 3:7); [α]$^{25}_D$ = 9.8° (c 0.275, CH$_2$Cl$_2$); IR 2926, 2873, 1658 cm$^{-1}$; CIMS (NH$_3$) 355(M + NH$_4^+$, 24), 338(M + 1, 100); $^1$H NMR δ 0.87–1.12(3H, m), 0.87(3H, d, J=6.6 Hz), 0.93 (3H, d, J=6.6 Hz), 1.00(3H, d, J=5.9 Hz), 1.14(3H, d, J=7.3 Hz), 1.36(3H, s), 1.23–1.52(2H, m), 1.53–1.88(3H, m), 1.92–2.13(3H, m), 2.37–2.46(1H, m), 3.27–3.36(2H, m), 3.42–3.49(1H, m), 5.25(1H, s). |
| 91 | —CH$_2$CH=CH$_2$ | solid. M.p. 101–103° C.; R$_f$ = 0.55 (EtOAc:hexane, 1:4); [α]$^{25}_D$ = 14.0° (c 0.417, CH$_2$Cl$_2$); IR 2926, 2873, 1658 cm$^{-1}$; CIMS (NH$_3$) 339(M + NH$_4^+$, 42), 322(M + 1, 100); $^1$H NMR δ 0.91(1H, dd, J=3.0, 2.8 HZ), 0.99(3H, d, J=5.8 Hz), 0.95–1.05(1H, m), 1.03–1.52(3H, m), 1.14(3H, d, J=7.5 Hz), 1.36(3H, s), 1.63–1.82(3H, m), 1.95–2.03(2H, m), 2.36–2.47(1H, m), 3.29–3.33(1H, m) 3.97(1H, dd, J=14.9, 3.1 Hz), 4.29(1H, dd, J=14.8, 4.5 Hz), 5.14–5.25(2H, m), 5.22(1H, s), 5.80(1H, m). |
| 92 | —CH$_2$CHO | white solid. M.p. 80–81° C.; R$_f$ = 0.34 (EtOAc:hexane, 3:7); [α]$^{25}_D$ = 10.7° (c 0.566, CH$_2$Cl$_2$); IR 2935, 2875, 1735, 1660 cm$^1$; CIMS (NH$_3$) 341(M + NH$_4^+$, 11), 324(100); $^1$H NMR δ 0.94(1H, d, J=3.9 Hz), 1.01(3H, d, J=6.8 Hz), 1.17 (3H, d, J=7.1 Hz), 1.34(3H, s), 1.00–1.50(3H, m), 1.70–1.86(4H, m), 2.01(2H, d, J=13.6 Hz), 2.36–2.47(1H, m), 3.36–3.40(1H, m), 4.39(2H, q, J =18.0 Hz), 5.29(1H, s), 9.58(1H, s). |
| 93 | pyrid-2-ylmethyl | solid. M.p. 111–113° C.; R$_f$ = 0.19 (EtOAc:hexane, 2:3); [α]$^{25}_D$ = 6.9° (c 0.117, CH$_2$Cl$_2$); IR 2932, 2873, 1654, 1591 cm$^{-1}$; CIMS (NH$_3$) 373(M + H$^+$, 100), $^1$H NMR δ 0.87–1.50(4H, m), 0.99(3H, d, J=5.8 HZ), 1.05(3H, s), 1.17(3H, d, J= 7.1 Hz), 0.94–1.08(1H, m) 1.68–1.81(3H m), 1.92–2.00(2H, m), 2.35–2.41 (1H, m), 3.39(1H, pent, J=5.4 Hz), 4.68(1H, d, J=15.6 Hz), 4.98(1H, d, J=15.7 Hz), 5.52(1H, s), 7.12(1H, t, J=6.1 Hz), 7.34(1H, d, J= 7.5 Hz), 7.62(1H, t, J=7.3 Hz), 8.49(1H, d, J=4.7 Hz). |
| 94 | thenyl | solid. M.p. 129–131° C.; R$_f$ = 0.69 (EtOAc:hexane, 3.7); [α]$^{25}_D$ = 12.3° (c 0.30, CH$_2$Cl$_2$); IR 2929, 2871, 1655 cm$^{-1}$; CIMS (NH$_3$) 395(M + NH$_4^+$, 42), 378(M + 1, 100); $^1$H NMR δ 0.69–0.77(1H, m), 0.94(3H, d, J=6.0 Hz), 1.17(3H, d, J= 7.4 Hz), 1.32(3H, s) 1.60–1.74(6H m), 1.94–2.04(3H, m), 2.37–2.42(1H, m) 3.33(1H, m), 4.60(1H, d, J=14.8 Hz), 5.18(1H, s), 5.25(1H, d, J=15.0 Hz), 6.93(1H, t, J=4.1 Hz), 7.01(1H, m), 7.21(1H, d, J=5.0 Hz). |
| 9S | furfuryl | solid. M.p. 148–151° C.; R$_f$ = 0.47 (EtOAc:hexane, 1:4); [α]$^{25}_D$ = 8.4° (c 0.25, CH$_2$Cl$_2$); IR 2944, 2921, 2881, 2851, 1654 cm$^{-1}$; CIMS (NH$_3$) 379(M + NH$_4^+$, 30), 362(M + 1, 100); $^1$H NMR δ 0.73–1.00 (3H, m), 0.97(3H, d, J=5.7 Hz), 1.16 (3H, d, J=7.4 Hz), 1.33(3H, s) 1.53–1.76(5H, m), 1.94–2.04(2H, m), 2.36–2.41(1H, m), 3.33(1H, pent, J=4.8 Hz), 4.45(1H, d, J=15.2 Hz), 5.05(1H, d, J=15.2 Hz), 5.20(1H, s), 6.26(1H, d, J=3.1 Hz), 6.31(1H, t, J=2.2 Hz), 7.33 (1H, d, J=4.7 Hz). |

TABLE II-continued

(X = H; Y = = O; A = = NR⁷)

| Ex. No. | R⁷ | Physical data |
|---|---|---|
| 96 | —CH$_2$CH$_2$OH | White plates. M.p. 95.6–96.0° C.; $^1$H NMR (300 MHz, CDCl$_3$): δ (ppm) = 0.86–1.08 (m, 1H), 0.93(d, J$_{6\text{-Me6}}$=5.8 Hz, 3H, 6-CH$_3$), 1.14(d, J$_{9\text{-Me,9}}$=7.3 Hz, 3H, 9-CH$_3$), 1.19–1.34(m, 2H), 1.47(s, 3H, 3-CH$_3$), 1.59–1.94(m, 7H), 1.99(dt, J=12.9 Hz J=4.3 Hz, 1H), 3.08(dq, J$_{9,9\text{-Me}}$=7.2 Hz, J$_{9,8a}$4.4 Hz, 1H, H-9), 3.24 (ddd, J=14.5 Hz, J=7.5 Hz, J=3.2 Hz, 1H, CH$_2$—N) 3.75–3.82(m, 2H), 3.45(bs, 1H, OH), 3.99(ddd, J=14.5 Hz, J=4.5 Hz, J=2.6 Hz, 1H HO—CH$_2$) 5.04(s, 1H, H-12); MS (EI, 70 eV): m/z (%) = 310[(M$^+$ + 1] (2), 309(16), 278(12), 266(60), 249(100), 234(36), 218(24), 206(16), 192,(26), 162(10), 148(8), 55 (8), 43(18). |

TABLE III

(X = -NR$^1$R$^2$, Y = =O; Z = O)

| Ex. No | -NR$^1$R$^2$ | Physical data |
|---|---|---|
| 97 | indolin-1-yl | White solid; M.p. 64.9–65.1° C.; [a]$_D^{20}$: +74.4° (c 0.018 CHCl$_3$); ν$_{max}$ (film): 2926, 1732, 1606, 1488, 1456, 1376, 1276, 1228, 1154, 1126, 1106, 1030, 998, 880, 830, 748; δ$_H$ 7.08–7.12(2H, m, Ar—H), 6.59–6.72(2H, m, Ar—H), 6.00(1H, s, H-12), 3.81(1H, dd, J=13.5, 11.3 Hz, ArCH$_2$), 3.57(1H, ddd, J=9.06, 8.89, 5.24 Hz, NCH$_2$), 3.49(1H, dd, J=13.5, 4.79 Hz, ArCH$_2$), 3.29(1H, ddd, J=9.33, 9.06, 8.89 Hz, NCH$_2$), 2.93–3.12(2H, m, H-16), 2.42–2.62(2H, m), 1.94–2.17(3H, m), 1.37–1.75(6H, m), 1.51 (3H, s, H-14), 1.09–1.22(1H, m), 1.00(3H, d, J=5.89 Hz) H-15); δ$_c$ 170.21, 152.44, 129.36, 127.37, 124.32, 117.61, 106.73, 105.32, 93.80, 80.39, 54.14, 53.73, 50.22, 44.29, 39.59, 37.45, 35.75, 33.78, 31.28, 28.50, 25.35, 24.65, 19.72; m/z (CI, CH$_4$): 400(M$^+$ + 1, 100), 399(M$^+$, 76), 371(14), 132(90). Anal. Calc. for C$_{23}$H$_{29}$NO$_5$: C, 69.15; H, 7.32; N, 3.50; Found C, 69.28; H, 7.33; N, 3.31. |

TABLE IV

(X = —CHR$^8$R$^9$; Z = O)

| Example No. | Y | R$^8$ | R$^9$ | Physical data |
|---|---|---|---|---|
| 98 | =O | —H | —NO$_2$ | |
| 99 | =O | —CH$_3$ | —CO—OCH$_3$ | Yield: 283 mg (28.3%) |
| 100 | =O | —H | —CO-phenyl | Colourless oil. [α]$_D^{20}$ + 67.9° (0.038 CHCl$_3$); ν$_{max}$ (film) 2928, 1734, 1732, 1682, 1448, 1376, 1212, 1106, 994, 832, 760, 692; δ$_H$ 7.99–8.03(2H, m, Ar—H), 7.44–7.59(3H, m, Ar—H), 5.93(1H, s, H-12), 3.36–3.46(1H, m, H-17), 3.12–3.22(1H, m, H-17), 1.07–2.47(14H, m), 1.48(3H, s, H-14), 1.01(3H, d, J=5.85 Hz, H-15); δ$_c$ 200.02, 171.52, 136.78, 132.88, 128.42, 127.98, 105.15, 93.82, 80.00, 50.35, 44.91, 43.72, 37.44, 36.16, 35.81, 33.83, 31.25, 28.71, 25.37, 24.55, 19.75; m/z (CI, CH$_4$): 401(M$^+$ + 1, 100%), 355(48), 309(44), 165(14). Anal. Calcd. for C$_{23}$H$_{28}$O$_6$: C, 68.98; H, 7.05; found: C, 69.07, H, 6.99. |
| 101 | =O | cyclohexyl | | White solid. M.p. 110.0–111.2° C.; [α]$_D^{20}$: +92.7° (c 1.15 CHCl$_3$); ν$_{max}$ (film) 2922, 2850, 1736, 1448, 1376, 1220, 1152, 1104, 1032, 1006, 884, 834; δ$_H$ 5.92 (1H, s, H-12), 2.36–2.46 (1H, m, H-16), 2.29(1H, dd, J=9.69, 4.76 Hz), 1.93–2.11 (3H, m), 1.10–1.79(20H, m), 1.46(3H, s, H-14), 1.01(3H, d, J=5.88 Hz, H-15); δ$_c$ 172.49, 105.09, 93.45, 80.14, 50.34, 42.68, 42.00, 41.76, 37.45, 35.79, 34.65, 33.93, 33.67, 31.96, 31.26, 26.39, 26.12, 25.96, 25.30, 24.64, 19.75; m/z (CI, CH$_4$) 365(M$^+$ + 1, 100%), 347(90), 329(54), 319(62), 305(40), 301(46), 291(58), 191(12), 154(30), 105(58). Anal. Calcd. for C$_{21}$H$_{32}$O$_5$: C, 69.20; H, 8.85; found: C, 69.09, H, 8.95. |
| 102 | =O | adamantyl | | White solids (5.6:1 inseparable diastereomeric mixture) M.p. 188.7–189.5° C.; [α]$_D^{20}$: +68.1° (c 0.69 CHCl$_3$); ν$_{max}$ (film) 2904, 2850, 1732, 1454, 1374, 1214, 1104, 1032, 1006, 880, 832, 756; δ$_H$ 5.91(1H, s, H-12), 5.78(1H, s, H-12), 2.35–2.44(1H, m, H-16), 1.09–2.22(27H, m), 1.46(3H, s, H-14), 1.00(3H, d, J=5.85 Hz, H-15); δ$_c$ 172.51, 105.08, 104.75, 93.44, 91.46, 80.21, 78.75, 50.52, 50.34, 42.59, |

TABLE IV-continued (X = —CHR$^8$R$^9$; Z = O)

| Example No. | Y | R$^8$ | R$^9$ | Physical data |
|---|---|---|---|---|
| | | | | 42.35, 42.27, 41.13, 39.12, 38.94, 38.16, 37.44, 37.37, 36.66, 35.85, 35.79, 33.93, 33.74, 32.78, 31.71, 31.53, 31.43, 31.13, 30.10, 28.37, 28.09, 28.01, 27.87, 27.82, 26.96, 26.60, 25.31, 25.23, 24.63, 24.35, 23.26, 19.91, 19.75, 17.17, 13.44; m/z (CI, CH$_4$) 417(M$^+$+ 1, 100%), 399(86), 371(84), 357(58), 353(50), 343(44), 268(24), 208(12), 154(14), 105(34). Anal. Calcd. for C$_{25}$H$_{36}$O$_5$: C, 72.09; H, 8.71; found: C, 72.08, H, 8.84. |
| 103 | —H | —CO—OC$_2$H$_5$ | —CO—OC$_2$H$_5$ | δ$_H$ : 5.21(1H, g, H-12), 4.11–4.27(2x2H, m, OC$\underline{H}_2$CH$_3$), 3.83–3.94(2H, m, H-10), 3.49(1H, dd, J=8.22, 7.73 Hz, H-17), 2.24–2.40(3H, m, H-9 and 2xH-16), 1.86–2.05(2H, m), 1.04–1.67(9H, m), 1.42(3H, s, H-14), 1.27(2x3H, t, J=7.15 Hz, OCH$_2$C$\underline{H}_3$), 0.96(3H, d, J=5.88 Hz, H-15). |
| 104 | —H | —H | —NO$_2$ | Colourless oil. δ$_H$: 5.18(1H, s, H-12), 4.46–4.60(2H, m, H-10), 3.82–3.94(2H, m, H-17), 2.48–2.57(2H, m, H-16), 2.27–2.37(1H, m, H-9), 1.86–2.07(2H, m), 0.98–1.71(9H, m), 1.42(3H, s, H-14), 0.97(3H, d, J=5.97 Hz, H-15). |

EXAMPLE 105

Screening of compounds for cytotoxicity

Compounds of the invention were screened against Rat 6 subclone of the immortalized F2408 embryo cell line, and Rat 6 (R6T24) cells transfected and transformed by a c-H-ras oncogene. The screening involved placing the R6 and R6T24 cell lines plated at 10$^3$ cells per well into a 12-well microtiter culture plate for 24 hours. The compounds were added at final concentrations from 0.1–100 μM, and cells were trypsized and counted by Coulter Counter at day 3 and day 6 after the addition. Untreated cells were assigned a survival value of 100%. The known compounds artemisinin, dihydroartemisin, artemether and artesunate were also screened together with two analogous compounds of Formula D and Formula E below which lack the peroxide bond as comparative examples.

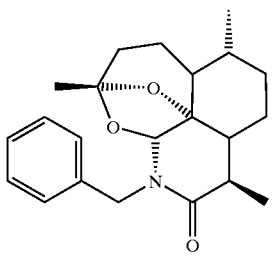
(D)

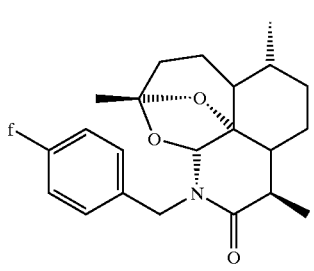
(E)

The results are set out in Table V below:

TABLE V

| | LD$_{50}$ μM Day 3) Cell line | | LD$_{50}$ μM (Day 6) Cell line | |
|---|---|---|---|---|
| Example No. | R6 | R6T24 | R6 | R6T24 |
| 1 | 1.18 | 1.93 | 1.63 | 0.61 |
| 2 | 0.61 | 3.05 | 0.475 | 0.54 |
| 4 | 1.37 | 1.09 | 0.29 | 0.13 |
| 11 | 1.56 | 3.31 | 0.87 | 0.39 |
| 13 | 0.14 | 0.12 | 0.037 | 0.02 |
| * 14 | >50.00 | 0.18 | 1.22 | 0.09 |
| * 15 | 22.70 | >50.00 | >50.00 | 1.69 |
| 17 | 1.57 | 1.81 | 2.58 | 0.54 |
| 19 | 52.00 | 28.12 | 59.00 | 24.95 |
| 27 | 0.57 | 0.67 | 1.10 | 0.26 |
| 30 | 0.31 | 0.24 | 0.26 | 0.26 |
| 31 | 0.34 | 0.23 | 0.27 | 0.14 |
| 40 | 0.47 | 0.58 | 0.41 | 0.21 |
| 65 | 2.73 | 3.21 | 2.52 | 1.60 |
| 66 | 0.34 | 0.32 | 3.60 | 0.32 |
| 87 | >50.00 | 6.14 | 17.5 | 1.07 |
| 88 | 46.67 | 10.45 | 18.49 | 5.24 |
| 97 | 24.77 | 11.38 | 29.24 | 7.45 |
| Artemisinin | >100.00 | 3.09 | 4.08 | 1.75 |
| Dihydro-artemisinin | 1.64 | 2.22 | 0.86 | 0.24 |
| Artemether | >100.00 | >100.00 | 1.0 | 1.8 |
| Artesunate | 2.80 | 1.77 | 2.06 | 1.04 |
| * D | >50.00 | >50.00 | >50.00 | >50.00 |
| * E | >50.00 | >50.00 | >50.00 | >50.00 |

* Signifies maximum tested concentration was 50 μM

TABLE VA

| | LD$_{50}$ μM Day 3) Cell line | | LD$_{50}$ μM (Day 6) Cell line | |
|---|---|---|---|---|
| Example No. | R6 | R6T24 | R6 | R6T24 |
| 1 | 1.28 | 1.93 | 1.62 | 0.61 |
| 2 | 0.61 | 3.05 | 0.475 | 0.54 |
| 4 | 1.37 | 1.09 | 0.29 | 0.13 |
| 11 | 1.56 | 3.31 | 0.87 | 0.39 |
| 13α | 0.14 | 0.12 | 0.037 | 0.02 |
| 14 | >50 | 0.18 | 1.22 | 0.09 |
| 15 | >50 | 22.7 | >50 | 1.69 |
| 22 | 25 | 12 | 29 | 7.5 |
| 27 | 0.57 | 0.67 | 1.10 | 0.26 |

TABLE VA-continued

| | LD$_{50}$ μM Day 3) Cell line | | LD$_{50}$ μM (Day 6) Cell line | |
|---|---|---|---|---|
| Example No. | R6 | R6T24 | R6 | R6T24 |
| 30 | 0.31 | 0.24 | 0.26 | 0.26 |
| 31 | 0.34 | 0.23 | 0.27 | 0.14 |
| 51 | 0.33 | 0.33 | 0.12 | 0.11 |
| 56 | 0.38 | 0.24 | 0.26 | 0.21 |
| 66 | 0.34 | 0.32 | 3.6 | 0.32 |
| 67 | 0.87 | 0.86 | 0.22 | 0.18 |
| 80α | 0.40 | 0.34 | 0.38 | 0.19 |
| 82 | 0.12 | 0.05 | 0.12 | 0.06 |
| 88 | 47.0 | 10.45 | 18.49 | 5.24 |
| 96 | 24.8 | 11.4 | 29.2 | 7.5 |
| Artemisinin | >100.00 | 3.49 | 4.08 | 1.75 |
| Dihydro-artemisinin | 1.64 | 2.22 | 0.86 | 0.24 |
| Artemether | >100 | >100 | 0.6 | 0.71 |
| Artesunate | 2.80 | 1.77 | 2.08 | 1.04 |
| * D | >50 | >50 | >50 | >50 |
| * E | >50 | >50 | >50 | >50 |

* Signifies maximum tested concentration was 50 μM

It is apparent from Tables V and VA that compounds containing a trioxane moiety which includes a peroxide bond were considerably more active than the compounds of Comparative Examples D and E which do not include a peroxide bond. Indeed, it was not possible to establish an LD$_{50}$ value for the compounds of Comparative Examples D and E since this was in excess of the maximum concentration tested for these compounds. Accordingly, these results clearly show that the presence of a peroxide bond is essential for good cytotoxic activity.

It should also be noted that the cytotoxicity of the compounds of the present invention is generally greater than that of the known compounds named in the table. Indeed, this is particularly true in the case of those compounds of the present invention which contain intercalating groups.

Whilst dihydroartemisinin elicits appreciable cytotoxicity, it has been shown through the use of the DNA comet assay technique that dihydroartemisinin does not bind to DNA. In this technique, cells are embedded in agarose gel on a frosted slide after 3 or 6 day treatment, the cells are then lysed and submitted to electrophoresis. The DNA was stained after electrophoresis by ethidium bromide and images of the DNA "comets" were obtained by using an image analysis software package. From these tests, it was apparent that none of the artemisinin derivatives which do not contain an intercalating group damage DNA within the cell. In contrast, the most cytotoxic compounds of those listed in Table V, that is, the compounds of Examples 4, 13 and 22, elicited strong DNA damage according to the assay and contain intercalating groups.

EXAMPLE 106

As another example of evaluation of cytotoxicity, cancer cell lines were also used for a growth inhibition assay. The human colon cancer cell lines SW 480 and HT 29 and the murine melanoma cell line B16F10 were used. These were grown in RPMI 1640 medium supplemented with 10% of FCS. After confluent growth, the cells were trypsinated and resuspended in RPMI plus 10% FCS to a cell concentration of 50000 cells per ml in case of colon cancer cell lines and 20000 in case of B16F10. 100 μl of this cell suspension were transferred in each well of a 96 well microtiter plate and incubated for 1 day at 37° C. in a CO$_2$-incubator. Subsequently, further 100 μl RPMI medium and 1 μl of a DMSO solution, containing the artemisinin derivatives were added. The growth inhibition was estimated after 6 days incubation at 36° C. using the MTT assay.

25 μl MTT solution (3-(4,5-dimethylthiazol-2-yl)-2,5-diphenyltetrazolium-bromid) of a starting concentration of 5 mg/ml H$_2$O were added and incubated at 37° C. for 5 h. Subsequently, 100 μl iso-propanol per well were added. After 15 min incubation 100 μl H$_2$O were added. After 30 min shaking, the extinction was measured at 595 nm using a ELISA-Multiplate Reader.

The data gathered confirms that compounds display relatively high level of activity. The data for the examples are included in Table VI.

TABLE VI

Results of in vitro screens against tumour cell lines.

| | LD$_{50}$ nM | | |
|---|---|---|---|
| Example No | SW 480 | HT 29 | B16F18 |
| CAMPTOTHECIN | 9 | 4 | 30 |
| 2 | 300 | 800 | 500 |
| 11 | 500 | 1500 | 500 |
| 12 | 150 | 2000 | 300 |
| 13α | 200 | 500 | 300 |
| 13β | 300 | 600 | 400 |
| 15 | 200 | 1500 | 300 |
| 28 | 150 | 300 | 300 |
| 29 | >10000 | >10000 | >10000 |
| 30 | 100 | 600 | 400 |
| 33 | 60 | 500 | 200 |
| 34 | 100 | 500 | 150 |
| 36 | 60 | 400 | 50 |
| 40 | 600 | >10000 | >10000 |
| 52 | 250 | 500 | 500 |
| 56 | 200 | 300 | 300 |
| 59 | 1500 | 1500 | 1500 |
| 60 | 150 | 300 | 250 |
| 61 | 150 | 300 | 250 |
| 67 | 2000 | 10000 | >2500 |
| 68 | >1500 | >4000 | >2500 |
| 69 | 800 | 8000 | 6000 |
| 78 | 250 | 1500 | 200 |
| 79 | 200 | 1500 | 200 |

What is claimed is:

1. A method for treating cancer comprising administering to a mammal in need of such treatment a compound of the general formula I

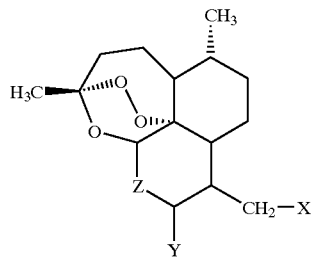

(I)

or a salt thereof, in which X represents a hydrogen atom or a group —NR$^1$R$^2$, —CHR$^8$R$^9$, or Ar; Y represents a hydrogen or halogen atom, an oxo or hydroxyl group, an optionally substituted cycloalkyl, aryl, C-linked heteroaryl or heterocyclylalkyl group or a group —NR$^3$R$^4$, —O—CO—R$^5$ or —OR$^6$; and Z represents an oxygen atom; where R$^1$ and R$^2$ independently represent an optionally substituted alkyl, cycloalkyl, aryl or aralkyl group; or R$^1$ and R$^2$ together with the interjacent nitrogen atom represent an optionally substituted heterocyclic group or an amino group derived from an optionally substituted amino acid ester;

R$^3$ represents a hydrogen atom or an optionally substituted alkyl, alkenyl or alkynyl group;

R$^4$ represents an optionally substituted alkyl, alkenyl, alkynyl, cycloalkyl, aryl or aralkyl group; or R$^3$ and R$^4$ together with the interjacent nitrogen atom represent an optionally substituted heterocyclic group or an amino group derived from an optionally substituted amino acid ester;

R$^5$ represents an optionally substituted alkyl, alkenyl, alkynyl, cycloalkyl, aryl, aralkyl, heterocyclic or polycyclic group;

R$^6$ represents an optionally substituted alkyl, alkenyl, alkynyl, cycloalkyl, aryl, aralkyl, heterocyclic or polycyclic group;

R$^8$ represents a hydrogen atom or an optionally substituted alkyl, alkenyl, alkynyl, aryl or alkoxycarbonyl group;

R$^9$ represents a nitro group or an optionally substituted alkyl, alkenyl, alkynyl, aryl, alkanoyl, aroyl, alkoxycarbonyl or aryloxycarbonyl group; or R$^8$ and R$^9$ together with the interjacent carbon atom represent an optionally substituted cycloalkyl or polycyclic group; and Ar represents an optionally substituted aryl or heteroaryl group;

optional substituents being selected from the group consisting of halogen atoms, nitro, cyano, hydroxyl, cyclalkyl, alkyl, alkenyl, haloalkyl, cycloalkyloxy, alkoxy, haloalkoxy, amino, alkylamino, dialkylamino, formyl, alkoxycarbonyl, oxo, carboxyl, carboxylato, alkanoyl, alkylthio, alkylsulphinyl, alkylsulphonyl, alkylsulphonato, carbamoyl, alkylamido, aryl, aralkyl; halo-, alkyl-, haloalkyl- or alkoxy-substituted aryl, heterocyclic and alkyl- or aryl-substituted heterocyclic groups with the provisos that (i) when X is a group —NR$^1$R$^2$, then Y is an oxo group;

(ii) when X is a hydrogen atom, then Y is not an oxo, methoxy, ethoxy or 3-carboxypropanoyloxy group; and (iii) when Y is a hydrogen atom or a hydroxyl group, then X is a group —CHR$^8$R$^9$.

2. A method according to claim 1 in which X represents a hydrogen atom.

3. A method of killing a cell comprising exposing said cell to a compound of the general formula I

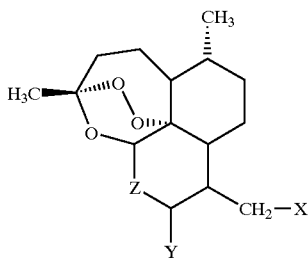

(I)

or a salt thereof, in which X represents a hydrogen atom or a group —NR$^1$R$^2$, —CHR$^8$R$^9$, or Ar, Y represents a hydrogen or halogen atom, an oxo or hydroxyl group, an optionally substituted cycloalkyl, aryl, C-linked heteroaryl or heterocyclylalkyl group or a group —NR$^3$R$^4$, —O—CO—R$^5$ or —OR$^6$; and Z represents an oxygen atom where R$^1$ and R$^2$ independently represent an optionally substituted alkyl, cycloalkyl, aryl or aralkyl group; or R$^1$ and R$^2$ together with the interjacent nitrogen atom represent an optionally substituted heterocyclic group or an amino group derived from an optionally substituted amino acid ester;

R$^3$ represents a hydrogen atom or an optionally substituted alkyl, alkenyl or alkynyl group;

R$^4$ represents an optionally substituted alkyl, alkenyl, alkynyl, cycloalkyl, aryl or aralkyl group; or R$^3$ and R$^4$ together with the interjacent nitrogen atom represent an optionally substituted heterocyclic group or an amino group derived from an optionally substituted amino acid ester;

R$^5$ represents an optionally substituted alkyl, alkenyl, alkynyl, cycloalkyl, aryl, aralkyl, heterocyclic or polycyclic group;

R$^6$ represents an optionally substituted alkyl, alkenyl, alkynyl, cycloalkyl, aryl, aralkyl, heterocyclic or polycyclic group;

R$^8$ represents a hydrogen atom or an optionally substituted alkyl, alkenyl, alkynyl, aryl or alkoxycarbonyl group;

R$^9$ represents a nitro group or an optionally substituted alkyl, alkenyl, alkynyl, aryl, alkanoyl, aroyl, alkoxycarbonyl or aryloxycarbonyl group; or R$^8$ and R$^9$ together with the interjacent carbon atom represent an optionally substituted cycloalkyl or polycyclic group; and Ar represents an optionally substituted aryl or heteroaryl group;

optional substituents being selected from the group consisting of halogen atoms, nitro, cyano, hydroxyl, cycloalkyl, alkyl, alkenyl, haloalkyl, cycloalkyloxy, alkoxy, haloalkoxy, amino, alkylamino, dialkylamino, formyl, alkoxycarbonyl, oxo, carboxyl, carboxylato, alkanoyl, alkylthio, alkylsulphinyl, alkylsulphonyl, alkylsulphonato, carbamoyl, alkylamido, aryl, aralkyl; halo-, alkyl-, haloalkyl- or alkoxy-substituted aryl, heterocyclic acid alkyl- or aryl-substituted heterocyclic groups with the provisos that (i) when X is a group —NR$^1$R$^2$, then Y is an oxo group;

(ii) when X is a hydrogen atom, then Y is not an oxo, methoxy, ethoxy or 3-carboxypropanoyloxy group; and (iii) when Y is a hydrogen atom or a hydroxyl group, then X is a group —CHR$^8$R$^9$.

4. A method according to claim 3 in which X represents a hydrogen atom.

5. A compound of the general formula IV

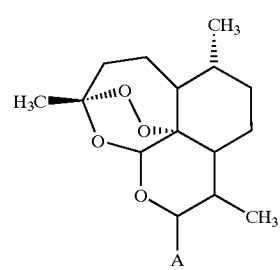

IV or a salt thereof, in which A represents an optionally substituted aryl or C-linked heteroaryl group or a group —NR$^3$R$^4$, —O—CO—R$^5$ or OR$^6$; where R$^3$ represents a hydrogen atom or an optionally substituted alkyl group and $R^4$ represents an optionally substituted aryl or aralkyl group, or $R^3$ and $R^4$ together with the interjacent nitrogen atom represent an optionally substituted heterocyclic group; $R^5$ represents an optionally substituted aryl, aralkyl, heterocyclic or polycyclic group; and $R^6$ represents an optionally substituted aryl, aralkyl, heterocyclic or polycyclic group; optional substituents being selected from the group consisting of halogen atoms, nitro, cyano, hydroxyl, cycloalkyl, alkyl, alkenyl, haloalkyl, cycloalkyloxy, alkoxy, haloalkoxy, amino, alkylamino, dialkylamino, formyl, alkoxycarbonyl, oxo, carboxyl, carboxylato, alkanoyl, alkylthio, alkylsulphinyl, alkylsulphonyl, alkylsulphonato, carbamoyl, alkylamido, aryl, aralkyl; halo-, alkyl-, haloalkyl- or alkoxy-substituted aryl, heterocyclic and alkyl- or aryl-substituted heterocyclic groups.

6. A compound of the general formula VI

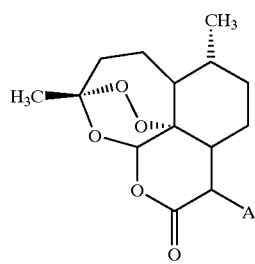

VI in which A represents a group —$CH_2$—$NR^1R^2$ where one of $R^1$ and $R^2$ represents an optionally substituted aryl or aralkyl group and the other of $R^1$ and $R^2$ represents an optionally substituted alkyl, cycloalkyl, aryl, or aralkyl group, or $R^1$ and $R^2$ together with the interjacent nitrogen atom represent an optionally substituted heterocyclic group or an amino group derived from an optionally substituted amino acid ester which contains an aromatic or heterocyclic moiety.

7. A compound of the general formula VII

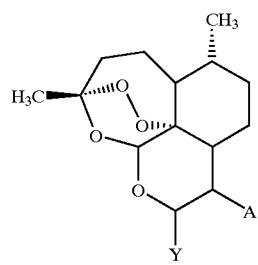

VII in which A represents a group —$CH_2$—$CHR^8R^9$ where $R^8$ represents a hydrogen atom or an optionally substituted alkyl, alkenyl, alkynyl, aryl or alkoxycarbonyl, group; and $R^9$ represents a nitro group or an optionally substituted alkyl, alkenyl, alkynyl, aryl, alkanoyl, aroyl, alkoxycarbonyl or aryloxycarbonyl group, with the proviso that at least one of $R^8$ and $R^9$ represents or contains an aromatic moiety, or $R^8$ and $R^9$ together with the interjacent carbon atom represent an optionally substituted polycyclic group containing an aromatic moiety; with the proviso that when $R^8$ represents a hydrogen atom and $R^9$ represents a benzyl or 4-chlorobenzyl group, then Y represents a hydroxyl group; optional substituents being selected from the group consisting of halogen atoms, nitro, cyano, hydroxyl, cycloalkyl, alkyl, alkenyl, haloalkyl, cycloalkyloxy, alkoxy, haloalkoxy, amino, alkylamino, dialkylamino, formyl, alkoxycarbonyl, oxo, carboxyl, carboxylato, alkanoyl, alkylthio, alkylsulphinyl, alkylsulphonyl, alkylsulphonato, carbamoyl, alkylamido, aryl, aralkyl; halo-, alkyl-, haloalkyl- or alkoxy-substituted aryl, heterocyclic and alkyl- or aryl-substituted heterocyclic groups; and Y is a hydrogen atom or an oxo or hydroxy group.

* * * * *

UNITED STATES PATENT AND TRADEMARK OFFICE
CERTIFICATE OF CORRECTION

PATENT NO.    : 6,649,647 B1
DATED         : November 18, 2003
INVENTOR(S)   : Haynes et al.

It is certified that error appears in the above-identified patent and that said Letters Patent is hereby corrected as shown below:

<u>Column 83,</u>
Line 31, delete the word "cyclalkyl" and insert the word -- cycloalkyl --

<u>Column 84,</u>
Line 41, delete the word "acid" and insert the word -- and --

Signed and Sealed this

Thirteenth Day of January, 2004

JON W. DUDAS
*Acting Director of the United States Patent and Trademark Office*